United States Patent
Tanaka et al.

(10) Patent No.: US 11,117,930 B2
(45) Date of Patent: Sep. 14, 2021

(54) PEPTIDE INHIBITORS OF TRANSCRIPTION FACTOR AGGREGATION

(71) Applicant: ADRX, INC., Thousand Oaks, CA (US)

(72) Inventors: Shiho Tanaka, Redondo Beach, CA (US); Ashley Wright, Los Angeles, CA (US); James Treanor, Lake Sherwood, CA (US); Marcin Apostol, Malibu, CA (US)

(73) Assignee: ADRX, INC., Thousand Oaks, CA (US)

( * ) Notice: Subject to any disclaimer, the term of this patent is extended or adjusted under 35 U.S.C. 154(b) by 0 days.

(21) Appl. No.: 16/487,381

(22) PCT Filed: Feb. 23, 2018

(86) PCT No.: PCT/US2018/019417
§ 371 (c)(1),
(2) Date: Aug. 20, 2019

(87) PCT Pub. No.: WO2018/156892
PCT Pub. Date: Aug. 30, 2018

(65) Prior Publication Data
US 2020/0062804 A1  Feb. 27, 2020

Related U.S. Application Data

(60) Provisional application No. 62/462,815, filed on Feb. 23, 2017.

(51) Int. Cl.
*A61K 38/00* (2006.01)
*C07K 7/06* (2006.01)
*C07K 14/47* (2006.01)

(52) U.S. Cl.
CPC ............ *C07K 7/06* (2013.01); *C07K 14/4711* (2013.01); *C07K 14/4746* (2013.01); *A61K 38/00* (2013.01)

(58) Field of Classification Search
CPC ................ A61K 38/00; C07K 14/4711; C07K 14/4746; C07K 7/06
See application file for complete search history.

(56) References Cited

U.S. PATENT DOCUMENTS

| | | |
|---|---|---|
| 5,858,351 A | 1/1999 | Podsakoff et al. |
| 6,015,709 A | 1/2000 | Natesan |
| 6,211,163 B1 | 4/2001 | Podsakoff et al. |
| 6,325,998 B1 | 12/2001 | Podsakoff et al. |
| 7,094,604 B2 | 8/2006 | Snyder et al. |
| 7,198,951 B2 | 4/2007 | Gao et al. |
| 7,355,008 B2 | 4/2008 | Stavenhagen et al. |
| 7,381,408 B2 | 6/2008 | Mezo et al. |
| 7,588,757 B2 | 9/2009 | Ozawa et al. |
| 7,588,772 B2 | 9/2009 | Kay et al. |
| 8,283,151 B2 | 10/2012 | Schmidt et al. |
| 8,292,769 B2 | 10/2012 | Lawson, Jr. |
| 9,102,949 B2 | 8/2015 | Gao et al. |
| 9,217,155 B2 | 12/2015 | Gao et al. |
| 9,585,971 B2 | 3/2017 | Deverman et al. |
| 2008/0286808 A1 | 11/2008 | Schellenberger et al. |
| 2009/0117156 A1 | 5/2009 | Passini et al. |
| 2016/0120960 A1 | 5/2016 | McIvor et al. |

FOREIGN PATENT DOCUMENTS

| | | | |
|---|---|---|---|
| EP | 1857552 A1 | 11/2007 | |
| EP | 2678433 A1 | 1/2014 | |
| WO | 87/05330 A1 | 9/1987 | |
| WO | WO 1998021237 A2 * | 5/1998 | ......... C07K 14/4746 |
| WO | 01/89583 A2 | 11/2001 | |
| WO | 2005/120581 A2 | 12/2005 | |
| WO | 2009/023270 A2 | 2/2009 | |
| WO | 2010/012850 A1 | 2/2010 | |
| WO | 2011/126808 A2 | 10/2011 | |
| WO | 2011/157713 A2 | 12/2011 | |
| WO | 2012/057363 A1 | 5/2012 | |
| WO | 2012/090150 A2 | 7/2012 | |
| WO | 2012/115980 A1 | 8/2012 | |
| WO | 2012/130785 A1 | 10/2012 | |
| WO | WO-2012130785 A1 * | 10/2012 | ......... G01N 33/5011 |
| WO | 2013/034982 A2 | 3/2013 | |
| WO | WO-2013034982 A2 * | 3/2013 | .............. A61P 25/28 |
| WO | 2013/098337 A1 | 7/2013 | |
| WO | 2014/001229 A2 | 1/2014 | |
| WO | 2014/009259 A1 | 1/2014 | |
| WO | 2014/041505 A1 | 3/2014 | |
| WO | 2014/056813 A1 | 4/2014 | |

(Continued)

OTHER PUBLICATIONS

SeJin et al. Role of p53 isoforms and aggregations in cancer. 2016. Medicine (2016) 95:26 (Year: 2016).*
Robert Peter Gale "Overview of Cancer Therapy," last modified Aug. 2018, In Merck Manual Consumer Version, accessed on May 8, 2020 at <https://www.merckmanuals.com/professional/hematology-and-oncology/principles-of-cancer-therapy/overview-of-cancer-therapy> (Year: 2018).*
Robert Peter Gale "Cancer Treatment Principles, last modified Aug. 2018, In Merck Manual Consumer Version, accessed on May 8, 2020 at <https://www.merckmanuals.com/home/cancer/prevention-and-treatment-of-cancer/cancer-treatment-principles>." (Year: 2018).*
What is Cancer? National cancer Institute, accessed on May 8, 2020 <https://www.cancer.gov/about-cancer/understanding/what-is-cancer> (Year: 2020).*

(Continued)

*Primary Examiner* — James H Alstrum-Acevedo
*Assistant Examiner* — Mercy H Sabila
(74) *Attorney, Agent, or Firm* — Marshall, Gerstein & Borun LLP

(57) ABSTRACT

This invention relates to materials, such as peptides, and methods to inhibit the aggregation transcription factors, for example p53 inhibitors, p63 inhibitors and p73 inhibitors. More specifically, the invention relates to cancer chemotherapeutics. More specifically, the invention provides pharmaceutical compositions and methods of treating cancer with certain peptides.

22 Claims, 3 Drawing Sheets
Specification includes a Sequence Listing.

(56) References Cited

FOREIGN PATENT DOCUMENTS

| WO | 2014/131892 | A1 | | 9/2014 | |
|----|----|----|----|----|----|
| WO | 2014/147193 | A1 | | 9/2014 | |
| WO | 2014/182961 | A1 | | 11/2014 | |
| WO | WO-2014182961 | A1 | * | 11/2014 | ............. A61P 43/00 |
| WO | 2015/075747 | A1 | | 5/2015 | |
| WO | 2015/168666 | A2 | | 11/2015 | |
| WO | 2016/073693 | A2 | | 5/2016 | |
| WO | 2016/087842 | A1 | | 6/2016 | |
| WO | 2016/102339 | A1 | | 6/2016 | |
| WO | 2016/126993 | A1 | | 8/2016 | |
| WO | 2016/172722 | A1 | | 10/2016 | |

OTHER PUBLICATIONS

Cancer prevention overview, (PDQ®) Patient Version. National cancer Institute, accessed on May 8, 2020 <https://www.cancer.gov/about-cancer/causes-prevention/patient-prevention-overview-pdq> (Year: 2020).*

Medical news today. Accessed May 2020, at <https://www.medicalnewstoday.com/articles/322700> (Year: 2018).*

Bullock et al., Rescuing the function of mutant p53, Nat. Rev. Cancer, 1:68-76 (2001).

Eisenberg et al., The amyloid state of proteins in human diseases, Cell. 148:1188-203 (2012).

Ghosh et al., Investigating the Intrinsic Aggregation Potential of Evolutionarily Conserved Segments in P53, Biochemistry. 53:5995-6010 (2014).

International Preliminary Report on Patentability received for PCT Patent Application No. PCT/US18/19417, dated Sep. 6, 2019, 8 pages.

International Search Report and Written Opinion received for PCT Patent Application No. PCT/US18/19417, dated May 25, 2018, 11 pages.

Levy et al., Co-localization of mutant p53 and amyloid-like protein aggregates in breast tumors, Int. J. Biochem. Cell Biol. 43:60-4 (2011).

Soragni et al., A designed inhibitor of p53 aggregation rescues p53 tumor suppression in ovarian carcinomas, Cancer Cell., 29(1):90-103 (2016).

Soussi et al., Locus-specific mutation databases: Pitfalls and good practice based on the p53 experience, Nat. Rev. Cancer. 6:83-90 (2006).

Xu et al., Gain of function of mutant p53 by coaggregation with multiple tumor suppressors, Nat. Chem. Biol. 5:285-95 (2011).

* cited by examiner

SEQ ID NO: 226

SEQ ID NO: 227

```
SEQUENCE LISTING

<160> NUMBER OF SEQ ID NOS: 239

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Ile, Leu, Arg, Ala, Trp, Phe, Thr, Chg,
      Phg, Tyr, D-Arg, D-His, D-Leu, D-Ile, D-Lys, D-Tyr, D-Ser, D-Trp,
      D-Ala, D-Gln or D-Phe
<220> FEATURE:
<221> NAME/KEY: MISC_FEATURE
<222> LOCATION: (2)..(2)
<223> OTHER INFORMATION: Xaa is Arg, homo-Arg, Phe, Trp, Gln, His, Ser,
      Thr, Val, Leu, Ala, Tyr, D-Phe, D-Arg, D-His, D-Leu, D-Ile, D-Val,
      D-Met, D-Tyr, D-Ala, D-Gln or D-Trp
<220> FEATURE:
<221> NAME/KEY: MISC_FEATURE
<222> LOCATION: (3)..(3)
<223> OTHER INFORMATION: Xaa is Chg, Ile, N-Me-Ile, Arg, Tyr, Lys, Val,
      Phe, Phg, Ala, Leu, D-Arg, D-Lys, D-His, D-Met, D-Ala, D-Gln,
      D-Glu, D-Trp or D-Tyr
<220> FEATURE:
<221> NAME/KEY: MISC_FEATURE
<222> LOCATION: (4)..(4)
<223> OTHER INFORMATION: Xaa is N-Me-Lys, homo-Arg, Arg, Lys, Glu, Met,
```

```
        Gln, Ile, Leu, Ala, Phe, Tyr, D-Arg, D-Lys, D-His, D-Ala, D-Ile,
        D-Met, D-Gln, D-Trp, D-Phe or D-Tyr
<220> FEATURE:
<221> NAME/KEY: MISC_FEATURE
<222> LOCATION: (5)..(5)
<223> OTHER INFORMATION: Xaa is His, Arg, Lys, Gln, Tyr, Thr, Ile, Leu,
        Ala, Phe, D-His, D-Arg, D-Lys, D-Ala, D-Leu, D-Gln, D-Trp, D-Phe
        or D-Tyr
<220> FEATURE:
<221> NAME/KEY: MISC_FEATURE
<222> LOCATION: (6)..(6)
<223> OTHER INFORMATION: Xaa is Tyr, Thr, Ala, Gln, Leu, Val, His, Lys,
        Arg, Trp, Phe, D-Arg, D-Gln, D-Ala, D-Lys, D-Tyr, D-Trp or D-His
<220> FEATURE:
<221> NAME/KEY: MISC_FEATURE
<222> LOCATION: (7)..(7)
<223> OTHER INFORMATION: Xaa is Arg, Ala, His, Thr, Ser, Glu, Lys,
        D-Arg, D-Lys, D-Ala, D-Asn, D-Gln, D-Ser, D-His or is absent
<220> FEATURE:
<221> NAME/KEY: MISC_FEATURE
<222> LOCATION: (8)..(8)
<223> OTHER INFORMATION: Xaa is Pro or is absent

<400> SEQUENCE: 1

Xaa Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Phg

<400> SEQUENCE: 2

Ile Arg Xaa Arg Arg Tyr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Homo-Arg
<220> FEATURE:
<221> NAME/KEY: MISC_FEATURE
<222> LOCATION: (4)..(4)
<223> OTHER INFORMATION: Homo-Arg

<400> SEQUENCE: 3

Ile Arg Ile Arg Arg Tyr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Phg
<220> FEATURE:
<221> NAME/KEY: MISC_FEATURE
```

```
<222> LOCATION: (3)..(3)
<223> OTHER INFORMATION: Xaa is Phg

<400> SEQUENCE: 4

Xaa Arg Xaa Arg Arg Tyr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homo-Arg

<400> SEQUENCE: 5

Ile Arg Ile Arg Arg Tyr Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Homo-Arg
<220> FEATURE:
<221> NAME/KEY: MISC_FEATURE
<222> LOCATION: (4)..(4)
<223> OTHER INFORMATION: Homo-Arg

<400> SEQUENCE: 6

Ile Arg Ile Arg Arg Trp Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 7

Xaa Arg Xaa Arg Arg Tyr Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
```

```
<400> SEQUENCE: 8

Ile Arg Xaa Arg Arg Tyr Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Ile, Leu, Arg, Ala, Trp, Phe, Thr or Tyr
<220> FEATURE:
<221> NAME/KEY: MISC_FEATURE
<222> LOCATION: (2)..(2)
<223> OTHER INFORMATION: Xaa is Arg, Phe, Trp, Gln, His, Ser, Thr, Val,
      Leu, Ala or Tyr
<220> FEATURE:
<221> NAME/KEY: MISC_FEATURE
<222> LOCATION: (3)..(3)
<223> OTHER INFORMATION: Xaa is Ile, N-Me-Ile, Arg, Tyr, Lys, Val, Phe,
      Ala, or Leu
<220> FEATURE:
<221> NAME/KEY: MISC_FEATURE
<222> LOCATION: (4)..(4)
<223> OTHER INFORMATION: Xaa is Arg, Lys, N-Me-Lys, Glu, Met, Gln, Ile,
      Leu, Ala, Phe, or Tyr
<220> FEATURE:
<221> NAME/KEY: MISC_FEATURE
<222> LOCATION: (5)..(5)
<223> OTHER INFORMATION: Xaa is His, Arg, Lys, Gln, Tyr, Thr, Ile, Leu,
      Ala or Phe
<220> FEATURE:
<221> NAME/KEY: MISC_FEATURE
<222> LOCATION: (6)..(6)
<223> OTHER INFORMATION: Xaa is Tyr, Thr, Ala, Gln, Leu, Val, His, Lys,
      Arg, Trp, or Phe
<220> FEATURE:
<221> NAME/KEY: MISC_FEATURE
<222> LOCATION: (7)..(7)
<223> OTHER INFORMATION: Xaa is Arg, Ala, His, Thr, Ser, Glu, Lys or is
      absent
<220> FEATURE:
<221> NAME/KEY: MISC_FEATURE
<222> LOCATION: (8)..(8)
<223> OTHER INFORMATION: Xaa is Pro or is absent

<400> SEQUENCE: 9

Xaa Xaa Xaa Xaa Xaa Xaa Xaa Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Leu Thr Arg Ile Thr Tyr His
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11
```

Ile Arg Ile Arg His Tyr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Ile Arg Ile Arg Arg Tyr Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Ile Arg Ile Arg Ala Tyr Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Leu Arg Ile Arg Tyr Trp Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Ile Arg Ile Arg Arg Ala Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Ile Arg Ile Ala Arg Tyr Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Ile Arg Ile Arg Arg Tyr Ala 1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Ile Arg Ile Tyr Arg Tyr Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Thr Arg Ile Arg Phe Tyr Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (7)..(7)
<223> OTHER INFORMATION: C-terminal amidation

<400> SEQUENCE: 20

Ile Arg Ile Arg Arg Tyr Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Leu Tyr Ile Arg Tyr Leu Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Leu Arg Ile Lys Tyr His Arg
1               5

<210> SEQ ID NO 23
<211> LENGTH: 7
<212> TYPE: PRT

```
<213> ORGANISM: Artificial Sequence
<220> FEATURE:
<223> OTHER INFORMATION: Synthetic peptide

<400> SEQUENCE: 23

Ile Ala Ile Arg Arg Tyr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Leu Arg Ile Arg Arg Tyr Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Leu Trp Ile Lys Tyr His Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Ile Arg Ile Arg Arg Trp Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Leu Arg Ile Tyr Arg Val Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Trp Thr Ile Lys Leu Trp His
1               5

<210> SEQ ID NO 29
<211> LENGTH: 7
<212> TYPE: PRT
<213> ORGANISM: Artificial Sequence
```

<220> FEATURE:
<223> OTHER INFORMATION: Synthetic peptide

<400> SEQUENCE: 29

Leu Arg Ile Arg Phe Phe Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Leu Thr Ile Arg Tyr Tyr Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Tyr Arg Leu Arg Tyr Leu Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Leu Phe Arg Tyr Tyr Gln Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Leu Val Ile Arg Tyr His Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Arg Phe Tyr Arg Tyr Leu Arg
1               5

<210> SEQ ID NO 35
<211> LENGTH: 7
<212> TYPE: PRT
<213> ORGANISM: Artificial Sequence
<220> FEATURE:

```
<223> OTHER INFORMATION: Synthetic peptide
<220> FEATURE:
<221> NAME/KEY: MOD_RES
<222> LOCATION: (4)..(4)
<223> OTHER INFORMATION: N-methyl-Lys

<400> SEQUENCE: 35

Leu Arg Ile Lys Tyr His Arg
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Ile Arg Ile Arg His Tyr Arg Pro
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

Ala Arg Ile Arg Arg Tyr Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Leu Arg Leu Arg His Tyr Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Leu Tyr Ile Lys Tyr His Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Tyr Thr Arg Ile Thr Tyr His
1               5

<210> SEQ ID NO 41
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 41

Leu Arg Ile Tyr His His Lys
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Ile Arg Leu Arg Arg Tyr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide

<400> SEQUENCE: 43

Tyr Arg Leu Arg Tyr Val Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Leu Tyr Ile Arg Tyr Thr His
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic peptide

<400> SEQUENCE: 45

Leu Arg Ile Arg His Tyr Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide

<400> SEQUENCE: 46

Phe Arg Ile Arg Arg Tyr Arg
1               5

<210> SEQ ID NO 47
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 47

Leu Tyr Ile Arg Leu Thr His
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Leu Thr Ile Arg Leu Trp His
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Leu Tyr Ile Arg Thr Leu His
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Trp Thr Ile Arg Tyr Tyr Lys
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide

<400> SEQUENCE: 51

Ile Arg Ile Arg Arg Tyr
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Leu Phe Ile Lys Tyr His Arg
1               5

<210> SEQ ID NO 53
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 53

Thr Arg Ile Tyr Arg Tyr Lys
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide

<400> SEQUENCE: 54

Trp Thr Ile Arg Tyr Tyr His
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Leu Ala Ile Lys Tyr His Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Trp Thr Arg Ile Thr Leu Lys
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Leu Thr Ile Lys Leu Trp His
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Leu Leu Ile Lys Tyr His Ala
1               5

<210> SEQ ID NO 59
<211> LENGTH: 7
<212> TYPE: PRT
<213> ORGANISM: Artificial Sequence
<220> FEATURE:
```

<223> OTHER INFORMATION: Synthetic peptide

<400> SEQUENCE: 59

Trp Thr Arg Ile Tyr Leu His
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Leu Arg Ile Arg His Val Lys
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Leu Leu Ile Lys Tyr His Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Ile Arg Ile Arg Arg Ala Ala
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Leu Tyr Ile Arg Thr Tyr His
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Leu Leu Ile Lys Ala His Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic peptide

<400> SEQUENCE: 65

Trp Tyr Ile Arg Leu Trp Lys
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic peptide

<400> SEQUENCE: 66

Ile Tyr Ile Tyr His Gln Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide

<400> SEQUENCE: 67

Arg Leu Tyr Ile Arg Leu Ser
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic peptide

<400> SEQUENCE: 68

Trp Tyr Ile Arg Thr Tyr His
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic peptide

<400> SEQUENCE: 69

Trp Tyr Ile Arg Leu Trp His
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide

<400> SEQUENCE: 70

Leu Thr Ile Arg Thr Trp His
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 71

Leu Leu Ile Lys Tyr Ala Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic peptide

<400> SEQUENCE: 72

Leu Tyr Ile Arg Thr Trp His
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic peptide

<400> SEQUENCE: 73

Leu Tyr Ile Arg His Lys
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide

<400> SEQUENCE: 74

Leu Thr Ile Arg Leu Thr His
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: N-methyl-Ile

<400> SEQUENCE: 75

Leu Arg Ile Lys Tyr His Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic peptide

<400> SEQUENCE: 76

Thr Leu Ile Ile Tyr His Arg
1               5

<210> SEQ ID NO 77
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 77

Leu Tyr Ile Phe Arg His Thr
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Trp Tyr Ile Arg Leu Thr His
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide

<400> SEQUENCE: 79

Trp Thr Arg Ile Leu Trp His
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Thr Tyr Ile Arg Tyr Leu Arg
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic peptide

<400> SEQUENCE: 81

Trp Thr Arg Ile Tyr Tyr His
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide

<400> SEQUENCE: 82

Leu Thr Ile Met Leu Trp His
1               5

<210> SEQ ID NO 83
<211> LENGTH: 7
<212> TYPE: PRT
<213> ORGANISM: Artificial Sequence
<220> FEATURE:
```

```
<223> OTHER INFORMATION: Synthetic peptide

<400> SEQUENCE: 83

Trp Thr Lys Ile Thr Leu His
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide

<400> SEQUENCE: 84

Leu Phe Ile Tyr Tyr Gln Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide

<400> SEQUENCE: 85

Ile Gln Ile Tyr Arg Tyr Lys
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide

<400> SEQUENCE: 86

Ile Arg Ile Arg Ala Ala Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide

<400> SEQUENCE: 87

Leu Leu Ile Ala Tyr His Arg
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide

<400> SEQUENCE: 88

Leu Phe Ile Phe Tyr His Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 89

Ile Arg Val Tyr Lys Tyr Ser
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide

<400> SEQUENCE: 90

Leu Thr Ile Gln Leu Trp His
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide

<400> SEQUENCE: 91

Tyr Tyr Ile Arg Tyr Tyr Lys
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Ile Arg Phe Arg Arg Tyr Arg
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic peptide

<400> SEQUENCE: 93

Trp Arg Ile Arg Arg Tyr Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide

<400> SEQUENCE: 94

Trp Thr Ile Met Leu Trp His
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 95

Leu Thr Ile Arg Thr Leu His
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide

<400> SEQUENCE: 96

Ala Leu Ile Lys Tyr His Arg
1               5

<210> SEQ ID NO 97
<211> LENGTH: 6
<212> TYPE: PRT
<213> ORGANISM: Artificial Sequence
<220> FEATURE:
<223> OTHER INFORMATION: Synthetic peptide

<400> SEQUENCE: 97

Leu His Ile Glu His Arg
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic peptide

<400> SEQUENCE: 98

Ile Phe Val Tyr His His
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide

<400> SEQUENCE: 99

Trp Thr Ile Lys Leu Thr His
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic peptide

<400> SEQUENCE: 100

Ile His Ile Glu Ile Lys
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide

<400> SEQUENCE: 101
```

Trp Thr Ile Arg Thr Trp His
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 102

Tyr Thr Tyr Met Leu Trp Lys
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic peptide

<400> SEQUENCE: 103

Leu Ser Ile Arg Gln His
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide

<400> SEQUENCE: 104

Ile Arg Ala Arg Arg Tyr Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic peptide

<400> SEQUENCE: 105

Tyr Tyr Ile Arg Thr Tyr His
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic peptide

<400> SEQUENCE: 106

Leu Leu Ala Lys Tyr His Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic peptide

<400> SEQUENCE: 107

Ile Trp Ile Arg Arg Trp Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic peptide

<400> SEQUENCE: 108

Ala Tyr Tyr Tyr Arg His Arg
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic peptide

<400> SEQUENCE: 109

Thr Tyr Val Tyr Arg Arg Arg
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic peptide

<400> SEQUENCE: 110

Thr Arg Ile Tyr Arg Val Lys
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide

<400> SEQUENCE: 111

Thr Tyr Ile Tyr Arg Gln Arg
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic peptide

<400> SEQUENCE: 112

Leu Thr Arg Ile Leu Thr His
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic peptide

<400> SEQUENCE: 113

Ile Leu Arg Leu Tyr Phe Arg

```
<210> SEQ ID NO 114
<211> LENGTH: 7
<212> TYPE: PRT
<213> ORGANISM: Artificial Sequence
<220> FEATURE:
<223> OTHER INFORMATION: Synthetic peptide

<400> SEQUENCE: 114

Phe Phe Arg Leu Tyr Leu Arg
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic peptide

<400> SEQUENCE: 115

Leu Thr Arg Ile Leu Trp His
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic peptide

<400> SEQUENCE: 116

Phe Arg Leu Tyr Ile His
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic peptide

<400> SEQUENCE: 117

Thr Phe Val Phe Arg His Arg
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic peptide

<400> SEQUENCE: 118

Ile Arg Ile Arg Arg Tyr Glu
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide

<400> SEQUENCE: 119

Tyr Thr Ile Gln Leu Trp His
1               5
```

<210> SEQ ID NO 120
<211> LENGTH: 7
<212> TYPE: PRT
<213> ORGANISM: Artificial Sequence
<220> FEATURE:
<223> OTHER INFORMATION: Synthetic peptide

<400> SEQUENCE: 120

Thr Phe Ile Leu Arg Leu Thr
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide

<400> SEQUENCE: 121

Tyr Thr Tyr Glu Tyr Trp His
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Gln
<220> FEATURE:
<221> NAME/KEY: MOD_RES
<222> LOCATION: (7)..(7)
<223> OTHER INFORMATION: D-Arg

<400> SEQUENCE: 122

His Gln Arg Arg Tyr Gln Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Lys

```
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 123

Lys Phe Arg Phe Tyr His Arg
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Ile
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 124

Arg Ile His Tyr Phe Arg Arg
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 125

His Trp Arg Trp Leu Arg Arg
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 126

Arg Trp Arg Tyr Leu Arg Arg
1               5

<210> SEQ ID NO 127
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Lys

<400> SEQUENCE: 127

Arg Phe His Tyr Phe Arg Lys
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Lys
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-His

<400> SEQUENCE: 128

Lys Leu Lys Lys Leu His
1               5

<210> SEQ ID NO 129
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 129

Lys Trp Arg Trp Tyr Arg Arg
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 130

Arg Phe Tyr Tyr His Arg Arg
1               5

<210> SEQ ID NO 131
<211> LENGTH: 7
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 131

Trp Trp Arg Trp Tyr Arg Arg
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 132

Arg Phe Tyr Arg Arg His Arg
1               5
```

```
<210> SEQ ID NO 133
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-His

<400> SEQUENCE: 133

Lys Tyr Arg Trp Tyr Arg His
1               5

<210> SEQ ID NO 134
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg

<400> SEQUENCE: 134

Phe Trp Arg Trp His Arg
1               5
```

```
<210> SEQ ID NO 135
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Gln
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 135

Gln Gln Arg Tyr Tyr Trp Arg
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Ile
<220> FEATURE:
<221> NAME/KEY: MOD_RES
<222> LOCATION: (5)..(5)
<223> OTHER INFORMATION: D-Trp
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Asn

<400> SEQUENCE: 136

His Leu Arg Ile Trp Arg Asn
```

```
<210> SEQ ID NO 137
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 137

Phe Phe Arg Phe His Arg Arg
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Leu
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg
```

```
<400> SEQUENCE: 138

Leu Trp Arg Arg Tyr His Arg
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Ile
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Lys

<400> SEQUENCE: 139

Arg Ile Arg Trp Tyr Trp Lys
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
```

```
<222> LOCATION: (7)..(7)
<223> OTHER INFORMATION: D-Arg

<400> SEQUENCE: 140

Tyr Gln Trp Arg His Trp Arg
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 141

Arg Trp Tyr Trp His His Arg
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Ser
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (6)..(6)
```

```
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 142

Ser Phe Trp Tyr Lys Arg Arg
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-Glu
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 143

Arg Phe Glu Phe Arg His Arg
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Tyr
```

```
<220> FEATURE:
<221> NAME/KEY: MOD_RES
<222> LOCATION: (6)..(6)
<223> OTHER INFORMATION: D-Gln
<220> FEATURE:
<221> NAME/KEY: MOD_RES
<222> LOCATION: (7)..(7)
<223> OTHER INFORMATION: D-Arg

<400> SEQUENCE: 144

Tyr Gln Tyr Tyr Tyr Gln Arg
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 145

Arg Gln Trp Tyr His Trp Arg
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Tyr
<220> FEATURE:
```

```
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 146

His Gln Arg Tyr Tyr Trp Arg
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 147

His Trp Arg Tyr His Arg Arg
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
```

```
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 148

Arg Trp His Trp His Trp Arg
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 149

Phe Trp Arg Trp His Arg Arg
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
```

```
<223> OTHER INFORMATION: D-Arg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 150

Phe Phe Arg Phe His His Arg
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 151

Arg Trp Arg Trp His His Arg
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Trp
```

```
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Lys

<400> SEQUENCE: 152

His Trp Arg Trp Tyr Trp Lys
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-His
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 153

Phe Trp Arg His Lys His Arg
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Gln
<220> FEATURE:
```

```
<221> NAME/KEY: MOD_RES
<222> LOCATION: (2)..(2)
<223> OTHER INFORMATION: D-Ile
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 154

Gln Ile Arg Tyr Phe Arg Arg
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 155

Phe Trp Arg Trp Ala Arg Arg
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: D-Gln
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Met
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 156

Gln Phe Arg Met His His Arg
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 157

Tyr Gln Tyr Tyr Phe Trp Arg
1               5

<210> SEQ ID NO 158
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: D-Ser
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 158

Ser Trp Trp Phe Arg His Arg
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 159

Tyr Gln Trp Arg Tyr Arg Arg
1               5

<210> SEQ ID NO 160
<211> LENGTH: 7
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Lys

<400> SEQUENCE: 160

His Leu Arg Tyr His Arg Lys
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Gln

<400> SEQUENCE: 161

Tyr Gln Trp Tyr Arg Trp Gln
1               5
```

```
<210> SEQ ID NO 162
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Leu
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 162

Leu Trp Arg Trp Tyr Arg Arg
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Ile
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Gln
<220> FEATURE:
<221> NAME/KEY: MOD_RES
<222> LOCATION: (7)..(7)
<223> OTHER INFORMATION: D-Lys

<400> SEQUENCE: 163
```

```
Arg Trp Arg Ile Leu Gln Lys
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 164

Arg Gln His Tyr Arg Trp Arg
1               5

<210> SEQ ID NO 165
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-His
```

<400> SEQUENCE: 165

Arg Leu His Trp Lys His His
1               5

<210> SEQ ID NO 166
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Met
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Trp
<220> FEATURE:
<221> NAME/KEY: MOD_RES
<222> LOCATION: (6)..(6)
<223> OTHER INFORMATION: D-Gln
<220> FEATURE:
<221> NAME/KEY: MOD_RES
<222> LOCATION: (7)..(7)
<223> OTHER INFORMATION: D-Arg

<400> SEQUENCE: 166

Arg Trp Met Tyr Trp Gln Arg
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:

```
<221> NAME/KEY: MOD_RES
<222> LOCATION: (7)..(7)
<223> OTHER INFORMATION: D-Ala

<400> SEQUENCE: 167

Phe Trp Arg Trp His Arg Ala
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Met
<220> FEATURE:
<221> NAME/KEY: MOD_RES
<222> LOCATION: (4)..(4)
<223> OTHER INFORMATION: D-Gln
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 168

Arg Gln Met Gln Tyr Arg Arg
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
```

<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 169

Phe Trp Ala Trp His Arg Arg
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 170

Arg Phe Tyr Arg His His Arg
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)

```
<223> OTHER INFORMATION: D-His
<220> FEATURE:
<221> NAME/KEY: MOD_RES
<222> LOCATION: (6)..(6)
<223> OTHER INFORMATION: D-Ala
<220> FEATURE:
<221> NAME/KEY: MOD_RES
<222> LOCATION: (7)..(7)
<223> OTHER INFORMATION: D-Arg

<400> SEQUENCE: 171

Phe Trp Arg Trp His Ala Arg
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 172

His Trp Arg Trp Arg Trp Arg
1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Arg
```

```
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Gln
<220> FEATURE:
<221> NAME/KEY: MOD_RES
<222> LOCATION: (7)..(7)
<223> OTHER INFORMATION: D-Arg

<400> SEQUENCE: 173

Lys Arg Trp Arg His Gln Arg
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 174

Trp Trp Arg Arg His His Arg
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Trp
<220> FEATURE:
```

```
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 175

Lys Gln Trp Tyr His Trp Arg
1               5

<210> SEQ ID NO 176
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 176

Ala Trp Arg Trp His Arg Arg
1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
```

```
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 177

Phe Ala Arg Trp His Arg Arg
1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 178

Phe Trp Arg Ala His Arg Arg
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
```

```
<223> OTHER INFORMATION: D-Gln
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 179

Arg Gln His Tyr His Trp Arg
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Ser
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 180

Ser Trp Arg Trp His His Arg
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Ser
```

```
<220> FEATURE:
<221> NAME/KEY: MOD_RES
<222> LOCATION: (2)..(2)
<223> OTHER INFORMATION: D-His
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 181

Ser His Trp Arg Arg His Arg
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Gln
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Gln
<220> FEATURE:
<221> NAME/KEY: MOD_RES
<222> LOCATION: (7)..(7)
<223> OTHER INFORMATION: D-Ser

<400> SEQUENCE: 182

Tyr Trp Gln Trp Arg Gln Ser
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Gln
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Gln
<220> FEATURE:
<221> NAME/KEY: MOD_RES
<222> LOCATION: (7)..(7)
<223> OTHER INFORMATION: D-Arg

<400> SEQUENCE: 183

Tyr Gln Trp Gln Tyr Gln Arg
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Ala
<220> FEATURE:
<221> NAME/KEY: MOD_RES
<222> LOCATION: (7)..(7)
<223> OTHER INFORMATION: D-Ala

<400> SEQUENCE: 184

Phe Trp Arg Trp His Ala Ala
1               5

<210> SEQ ID NO 185
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Arg

<400> SEQUENCE: 185

Trp Trp Arg Phe His Trp Arg
1               5

<210> SEQ ID NO 186
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Trp

<400> SEQUENCE: 186

Arg Leu Lys Trp Arg Trp
1               5

<210> SEQ ID NO 187
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: D-Gln
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-His

<400> SEQUENCE: 187

Gln Leu Lys Trp Leu His
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 188

Phe Ala Arg Ala His Arg Arg
1               5

<210> SEQ ID NO 189
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Trp

<400> SEQUENCE: 189

Lys Leu Lys Trp Leu Trp
1               5

<210> SEQ ID NO 190
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Ile
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Trp

<400> SEQUENCE: 190

Ile Leu Lys Trp Leu Trp
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Ser
<220> FEATURE:
```

```
<221> NAME/KEY: MOD_RES
<222> LOCATION: (2)..(2)
<223> OTHER INFORMATION: D-His
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 191

Ser His Trp Arg His His Arg
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Gln

<400> SEQUENCE: 192

Arg Gln Trp Tyr Arg Trp Gln
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: D-Gln
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 193

Gln Trp Arg Trp Arg His Arg
1               5

<210> SEQ ID NO 194
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Gln
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Lys
<220> FEATURE:
<221> NAME/KEY: MOD_RES
<222> LOCATION: (7)..(7)
<223> OTHER INFORMATION: D-Asn

<400> SEQUENCE: 194

Gln Val Arg Tyr His Lys Asn
1               5

<210> SEQ ID NO 195
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Gln
<220> FEATURE:
<221> NAME/KEY: MOD_RES
<222> LOCATION: (6)..(6)
<223> OTHER INFORMATION: D-Trp

<400> SEQUENCE: 195

Lys Leu Lys Trp Gln Trp
1               5

<210> SEQ ID NO 196
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Leu
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (6)..(6)
<223> OTHER INFORMATION: D-Tyr

<400> SEQUENCE: 196

Lys Leu Lys Trp Ala Tyr
1               5

<210> SEQ ID NO 197
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
```

```
<220> FEATURE:
<221> NAME/KEY: MOD_RES
<222> LOCATION: (2)..(2)
<223> OTHER INFORMATION: D-Met
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 197

Arg Met Trp Arg His His Arg
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Gln
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg

<400> SEQUENCE: 198

Gln Phe His Tyr Lys Arg Arg
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Arg

<400> SEQUENCE: 199

Arg Phe His Arg His His Arg
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Gln
<220> FEATURE:
<221> NAME/KEY: MOD_RES
<222> LOCATION: (5)..(5)
<223> OTHER INFORMATION: D-Tyr
<220> FEATURE:
<221> NAME/KEY: MOD_RES
<222> LOCATION: (6)..(6)
<223> OTHER INFORMATION: D-Gln
<220> FEATURE:
<221> NAME/KEY: MOD_RES
<222> LOCATION: (7)..(7)
<223> OTHER INFORMATION: D-Arg

<400> SEQUENCE: 200

His Gln Arg Gln Tyr Gln Arg
1               5

<210> SEQ ID NO 201
<211> LENGTH: 7
<212> TYPE: PRT
<213> ORGANISM: Artificial Sequence
```

-continued

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is D-Arg, D-His, D-Leu, D-Ile, D-Lys,
      D-Tyr, D-Ser, D-Trp, D-Ala, D-Gln or D-Phe
<220> FEATURE:
<221> NAME/KEY: MISC_FEATURE
<222> LOCATION: (2)..(2)
<223> OTHER INFORMATION: Xaa is D-Phe, D-Arg, D-His, D-Leu, D-Ile,
      D-Val, D-Met, D-Tyr, D-Ala, D-Gln or D-Trp
<220> FEATURE:
<221> NAME/KEY: MISC_FEATURE
<222> LOCATION: (3)..(3)
<223> OTHER INFORMATION: Xaa is D-Arg, D-Lys, D-His, D-Met, D-Ala,
      D-Gln, D-Glu, D-Trp or D-Tyr
<220> FEATURE:
<221> NAME/KEY: MISC_FEATURE
<222> LOCATION: (4)..(4)
<223> OTHER INFORMATION: Xaa is D-Arg, D-Lys, D-His, D-Ala, D-Ile,
      D-Met, D-Gln, D-Trp, D-Phe or D-Tyr
<220> FEATURE:
<221> NAME/KEY: MISC_FEATURE
<222> LOCATION: (5)..(5)
<223> OTHER INFORMATION: Xaa is D-His, D-Arg, D-Lys, D-Ala, D-Leu,
      D-Gln, D-Trp, D-Phe or D-Tyr
<220> FEATURE:
<221> NAME/KEY: MISC_FEATURE
<222> LOCATION: (6)..(6)
<223> OTHER INFORMATION: Xaa is D-Arg, D-Gln, D-Ala, D-Lys, D-Tyr, D-Trp
      or D-His
<220> FEATURE:
<221> NAME/KEY: MISC_FEATURE
<222> LOCATION: (7)..(7)
<223> OTHER INFORMATION: Xaa is D-Arg, D-Lys, D-Ala, D-Asn, D-Gln,
      D-Ser, D-His or is absent

<400> SEQUENCE: 201

Xaa Xaa Xaa Xaa Xaa Xaa Xaa
1               5

<210> SEQ ID NO 202
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: Xaa is Ile, Leu, Arg, Ala, Trp, Phe, Thr, Chg,
      Tyr, D-Arg, D-His, D-Leu, D-Ile, D-Lys, D-Tyr, D-Ser, D-Trp,
      D-Ala, D-Gln or D-Phe
<220> FEATURE:
<221> NAME/KEY: MISC_FEATURE
<222> LOCATION: (20)..(20)
<223> OTHER INFORMATION: Xaa is Arg, homo-Arg, Phe, Trp, Gln, His, Ser,
      Thr, Val, Leu, Ala, Tyr, D-Phe, D-Arg, D-His, D-Leu, D-Ile, D-Val,
      D-Met, D-Tyr, D-Ala, D-Gln or D-Trp
<220> FEATURE:
<221> NAME/KEY: MISC_FEATURE
<222> LOCATION: (21)..(21)
<223> OTHER INFORMATION: Xaa is Chg, Ile, N-Me-Ile, Arg, Tyr, Lys, Val,
      Phe, Phg, Ala, Leu, D-Arg, D-Lys, D-His, D-Met, D-Ala, D-Gln,
      D-Glu, D-Trp or D-Tyr
<220> FEATURE:
<221> NAME/KEY: MISC_FEATURE
<222> LOCATION: (22)..(22)
<223> OTHER INFORMATION: Xaa is N-Me-Lys, homo-Arg, Arg, Lys, Glu, Met,
      Gln, Ile, Leu, Ala, Phe, Tyr, D-Arg, D-Lys, D-His, D-Ala, D-Ile,
      D-Met, D-Gln, D-Trp, D-Phe or D-Tyr
<220> FEATURE:
<221> NAME/KEY: MISC_FEATURE
<222> LOCATION: (23)..(23)
<223> OTHER INFORMATION: Xaa is His, Arg, Lys, Gln, Tyr, Thr, Ile, Leu,
      Ala, Phe, D-His, D-Arg, D-Lys, D-Ala, D-Leu, D-Gln, D-Trp, D-Phe
```

```
         or D-Tyr
<220> FEATURE:
<221> NAME/KEY: MISC_FEATURE
<222> LOCATION: (24)..(24)
<223> OTHER INFORMATION: Xaa is Tyr, Thr, Ala, Gln, Leu, Val, His, Lys,
      Arg, Trp, Phe, D-Arg, D-Gln, D-Ala, D-Lys, D-Tyr, D-Trp or D-His
<220> FEATURE:
<221> NAME/KEY: MISC_FEATURE
<222> LOCATION: (25)..(25)
<223> OTHER INFORMATION: Xaa is Arg, Ala, His, Thr, Ser, Glu, Lys,
      D-Arg, D-Lys, D-Ala, D-Asn, D-Gln, D-Ser, D-His or is absent
<220> FEATURE:
<221> NAME/KEY: MISC_FEATURE
<222> LOCATION: (26)..(26)
<223> OTHER INFORMATION: Xaa is Pro or is absent

<400> SEQUENCE: 202

Arg Arg Arg Arg Arg Arg Arg Arg Arg Arg Arg Arg Arg Arg Arg
1               5                   10                  15

Pro Ile Xaa Xaa Xaa Xaa Xaa Xaa Xaa Xaa
            20                  25

<210> SEQ ID NO 203
<211> LENGTH: 19
<212> TYPE: PRT
<213> ORGANISM: Artificial Sequence
<220> FEATURE:
<223> OTHER INFORMATION: Synthetic peptide

<400> SEQUENCE: 203

Arg Arg Arg Arg Arg Arg Arg Arg Arg Arg Pro Ile Ile Arg Ile Arg
1               5                   10                  15

His Tyr Arg

<210> SEQ ID NO 204
<211> LENGTH: 19
<212> TYPE: PRT
<213> ORGANISM: Artificial Sequence
<220> FEATURE:
<223> OTHER INFORMATION: Synthetic peptide

<400> SEQUENCE: 204

Arg Arg Arg Arg Arg Arg Arg Arg Arg Arg Pro Ile Ile Arg Ile Arg
1               5                   10                  15

His Tyr Pro

<210> SEQ ID NO 205
<211> LENGTH: 21
<212> TYPE: PRT
<213> ORGANISM: Artificial Sequence
<220> FEATURE:
<223> OTHER INFORMATION: Synthetic peptide

<400> SEQUENCE: 205

Pro Arg Arg Arg Arg Arg Arg Arg Arg Arg Arg Pro Ile Ile Arg Ile
1               5                   10                  15

Arg His Tyr Arg Pro
            20

<210> SEQ ID NO 206
<211> LENGTH: 20
<212> TYPE: PRT
<213> ORGANISM: Artificial Sequence
<220> FEATURE:
<223> OTHER INFORMATION: Synthetic peptide

<400> SEQUENCE: 206
```

Arg Arg Arg Arg Arg Arg Arg Arg Arg Pro Ile Ile Arg Ile Arg
1               5                   10                  15

His Tyr Arg Pro
            20

<210> SEQ ID NO 207
<211> LENGTH: 21
<212> TYPE: PRT
<213> ORGANISM: Artificial Sequence
<220> FEATURE:
<223> OTHER INFORMATION: Synthetic peptide

<400> SEQUENCE: 207

Pro Arg Arg Arg Arg Arg Arg Arg Arg Arg Pro Ile Leu Arg Ile
1               5                   10                  15

Arg Tyr Trp Lys Pro
            20

<210> SEQ ID NO 208
<211> LENGTH: 21
<212> TYPE: PRT
<213> ORGANISM: Artificial Sequence
<220> FEATURE:
<223> OTHER INFORMATION: Synthetic peptide

<400> SEQUENCE: 208

Pro Arg Arg Arg Arg Arg Arg Arg Arg Arg Pro Ile Thr Arg Ile
1               5                   10                  15

Arg Phe Tyr Arg Pro
            20

<210> SEQ ID NO 209
<211> LENGTH: 21
<212> TYPE: PRT
<213> ORGANISM: Artificial Sequence
<220> FEATURE:
<223> OTHER INFORMATION: Synthetic peptide

<400> SEQUENCE: 209

Pro Arg Arg Arg Arg Arg Arg Arg Arg Arg Pro Ile Trp Thr Ile
1               5                   10                  15

Lys Leu Trp His Pro
            20

<210> SEQ ID NO 210
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (13)..(13)
<223> OTHER INFORMATION: D-Gln
<220> FEATURE:
<221> NAME/KEY: MOD_RES
<222> LOCATION: (14)..(14)
<223> OTHER INFORMATION: D-Gln
<220> FEATURE:
<221> NAME/KEY: MOD_RES
<222> LOCATION: (15)..(15)
<223> OTHER INFORMATION: D-Arg
<220> FEATURE:
<221> NAME/KEY: MOD_RES
<222> LOCATION: (16)..(16)
<223> OTHER INFORMATION: D-Tyr
<220> FEATURE:

-continued

```
<221> NAME/KEY: MOD_RES
<222> LOCATION: (17)..(17)
<223> OTHER INFORMATION: D-Tyr
<220> FEATURE:
<221> NAME/KEY: MOD_RES
<222> LOCATION: (18)..(18)
<223> OTHER INFORMATION: D-Trp
<220> FEATURE:
<221> NAME/KEY: MOD_RES
<222> LOCATION: (19)..(19)
<223> OTHER INFORMATION: D-Arg

<400> SEQUENCE: 210

Arg Arg Arg Arg Arg Arg Arg Arg Arg Arg Pro Ile Gln Gln Arg Tyr
1               5                   10                  15

Tyr Trp Arg

<210> SEQ ID NO 211
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (13)..(13)
<223> OTHER INFORMATION: D-Tyr
<220> FEATURE:
<221> NAME/KEY: MOD_RES
<222> LOCATION: (14)..(14)
<223> OTHER INFORMATION: D-Gln
<220> FEATURE:
<221> NAME/KEY: MOD_RES
<222> LOCATION: (15)..(15)
<223> OTHER INFORMATION: D-Trp
<220> FEATURE:
<221> NAME/KEY: MOD_RES
<222> LOCATION: (16)..(16)
<223> OTHER INFORMATION: D-
<220> FEATURE:
<221> NAME/KEY: MOD_RES
<222> LOCATION: (17)..(17)
<223> OTHER INFORMATION: D-Arg
<220> FEATURE:
<221> NAME/KEY: MOD_RES
<222> LOCATION: (18)..(18)
<223> OTHER INFORMATION: D-Trp
<220> FEATURE:
<221> NAME/KEY: MOD_RES
<222> LOCATION: (19)..(19)
<223> OTHER INFORMATION: D-Gln

<400> SEQUENCE: 211

Arg Arg Arg Arg Arg Arg Arg Arg Arg Arg Pro Ile Tyr Gln Trp Tyr
1               5                   10                  15

Arg Trp Gln

<210> SEQ ID NO 212
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (13)..(13)
<223> OTHER INFORMATION: D-Lys
<220> FEATURE:
<221> NAME/KEY: MOD_RES
<222> LOCATION: (14)..(14)
<223> OTHER INFORMATION: D-Phe
<220> FEATURE:
<221> NAME/KEY: MOD_RES
```

<222> LOCATION: (15)..(15)
<223> OTHER INFORMATION: D-Arg
<220> FEATURE:
<221> NAME/KEY: MOD_RES
<222> LOCATION: (16)..(16)
<223> OTHER INFORMATION: D-Phe
<220> FEATURE:
<221> NAME/KEY: MOD_RES
<222> LOCATION: (17)..(17)
<223> OTHER INFORMATION: D-Tyr
<220> FEATURE:
<221> NAME/KEY: MOD_RES
<222> LOCATION: (18)..(18)
<223> OTHER INFORMATION: D-His
<220> FEATURE:
<221> NAME/KEY: MOD_RES
<222> LOCATION: (19)..(19)
<223> OTHER INFORMATION: D-Arg

<400> SEQUENCE: 212

Arg Arg Arg Arg Arg Arg Arg Arg Arg Arg Pro Ile Lys Phe Arg Phe
1               5                   10                  15

Tyr His Arg

<210> SEQ ID NO 213
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: D-Phe
<220> FEATURE:
<221> NAME/KEY: MOD_RES
<222> LOCATION: (15)..(15)
<223> OTHER INFORMATION: D-Tyr
<220> FEATURE:
<221> NAME/KEY: MOD_RES
<222> LOCATION: (16)..(16)
<223> OTHER INFORMATION: D-Tyr
<220> FEATURE:
<221> NAME/KEY: MOD_RES
<222> LOCATION: (17)..(17)
<223> OTHER INFORMATION: D-His
<220> FEATURE:
<221> NAME/KEY: MOD_RES
<222> LOCATION: (18)..(18)
<223> OTHER INFORMATION: D-Arg
<220> FEATURE:
<221> NAME/KEY: MOD_RES
<222> LOCATION: (19)..(19)
<223> OTHER INFORMATION: D-Arg

<400> SEQUENCE: 213

Arg Arg Arg Arg Arg Arg Arg Arg Arg Arg Pro Ile Arg Phe Tyr Tyr
1               5                   10                  15

His Arg Arg

<210> SEQ ID NO 214
<211> LENGTH: 11
<212> TYPE: PRT
<213> ORGANISM: Artificial Sequence
<220> FEATURE:
<223> OTHER INFORMATION: Synthetic peptide

<400> SEQUENCE: 214

```
Tyr Ala Arg Ala Ala Ala Arg Gln Ala Arg Ala
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Synthetic peptide

<400> SEQUENCE: 215

Tyr Gly Arg Lys Lys Arg Arg
1               5

<210> SEQ ID NO 216
<211> LENGTH: 11
<212> TYPE: PRT
<213> ORGANISM: Artificial Sequence
<220> FEATURE:
<223> OTHER INFORMATION: Synthetic peptide

<400> SEQUENCE: 216

Tyr Gly Arg Lys Lys Arg Arg Gln Arg Arg Arg
1               5                   10

<210> SEQ ID NO 217
<211> LENGTH: 5
<212> TYPE: PRT
<213> ORGANISM: Artificial Sequence
<220> FEATURE:
<223> OTHER INFORMATION: Synthetic peptide

<400> SEQUENCE: 217

Arg Arg Gln Arg Arg
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetic peptide

<400> SEQUENCE: 218

Ile Arg Tyr Arg Arg Tyr Arg
1               5

<210> SEQ ID NO 219
<211> LENGTH: 7
<212> TYPE: PRT
<213> ORGANISM: Artificial Sequence
<220> FEATURE:
<223> OTHER INFORMATION: Synthetic peptide

<400> SEQUENCE: 219

Tyr Arg Ile Arg Arg Tyr Arg
1               5

<210> SEQ ID NO 220
<211> LENGTH: 7
<212> TYPE: PRT
<213> ORGANISM: Artificial Sequence
<220> FEATURE:
<223> OTHER INFORMATION: Synthetic peptide

<400> SEQUENCE: 220

Ala Arg Ala Arg Arg Tyr Arg
```

```
1               5

<210> SEQ ID NO 221
<211> LENGTH: 7
<212> TYPE: PRT
<213> ORGANISM: Artificial Sequence
<220> FEATURE:
<223> OTHER INFORMATION: Synthetic peptide

<400> SEQUENCE: 221

Ile Arg Ile Ala Ala Tyr Arg
1               5

<210> SEQ ID NO 222
<211> LENGTH: 7
<212> TYPE: PRT
<213> ORGANISM: Artificial Sequence
<220> FEATURE:
<223> OTHER INFORMATION: Synthetic peptide

<400> SEQUENCE: 222

Ile Arg Ile Ala Arg Ala Arg
1               5

<210> SEQ ID NO 223
<211> LENGTH: 7
<212> TYPE: PRT
<213> ORGANISM: Artificial Sequence
<220> FEATURE:
<223> OTHER INFORMATION: Synthetic peptide

<400> SEQUENCE: 223

Ile Arg Ile Ala Arg Tyr Ala
1               5

<210> SEQ ID NO 224
<211> LENGTH: 7
<212> TYPE: PRT
<213> ORGANISM: Artificial Sequence
<220> FEATURE:
<223> OTHER INFORMATION: Synthetic peptide

<400> SEQUENCE: 224

Ile Arg Ile Arg Ala Tyr Ala
1               5

<210> SEQ ID NO 225
<211> LENGTH: 7
<212> TYPE: PRT
<213> ORGANISM: Artificial Sequence
<220> FEATURE:
<223> OTHER INFORMATION: Synthetic peptide

<400> SEQUENCE: 225

Leu Thr Ile Ile Thr Leu Glu
1               5

<210> SEQ ID NO 226
<211> LENGTH: 10
<212> TYPE: PRT
<213> ORGANISM: Artificial Sequence
<220> FEATURE:
<223> OTHER INFORMATION: Synthetic peptide

<400> SEQUENCE: 226

Arg Pro Ile Leu Ile Ile Val Thr Leu Glu
1               5                   10
```

<210> SEQ ID NO 227
<211> LENGTH: 10
<212> TYPE: PRT
<213> ORGANISM: Artificial Sequence
<220> FEATURE:
<223> OTHER INFORMATION: Synthetic peptide

<400> SEQUENCE: 227

Arg Pro Ile Leu Ile Ile Ile Thr Leu Glu
1               5                   10

<210> SEQ ID NO 228
<211> LENGTH: 10
<212> TYPE: PRT
<213> ORGANISM: Artificial Sequence
<220> FEATURE:
<223> OTHER INFORMATION: Synthetic peptide

<400> SEQUENCE: 228

Arg Pro Ile Leu Thr Ile Ile Thr Leu Glu
1               5                   10

<210> SEQ ID NO 229
<211> LENGTH: 19
<212> TYPE: PRT
<213> ORGANISM: Artificial Sequence
<220> FEATURE:
<223> OTHER INFORMATION: Synthetic peptide

<400> SEQUENCE: 229

Arg Arg Arg Arg Arg Arg Arg Arg Arg Arg Pro Ile Leu Thr Arg Ile
1               5                   10                  15

Thr Leu Glu

<210> SEQ ID NO 230
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Pro
<220> FEATURE:
<221> NAME/KEY: MOD_RES
<222> LOCATION: (12)..(12)
<223> OTHER INFORMATION: D-Ile
<220> FEATURE:
<221> NAME/KEY: MOD_RES
<222> LOCATION: (13)..(13)
<223> OTHER INFORMATION: D-Tyr
<220> FEATURE:
<221> NAME/KEY: MOD_RES
<222> LOCATION: (14)..(14)
<223> OTHER INFORMATION: D-Gln
<220> FEATURE:
<221> NAME/KEY: MOD_RES
<222> LOCATION: (15)..(15)
<223> OTHER INFORMATION: D-Trp
<220> FEATURE:
<221> NAME/KEY: MOD_RES
<222> LOCATION: (16)..(16)
<223> OTHER INFORMATION: D-Tyr
<220> FEATURE:
<221> NAME/KEY: MOD_RES
<222> LOCATION: (17)..(17)
<223> OTHER INFORMATION: D-Arg
<220> FEATURE:
<221> NAME/KEY: MOD_RES
<222> LOCATION: (18)..(18)
<223> OTHER INFORMATION: D-Trp
<220> FEATURE:
<221> NAME/KEY: MOD_RES
<222> LOCATION: (19)..(19)
<223> OTHER INFORMATION: D-Gln

<400> SEQUENCE: 230

Arg Arg Arg Arg Arg Arg Arg Arg Arg Arg Pro Ile Tyr Gln Trp Tyr
1               5                   10                  15

Arg Trp Gln

<210> SEQ ID NO 231
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES

```
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Gly
<220> FEATURE:
<221> NAME/KEY: MOD_RES
<222> LOCATION: (11)..(11)
<223> OTHER INFORMATION: D-Gly
<220> FEATURE:
<221> NAME/KEY: MOD_RES
<222> LOCATION: (12)..(12)
<223> OTHER INFORMATION: D-Gly
<220> FEATURE:
<221> NAME/KEY: MOD_RES
<222> LOCATION: (13)..(13)
<223> OTHER INFORMATION: D-Tyr
<220> FEATURE:
<221> NAME/KEY: MOD_RES
<222> LOCATION: (14)..(14)
<223> OTHER INFORMATION: D-Gln
<220> FEATURE:
<221> NAME/KEY: MOD_RES
<222> LOCATION: (15)..(15)
<223> OTHER INFORMATION: D-Trp
<220> FEATURE:
<221> NAME/KEY: MOD_RES
<222> LOCATION: (16)..(16)
<223> OTHER INFORMATION: D-Tyr
<220> FEATURE:
<221> NAME/KEY: MOD_RES
<222> LOCATION: (17)..(17)
<223> OTHER INFORMATION: D-Arg
<220> FEATURE:
<221> NAME/KEY: MOD_RES
<222> LOCATION: (18)..(18)
<223> OTHER INFORMATION: D-Trp
<220> FEATURE:
<221> NAME/KEY: MOD_RES
<222> LOCATION: (19)..(19)
<223> OTHER INFORMATION: D-Gln

<400> SEQUENCE: 231

Arg Arg Arg Arg Arg Arg Arg Arg Gly Gly Gly Tyr Gln Trp Tyr
1               5                   10                  15

Arg Trp Gln

<210> SEQ ID NO 232
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
```

```
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Pro
<220> FEATURE:
<221> NAME/KEY: MOD_RES
<222> LOCATION: (12)..(12)
<223> OTHER INFORMATION: D-Ile
<220> FEATURE:
<221> NAME/KEY: MOD_RES
<222> LOCATION: (13)..(13)
<223> OTHER INFORMATION: D-Lys
<220> FEATURE:
<221> NAME/KEY: MOD_RES
<222> LOCATION: (14)..(14)
<223> OTHER INFORMATION: D-Phe
<220> FEATURE:
<221> NAME/KEY: MOD_RES
<222> LOCATION: (15)..(15)
<223> OTHER INFORMATION: D-Arg
<220> FEATURE:
<221> NAME/KEY: MOD_RES
<222> LOCATION: (16)..(16)
<223> OTHER INFORMATION: D-Phe
<220> FEATURE:
<221> NAME/KEY: MOD_RES
<222> LOCATION: (17)..(17)
<223> OTHER INFORMATION: D-Tyr
<220> FEATURE:
<221> NAME/KEY: MOD_RES
<222> LOCATION: (18)..(18)
<223> OTHER INFORMATION: D-His
<220> FEATURE:
<221> NAME/KEY: MOD_RES
<222> LOCATION: (19)..(19)
<223> OTHER INFORMATION: D-Arg

<400> SEQUENCE: 232

Arg Arg Arg Arg Arg Arg Arg Arg Arg Pro Ile Lys Phe Arg Phe
1               5                   10                  15

Tyr His Arg
```

```
<210> SEQ ID NO 233
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Pro
<220> FEATURE:
<221> NAME/KEY: MOD_RES
<222> LOCATION: (12)..(12)
<223> OTHER INFORMATION: D-Ile
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: D-Ile
<220> FEATURE:
<221> NAME/KEY: MOD_RES
<222> LOCATION: (15)..(15)
<223> OTHER INFORMATION: D-His
<220> FEATURE:
<221> NAME/KEY: MOD_RES
<222> LOCATION: (16)..(16)
<223> OTHER INFORMATION: D-Tyr
<220> FEATURE:
<221> NAME/KEY: MOD_RES
<222> LOCATION: (17)..(17)
<223> OTHER INFORMATION: D-Phe
<220> FEATURE:
<221> NAME/KEY: MOD_RES
<222> LOCATION: (18)..(18)
<223> OTHER INFORMATION: D-Arg
<220> FEATURE:
```

<221> NAME/KEY: MOD_RES
<222> LOCATION: (19)..(19)
<223> OTHER INFORMATION: D-Arg

<400> SEQUENCE: 233

Arg Arg Arg Arg Arg Arg Arg Arg Arg Arg Pro Ile Arg Ile His Tyr
1               5                   10                  15

Phe Arg Arg

<210> SEQ ID NO 234
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Pro
<220> FEATURE:
<221> NAME/KEY: MOD_RES
<222> LOCATION: (12)..(12)
<223> OTHER INFORMATION: D-Ile
<220> FEATURE:
<221> NAME/KEY: MOD_RES
<222> LOCATION: (13)..(13)
<223> OTHER INFORMATION: D-Lys
<220> FEATURE:
<221> NAME/KEY: MOD_RES
<222> LOCATION: (14)..(14)
<223> OTHER INFORMATION: D-Trp
<220> FEATURE:
<221> NAME/KEY: MOD_RES
<222> LOCATION: (15)..(15)
<223> OTHER INFORMATION: D-Arg
<220> FEATURE:

```
<221> NAME/KEY: MOD_RES
<222> LOCATION: (16)..(16)
<223> OTHER INFORMATION: D-Trp
<220> FEATURE:
<221> NAME/KEY: MOD_RES
<222> LOCATION: (17)..(17)
<223> OTHER INFORMATION: D-Tyr
<220> FEATURE:
<221> NAME/KEY: MOD_RES
<222> LOCATION: (18)..(18)
<223> OTHER INFORMATION: D-Arg
<220> FEATURE:
<221> NAME/KEY: MOD_RES
<222> LOCATION: (19)..(19)
<223> OTHER INFORMATION: D-Arg

<400> SEQUENCE: 234

Arg Arg Arg Arg Arg Arg Arg Arg Arg Arg Pro Ile Lys Trp Arg Trp
1               5                   10                  15

Tyr Arg Arg

<210> SEQ ID NO 235
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Pro
<220> FEATURE:
<221> NAME/KEY: MOD_RES
<222> LOCATION: (12)..(12)
<223> OTHER INFORMATION: D-Ile
<220> FEATURE:
```

<221> NAME/KEY: MOD_RES
<222> LOCATION: (13)..(13)
<223> OTHER INFORMATION: D-His
<220> FEATURE:
<221> NAME/KEY: MOD_RES
<222> LOCATION: (14)..(14)
<223> OTHER INFORMATION: D-Leu
<220> FEATURE:
<221> NAME/KEY: MOD_RES
<222> LOCATION: (15)..(15)
<223> OTHER INFORMATION: D-Arg
<220> FEATURE:
<221> NAME/KEY: MOD_RES
<222> LOCATION: (16)..(16)
<223> OTHER INFORMATION: D-Ile
<220> FEATURE:
<221> NAME/KEY: MOD_RES
<222> LOCATION: (17)..(17)
<223> OTHER INFORMATION: D-Trp
<220> FEATURE:
<221> NAME/KEY: MOD_RES
<222> LOCATION: (18)..(18)
<223> OTHER INFORMATION: D-Arg
<220> FEATURE:
<221> NAME/KEY: MOD_RES
<222> LOCATION: (19)..(19)
<223> OTHER INFORMATION: D-Asn

<400> SEQUENCE: 235

Arg Arg Arg Arg Arg Arg Arg Arg Arg Pro Ile His Leu Arg Ile
1               5                   10                  15

Trp Arg Asn

<210> SEQ ID NO 236
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:

```
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Pro
<220> FEATURE:
<221> NAME/KEY: MOD_RES
<222> LOCATION: (12)..(12)
<223> OTHER INFORMATION: D-Ile
<220> FEATURE:
<221> NAME/KEY: MOD_RES
<222> LOCATION: (13)..(13)
<223> OTHER INFORMATION: D-His
<220> FEATURE:
<221> NAME/KEY: MOD_RES
<222> LOCATION: (14)..(14)
<223> OTHER INFORMATION: D-Gln
<220> FEATURE:
<221> NAME/KEY: MOD_RES
<222> LOCATION: (15)..(15)
<223> OTHER INFORMATION: D-Arg
<220> FEATURE:
<221> NAME/KEY: MOD_RES
<222> LOCATION: (16)..(16)
<223> OTHER INFORMATION: D-Gln
<220> FEATURE:
<221> NAME/KEY: MOD_RES
<222> LOCATION: (17)..(17)
<223> OTHER INFORMATION: D-Tyr
<220> FEATURE:
<221> NAME/KEY: MOD_RES
<222> LOCATION: (18)..(18)
<223> OTHER INFORMATION: D-Gln
<220> FEATURE:
<221> NAME/KEY: MOD_RES
<222> LOCATION: (19)..(19)
<223> OTHER INFORMATION: D-Arg

<400> SEQUENCE: 236

Arg Arg Arg Arg Arg Arg Arg Arg Arg Pro Ile His Gln Arg Gln
1               5                   10                  15

Tyr Gln Arg

<210> SEQ ID NO 237
<211> LENGTH: 7
<212> TYPE: PRT
<213> ORGANISM: Artificial Sequence
<220> FEATURE:
<223> OTHER INFORMATION: Synthetic peptide

<400> SEQUENCE: 237

Trp Thr Arg Ile Thr Leu Glu
1               5

<210> SEQ ID NO 238
<211> LENGTH: 7
<212> TYPE: PRT
<213> ORGANISM: Artificial Sequence
<220> FEATURE:
<223> OTHER INFORMATION: Synthetic peptide

<400> SEQUENCE: 238

Leu Thr Arg Ile Thr Leu Glu
1               5

<210> SEQ ID NO 239
<211> LENGTH: 26
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(16)
<223> OTHER INFORMATION: d-Arg
<220> FEATURE:
<221> NAME/KEY: MISC_FEATURE
<222> LOCATION: (19)..(19)
<223> OTHER INFORMATION: Xaa is Ile, Leu, Arg, Ala, Trp, Phe, Thr, Chg,
      Tyr, D-Arg, D-His, D-Leu, D-Ile, D-Lys, D-Tyr, D-Ser, D-Trp,
      D-Ala, D-Gln or D-Phe
<220> FEATURE:
<221> NAME/KEY: MISC_FEATURE
<222> LOCATION: (20)..(20)
<223> OTHER INFORMATION: Xaa is Arg, homo-Arg, Phe, Trp, Gln, His, Ser,
      Thr, Val, Leu, Ala, Tyr, D-Phe, D-Arg, D-His, D-Leu, D-Ile, D-Val,
      D-Met, D-Tyr, D-Ala, D-Gln or D-Trp
<220> FEATURE:
<221> NAME/KEY: MISC_FEATURE
<222> LOCATION: (21)..(21)
<223> OTHER INFORMATION: Xaa is Chg, Ile, N-Me-Ile, Arg, Tyr, Lys, Val,
      Phe, Phg, Ala, Leu, D-Arg, D-Lys, D-His, D-Met, D-Ala, D-Gln,
      D-Glu, D-Trp or D-Tyr
<220> FEATURE:
<221> NAME/KEY: MISC_FEATURE
<222> LOCATION: (22)..(22)
<223> OTHER INFORMATION: Xaa is N-Me-Lys, homo-Arg, Arg, Lys, Glu, Met,
      Gln, Ile, Leu, Ala, Phe, Tyr, D-Arg, D-Lys, D-His, D-Ala, D-Ile,
      D-Met, D-Gln, D-Trp, D-Phe or D-Tyr
<220> FEATURE:
<221> NAME/KEY: MISC_FEATURE
<222> LOCATION: (23)..(23)
<223> OTHER INFORMATION: Xaa is His, Arg, Lys, Gln, Tyr, Thr, Ile, Leu,
      Ala, Phe, D-His, D-Arg, D-Lys, D-Ala, D-Leu, D-Gln, D-Trp, D-Phe
      or D-Tyr
<220> FEATURE:
<221> NAME/KEY: MISC_FEATURE
<222> LOCATION: (24)..(24)
<223> OTHER INFORMATION: Xaa is Tyr, Thr, Ala, Gln, Leu, Val, His, Lys,
      Arg, Trp, Phe, D-Arg, D-Gln, D-Ala, D-Lys, D-Tyr, D-Trp or D-His
<220> FEATURE:
<221> NAME/KEY: MISC_FEATURE
<222> LOCATION: (25)..(25)
<223> OTHER INFORMATION: Xaa is Arg, Ala, His, Thr, Ser, Glu, Lys,
      D-Arg, D-Lys, D-Ala, D-Asn, D-Gln, D-Ser, D-His or is absent
<220> FEATURE:
<221> NAME/KEY: MISC_FEATURE
<222> LOCATION: (26)..(26)
<223> OTHER INFORMATION: Xaa is Pro or is absent

<400> SEQUENCE: 239

Arg Arg Arg Arg Arg Arg Arg Arg Arg Arg Arg Arg Arg Arg Arg Arg
1               5                   10                  15

Pro Ile Xaa Xaa Xaa Xaa Xaa Xaa Xaa Xaa
            20                  25
```

PEPTIDE INHIBITORS OF TRANSCRIPTION FACTOR AGGREGATION

CROSS-REFERENCE TO RELATED APPLICATIONS

This application is a U.S. National Phase of International Patent Application No. PCT/US2018/019417, filed Feb. 23, 2018, which claims the benefit of U.S. Provisional Application No. 62/462,815, filed on Feb. 23, 2017.

INCORPORATION BY REFERENCE OF MATERIAL SUBMITTED ELECTRONICALLY

This application includes and incorporates by reference the contents of a Sequence Listing, submitted to the U.S. Patent and Trademark Office as a text file named "51539A_Seqlisting.txt," which was created on Aug. 19, 2019, and which is 92,128 bytes in size.

FIELD OF THE INVENTION

This invention relates to the field of transcription factors, for example p53, p63 and p73. More specifically, the invention relates to cancer chemotherapeutics that modulate the activity of a transcription factor, e.g., by modulating aggregation of the transcription factor. More specifically, the invention provides pharmaceutical compositions and methods of treating cancer with certain peptides.

BACKGROUND p53 is a tumor suppressor and transcription factor that responds to cellular stress by activating the transcription of numerous genes involved in cell cycle arrest, apoptosis and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. Absence of p53 function is a continuous requirement for the maintenance of established tumors. When p53 function is restored to tumors with inactivated p53, the tumors regressed. p53 is inactivated by mutation and/or loss in 50% of solid tumors and 10% of liquid tumors. Other key members of the p53 pathway are also genetically or epigenetically altered in cancer.

Mutations in p53 are associated with 50% of all reported human cancers (Soussi et al., 2006). Structural instability of p53 mutants leads to partial unfolding (Bullock and Fersht, 2001) which in turn may cause p53 to form aggregates similar to those seen in amyloid diseases (Xu et al, 2011; Levy et al, Eisenberg and Jucker, 2012). The process of p53 misfolding and aggregation results in protein inactivation, thereby removing the 'guardian of the genome' from its protective function (Xu et al, 2011).

There is a need for agents that can specifically destabilize p53 aggregates or prevent them from forming, for use in treating forms of cancer in which p53 is inactivated due to the fact that it is aberrantly folded and/or aggregated. The potential for applicability of such a targeted therapeutic agent is great.

SUMMARY

The present invention provides peptides that exhibit activity in inhibiting cell proliferation. This application relates, e.g., to peptides which bind to p53 protein molecules having an aberrant (e.g. pathological) conformation and which restore the conformation of the p53 molecules having the aberrant conformation. The aberrant conformation can be, for example, misfolding of the molecule resulting from a mutation in the molecule or other factors, or the formation of amyloid aggregates of wild type or mutant p53 molecules. As a result of the treatment with the peptides of the present invention, biological or biochemical activities which were lost or inhibited as a result of the aberrant conformation are reactivated or restored. For example, the peptides can inhibit further aggregation of p53 amyloid aggregates and/or restore p53 functions such as induction or initiation of apoptosis, inhibition of cell proliferation, and/or inducing shrinkage of a tumor.

The present invention provides highly potent peptides and modified peptide agents that can efficiently reactivate p53 conformational mutants, ideally by changing the mutant p53 proteins conformation and/or activity to resemble that of a wild type, functional p53 protein. The present invention thus provides peptides, compositions that comprise the peptides, and their use in treating mutant p53 related conditions, where activation of conformationally defective p53 proteins may be beneficial.

The present invention is based on the identification of highly potent peptide and peptide-based agents that can efficiently reactivate p53 conformational mutants, more efficiently than previously known peptides identified for this use. The present invention thus provides, in an aspect, a recombinant or synthetic peptide comprising or consisting of the amino-acid sequence set forth in any one of SEQ ID NOs: 1-213, 230-236 and 239.

One aspect of the invention is a peptide represented by Formulas I-III. In some variations, the peptides are capable of modulating, especially inhibiting, protein aggregation, including aggregation of p53 and/or p63 and/or p73. Inhibitory peptides of the invention, including the active variants, are sometimes referred to herein as "inhibitory peptides of the invention."

The present disclosure moreover provides compositions, e.g., pharmaceutical compositions, comprising any of the peptides and variant peptides described herein and a pharmaceutically acceptable carrier, as well as a method of treating or preventing a disease or medical condition (e.g., cancer) in a patient. In some variations, the method comprises administering to the patient a peptide or peptide variant described herein, optionally formulated into a pharmaceutical composition, in an amount effective to treat the disease or medical condition.

Other aspects of the invention include methods of inhibiting proliferation of cells, including cells with aberrant p53 and/or aberrant p63 and/or aberrant p73 expression or activity. For example, such methods comprise contacting the cells with a peptide or peptide variant described herein. In some variations, the cells are in a patient, and the contacting comprises administering the peptide, or a composition that comprises the peptide, to the patient. Other aspects of the invention will be apparent from the detailed description and claims that follow.

DETAILED DESCRIPTION

Figure 1A:
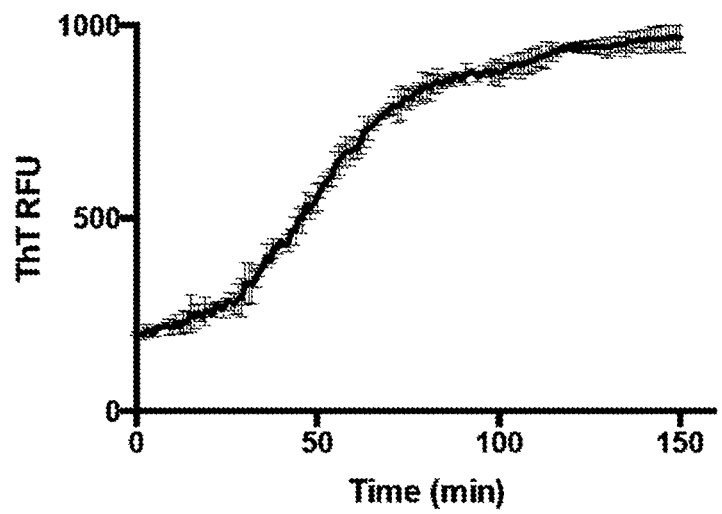
FIGS. 1(a) and 1(b) show the aggregation of p63 and p73 amyloidogenic regions, respectively. The aggregation of the p63 and p73 sequences are monitored via Thioflavin T assay: an increase in Thioflavin T fluorescence is detected over time due to the formation of increasing amounts of amyloid to which the dye can specifically bind.

In one aspect the invention provides peptides that therapeutically affect p53 related cell proliferation, more specifically cancer.

In one aspect the invention provides peptides that therapeutically affect p63 related cell proliferation.

In one aspect the invention provides peptides that therapeutically affect p73 related cell proliferation.

In one embodiment, the invention comprises a peptide of any of the amino acid sequences set forth in any one of SEQ ID NO: 1-213, 230-236 and 239.

In one embodiment, the invention comprises a peptide comprising an amino acid sequence of Formula I Xaa1-Xaa2-Xaa3-Xaa4-Xaa5-Xaa6-Xaa7-Xaa8    (I)

wherein
Xaa1 is Ile, Leu, Arg, Ala, Trp, Phe, Thr, Chg, Tyr, dArg, dHis, dLeu, dIle, dLys, dTyr, dSer, dTrp, dAla, dGln or dPhe;
Xaa2 is Arg, homoArg, Phe, Trp, Gln, His, Ser, Thr, Val, Leu, Ala, Tyr, dPhe, dArg, dHis, dLeu, dIle, dVal, dMet, dTyr, dAla, dGln or dTrp;
Xaa3 is Chg, Ile, N-Me-Ile, Arg, Tyr, Lys, Val, Phe, Phg, Ala, Leu, dArg, dLys, dHis, dMet, dAla, dGln, dGlu, dTrp or dTyr;
Xaa4 is N-Me-Lys, homoArg, Arg, Lys, Glu, Met, Gln, Ile, Leu, Ala, Phe, Tyr, dArg, dLys, dHis, dAla, dIle, dMet, dGln, dTrp, dPhe or dTyr;
Xaa5 is His, Arg, Lys, Gln, Tyr, Thr, Ile, Leu, Ala, Phe, dHis, dArg, dLys, dAla, dLeu, dGln, dTrp, dPhe or dTyr;
Xaa6 is Tyr, Thr, Ala, Gln, Leu, Val, His, Lys, Arg, Trp, Phe, dArg, dGln, dAla, dLys, dTyr, dTrp or dHis;
Xaa7 is absent, Arg, Ala, His, Thr, Ser, Glu, Lys, dArg, dLys, dAla, dAsn, dGln, dSer, or dHis; and
Xaa8 is absent or Pro;
provided the peptide is not IRYRRYR (SEQ ID NO: 218), YRIRRYR (SEQ ID NO: 219), ARARRYR (SEQ ID NO: 220), IRIAAYR (SEQ ID NO: 221), IRIARAR (SEQ ID NO: 222), IRIARYA (SEQ ID NO: 223) or IRIRAYA (SEQ ID NO: 224); further provided Xaa4 is not Ile when Xaa7 is Glu;
C-terminal acids and amides, and N-acetyl derivatives thereof; and pharmaceutically acceptable salts thereof.

In one embodiment, the invention comprises a peptide of Formula I wherein
Xaa1 is Chg, Ile, Leu, Trp, Thr or Tyr;
Xaa2 is homoArg, Arg, Phe, Trp, Thr, Ala or Tyr;
Xaa3 is Chg, Ile, Arg, Phg or Leu;
Xaa4 is homoArg, Arg, Lys, Ala, or Tyr;
Xaa5 is His, Arg, Tyr, Leu, Ala or Phe;
Xaa6 is Tyr, Ala, Gln, Leu, Val, His, Trp, or Phe;
Xaa7 is Arg, Ala, His, or Lys; and
Xaa8 is absent;
C-terminal acids and amides, and N-acetyl derivatives thereof; and pharmaceutically acceptable salts thereof.

In one embodiment, the invention comprises a peptide of Formula I wherein at least one amino acid is selected from
Xaa1 is Chg;
Xaa2 is homoArg;
Xaa3 is Phg or Chg; and
Xaa4 is homoArg;
C-terminal acids and amides and N-acetyl derivatives thereof; and pharmaceutically acceptable salts thereof.

In one embodiment, the invention comprises a peptide comprising an amino acid sequence of Formula Ia (Ia)
(SEQ ID NO: 1)
Xaa1-Xaa2-Xaa3-Xaa4-Xaa5-Xaa6-Xaa7-Xaa8 wherein
Xaa1 is Ile, Leu, Arg, Ala, Trp, Phe, Thr, Chg, Phg, Tyr, dArg, dHis, dLeu, dIle, dLys, dTyr, dSer, dTrp, dAla, dGln or dPhe;
Xaa2 is Arg, homoArg, Phe, Trp, Gln, His, Ser, Thr, Val, Leu, Ala, Tyr, dPhe, dArg, dHis, dLeu, dIle, dVal, dMet, dTyr, dAla, dGln or dTrp;
Xaa3 is Chg, Ile, N-Me-Ile, Arg, Tyr, Lys, Val, Phe, Phg, Ala, Leu, dArg, dLys, dHis, dMet, dAla, dGln, dGlu, dTrp or dTyr;
Xaa4 is N-Me-Lys, homoArg, Arg, Lys, Glu, Met, Gln, Ile, Leu, Ala, Phe, Tyr, dArg, dLys, dHis, dAla, dIle, dMet, dGln, dTrp, dPhe or dTyr;
Xaa5 is His, Arg, Lys, Gln, Tyr, Thr, Ile, Leu, Ala, Phe, dHis, dArg, dLys, dAla, dLeu, dGln, dTrp, dPhe or dTyr;
Xaa6 is Tyr, Thr, Ala, Gln, Leu, Val, His, Lys, Arg, Trp, Phe, dArg, dGln, dAla, dLys, dTyr, dTrp or dHis;
Xaa7 is absent, Arg, Ala, His, Thr, Ser, Glu, Lys, dArg, dLys, dAla, dAsn, dGln, dSer, or dHis; and
Xaa8 is absent or Pro;
provided the peptide is not IRYRRYR (SEQ ID NO: 218), YRIRRYR (SEQ ID NO: 219), ARARRYR (SEQ ID NO: 220), IRIAAYR (SEQ ID NO: 221), IRIARAR (SEQ ID NO: 222), IRIARYA (SEQ ID NO: 223) or IRIRAYA (SEQ ID NO: 224); further provided Xaa4 is not Ile when Xaa7 is Glu;
C-terminal acids and amides, and N-acetyl derivatives thereof; and pharmaceutically acceptable salts thereof.

In one embodiment, the invention comprises a peptide of Formula Ia wherein
Xaa1 is Chg, Phg, Ile, Leu, Trp, Thr or Tyr;
Xaa2 is homoArg, Arg, Phe, Trp, Thr, Ala or Tyr;
Xaa3 is Chg, Ile, Arg, Phg or Leu;
Xaa4 is homoArg, Arg, Lys, Ala, or Tyr;
Xaa5 is His, Arg, Tyr, Leu, Ala or Phe;
Xaa6 is Tyr, Ala, Gln, Leu, Val, His, Trp, or Phe;
Xaa7 is Arg, Ala, His, or Lys; and
Xaa8 is absent;
C-terminal acids and amides, and N-acetyl derivatives thereof; and pharmaceutically acceptable salts thereof.

In one embodiment, the invention comprises a peptide of Formula Ia wherein at least one amino acid is selected from
Xaa1 is Chg or Phg;
Xaa2 is homoArg;
Xaa3 is Phg or Chg; and
Xaa4 is homoArg;

C-terminal acids and amides and N-acetyl derivatives thereof; and pharmaceutically acceptable salts thereof.

In one embodiment, the invention comprises a peptide selected from

|                              |                 |
|------------------------------|-----------------|
| Ile-Arg-Phg-Arg-Arg-Tyr-Arg, | (SEQ ID NO: 2)  |
| Ile-homoArg-Ile-homoArg-Arg-Tyr-Arg, | (SEQ ID NO: 3) |
| Phg-Arg-Phg-Arg-Arg-Tyr-Arg, | (SEQ ID NO: 4)  |
| Ile-Arg-Ile-homoArg-Arg-Tyr-Arg, | (SEQ ID NO: 5) |
| Ile-homoArg-Ile-homoArg-Arg-Trp-Arg, | (SEQ ID NO: 6) |
| Chg-Arg-Chg-Arg-Arg-Tyr-Arg, and | (SEQ ID NO: 7) |
| Ile-Arg-Chg-Arg-Arg-Tyr-Arg, | (SEQ ID NO: 8)  |

C-terminal acids and amides and N-acetyl derivatives thereof; and a pharmaceutically acceptable salt thereof.

In one embodiment, the invention comprises a peptide comprising an amino acid sequence of Formula II Xaa23-Xaa24-Xaa25-Xaa26-Xaa27-Xaa28-Xaa29-Xaa30 (II)

wherein
Xaa23 is Ile, Leu, Arg, Ala, Trp, Phe, Thr or Tyr;
Xaa24 is Arg, Phe, Trp, Gln, His, Ser, Thr, Val, Leu, Ala or Tyr;
Xaa25 is Ile, N-Me-Ile, Arg, Tyr, Lys, Val, Phe, Ala, or Leu;
Xaa26 is Arg, Lys, N-Me-Lys, Glu, Met, Gln, Ile, Leu, Ala, Phe, or Tyr;
Xaa27 is His, Arg, Lys, Gln, Tyr, Thr, Ile, Leu, Ala or Phe;
Xaa28 is Tyr, Thr, Ala, Gln, Leu, Val, His, Lys, Arg, Trp, or Phe;
Xaa29 is absent, Arg, Pro, Arg, Ala, His, Thr, Ser, Glu or Lys; and
Xaa30 is Pro or absent;
provided the peptide is not IRYRRYR (SEQ ID NO: 218), YRIRRYR (SEQ ID NO: 219), ARARRYR (SEQ ID NO: 220), IRIAAYR (SEQ ID NO: 221), IRIARAR (SEQ ID NO: 222), IRIARYA (SEQ ID NO: 223) or IRIRAYA (SEQ ID NO: 224); further provided Xaa26 is not Ile when Xaa29 is Glu;
C-terminal acids and amides and N-acetyl derivatives thereof; and pharmaceutically acceptable salts thereof.

In one embodiment, the invention comprises a peptide comprising an amino acid sequence of Formula IIa (IIa)
Xaa23-Xaa24-Xaa25-Xaa26-Xaa27-Xaa28-Xaa29-Xaa30 (SEQ ID NO: 9)

wherein
Xaa23 is Ile, Leu, Arg, Ala, Trp, Phe, Thr or Tyr;
Xaa24 is Arg, Phe, Trp, Gln, His, Ser, Thr, Val, Leu, Ala or Tyr;
Xaa25 is Ile, N-Me-Ile, Arg, Tyr, Lys, Val, Phe, Ala, or Leu;
Xaa26 is Arg, Lys, N-Me-Lys, Glu, Met, Gln, Ile, Leu, Ala, Phe, or Tyr;
Xaa27 is His, Arg, Lys, Gln, Tyr, Thr, Ile, Leu, Ala or Phe;
Xaa28 is Tyr, Thr, Ala, Gln, Leu, Val, His, Lys, Arg, Trp, or Phe;
Xaa29 is absent, Arg, Ala, His, Thr, Ser, Glu or Lys; and
Xaa30 is Pro or absent;
provided the peptide is not IRYRRYR (SEQ ID NO: 218), YRIRRYR (SEQ ID NO: 219), ARARRYR (SEQ ID NO: 220), IRIAAYR (SEQ ID NO: 221), IRIARAR (SEQ ID NO: 222), IRIARYA (SEQ ID NO: 223) or IRIRAYA (SEQ ID NO: 224); further provided Xaa26 is not Ile when Xaa29 is Glu;
C-terminal acids and amides and N-acetyl derivatives thereof; and pharmaceutically acceptable salts thereof.

In one embodiment, the invention comprises a peptide of Formula II wherein
Xaa23 is Ile, Leu, Trp, Thr or Tyr;
Xaa24 is Arg, Phe, Trp, Thr, Ala or Tyr;
Xaa25 is Ile, Arg, or Leu;
Xaa26 is Arg, Lys, Ala, or Tyr;
Xaa27 is His, Arg, Tyr, Leu, Ala or Phe;
Xaa28 is Tyr, Ala, Gln, Leu, Val, His, Trp, or Phe;
Xaa29 is Arg, Ala, His, or Lys; and
Xaa30 is absent;
C-terminal acids and amides, and N-acetyl derivatives thereof; and pharmaceutically acceptable salts thereof.

In one embodiment, the invention comprises a peptide selected from

|                 |                  |
|-----------------|------------------|
| LTRITYH,        | (SEQ ID NO: 10)  |
| IRIRHYR,        | (SEQ ID NO: 11)  |
| IRIRRYR,        | (SEQ ID NO: 12)  |
| IRIRAYR,        | (SEQ ID NO: 13)  |
| LRIRYWK,        | (SEQ ID NO: 14)  |
| IRIRRAR,        | (SEQ ID NO: 15)  |
| IRIARYR,        | (SEQ ID NO: 16)  |
| IRIRRYA,        | (SEQ ID NO: 17)  |
| IRIYRYK,        | (SEQ ID NO: 18)  |
| TRIRFYR,        | (SEQ ID NO: 19)  |
| Ac-IRIRRYR-NH2, | (SEQ ID NO: 20)  |
| LYIRYLR,        | (SEQ ID NO: 21)  |
| LRIKYHR,        | (SEQ ID NO: 22)  |
| IAIRRYR,        | (SEQ ID NO: 23)  |
| LRIRRYR,        | (SEQ ID NO: 24)  |

-continued

LWIKYHR, (SEQ ID NO: 25)

IRIRRWR, (SEQ ID NO: 26)

LRIYRVR, (SEQ ID NO: 27)

WTIKLWH, (SEQ ID NO: 28)

LRIRFFR, (SEQ ID NO: 29)

LTIRYYK, (SEQ ID NO: 30)

YRLRYLR, (SEQ ID NO: 31)

LFRYYQK, (SEQ ID NO: 32)

LVIRYHR, (SEQ ID NO: 33)

RFYRYLR, (SEQ ID NO: 34)

LRI(N-Me)KYHR, (SEQ ID NO: 35)

IRIRHYRP, (SEQ ID NO: 36)

ARIRRYR, (SEQ ID NO: 37)

LRLRHYR, (SEQ ID NO: 38)

LYIKYHR, (SEQ ID NO: 39)

YTRITYH, (SEQ ID NO: 40)

LRIYHHK, (SEQ ID NO: 41)

IRLRRYR, (SEQ ID NO: 42)

YRLRYVR, (SEQ ID NO: 43)

LYIRYTH, (SEQ ID NO: 44)

LRIRHYT, (SEQ ID NO: 45)

FRIRRYR, (SEQ ID NO: 46)

LYIRLTH, (SEQ ID NO: 47)

LTIRLWH, (SEQ ID NO: 48)

LYIRTLH, (SEQ ID NO: 49)

WTIRYYK, (SEQ ID NO: 50)

IRIRRY, (SEQ ID NO: 51)

LFIKYHR, (SEQ ID NO: 52)

TRIYRYK, (SEQ ID NO: 53)

WTIRYYH, (SEQ ID NO: 54)

LAIKYHR, (SEQ ID NO: 55)

WTRITLK, (SEQ ID NO: 56)

LTIKLWH, (SEQ ID NO: 57)

LLIKYHA, (SEQ ID NO: 58)

WTRIYLH, (SEQ ID NO: 59)

LRIRHVK, (SEQ ID NO: 60)

LLIKYHR, (SEQ ID NO: 61)

IRIRRAA, (SEQ ID NO: 62)

LYIRTYH, (SEQ ID NO: 63)

LLIKAHR, (SEQ ID NO: 64)

WYIRLWK, (SEQ ID NO: 65)

IYIYHQR, (SEQ ID NO: 66)

RLYIRLS, (SEQ ID NO: 67)

WYIRTYH, (SEQ ID NO: 68)

WYIRLWH, (SEQ ID NO: 69)

LTIRTWH, (SEQ ID NO: 70)

LLIKYAR, (SEQ ID NO: 71)

LYIRTWH, (SEQ ID NO: 72)

LYIRHK, (SEQ ID NO: 73)

LTIRLTH, (SEQ ID NO: 74)

LR(N-Me)IKYHR, (SEQ ID NO: 75)

TLIIYHR, (SEQ ID NO: 76)

LYIFRHT, (SEQ ID NO: 77)

WYIRLTH, (SEQ ID NO: 78)

WTRILWH, (SEQ ID NO: 79)

TYIRYLR, (SEQ ID NO: 80)

WTRIYYH, (SEQ ID NO: 81)

LTIMLWH, (SEQ ID NO: 82)

WTKITLH, (SEQ ID NO: 83)

LFIYYQR, (SEQ ID NO: 84)

IQIYRYK, (SEQ ID NO: 85)

IRIRAAR, (SEQ ID NO: 86)

LLIAYHR, (SEQ ID NO: 87)

LFIFYHR, (SEQ ID NO: 88)

IRVYKYS, (SEQ ID NO: 89)

LTIQLWH, (SEQ ID NO: 90)

YYIRYYK, (SEQ ID NO: 91)

IRFRRYR, (SEQ ID NO: 92)

WRIRRYR, (SEQ ID NO: 93)

WTIMLWH, (SEQ ID NO: 94)

LTIRTLH, (SEQ ID NO: 95)

ALIKYHR, (SEQ ID NO: 96)

LHIEHR, (SEQ ID NO: 97)

IFVYHH, (SEQ ID NO: 98)

WTIKLTH, (SEQ ID NO: 99)

IHIEIK, (SEQ ID NO: 100)

WTIRTWH, (SEQ ID NO: 101)

YTYMLWK, (SEQ ID NO: 102)

LSIRQH, (SEQ ID NO: 103)

IRARRYR, (SEQ ID NO: 104)

YYIRTYH, (SEQ ID NO: 105)

LLAKYHR, (SEQ ID NO: 106)

IWIRRWR, (SEQ ID NO: 107)

AYYYRHR, (SEQ ID NO: 108)

TYVYRRR, (SEQ ID NO: 109)

TRIYRVK, (SEQ ID NO: 110)

TYIYRQR, (SEQ ID NO: 111)

LTRILTH, (SEQ ID NO: 112)

ILRLYFR, (SEQ ID NO: 113)

FFRLYLR, (SEQ ID NO: 114)

LTRILWH, (SEQ ID NO: 115)

FRLYIH, (SEQ ID NO: 116)

TFVFRHR, (SEQ ID NO: 117)

IRIRRYE, (SEQ ID NO: 118)

YTIQLWH, (SEQ ID NO: 119)

TFILRLT, (SEQ ID NO: 120)
and

YTYEYWH; (SEQ ID NO: 121)

C-terminal acids and amides and N-acetyl derivatives thereof; and a pharmaceutically acceptable salt thereof.

In one embodiment, the invention comprises a peptide selected from

IRIRHYR, (SEQ ID NO: 11)

IRIRRYR, (SEQ ID NO: 12)

LRIRYWK, (SEQ ID NO: 14)

IRIYRYK, (SEQ ID NO: 18)

TRIRFYR, (SEQ ID NO: 19)

WTIKLWH, (SEQ ID NO: 28)

LRIRFFR, (SEQ ID NO: 29)
and

LRLRHYR, (SEQ ID NO: 38)

C-terminal acids and amides and N-acetyl derivatives thereof; and a pharmaceutically acceptable salt thereof.

An embodiment of the invention comprises a peptide of the amino acid sequence IRIRHYR (SEQ ID NO: 11). In some embodiments a peptide according to the present invention comprises up to 2 amino acid modifications relative to SEQ ID NO: 11. In some embodiments a peptide according to the present invention comprises 1 amino acid modification relative to SEQ ID NO: 11, wherein in one or more of the positions 1, 2, 3, 4, 5, 6 or 7, wherein the amino acid numbering corresponds to SEQ ID NO: 11.

An embodiment of the invention comprises a peptide of the amino acid sequence IRIRRYR (SEQ ID NO: 12). In some embodiments a peptide according to the present invention comprises up to 2 amino acid modifications relative to SEQ ID NO: 12. In some embodiments a peptide according to the present invention comprises 1 amino acid modification relative to SEQ ID NO: 12, wherein in one or more of the positions 1, 2, 3, 4, 5, 6 or 7, wherein the amino acid numbering corresponds to SEQ ID NO: 12.

An embodiment of the invention comprises a peptide of the amino acid sequence LRIRYWK (SEQ ID NO: 14). In some embodiments a peptide according to the present invention comprises up to 2 amino acid modifications relative to SEQ ID NO: 14. In some embodiments a peptide according to the present invention comprises 1 amino acid modification relative to SEQ ID NO: 14, wherein in one or more of the positions 1, 2, 3, 4, 5, 6 or 7, wherein the amino acid numbering corresponds to SEQ ID NO: 14.

An embodiment of the invention comprises a peptide of the amino acid sequence IRIYRYK (SEQ ID NO: 18). In some embodiments a peptide according to the present invention comprises up to 2 amino acid modifications relative to SEQ ID NO: 18. In some embodiments a peptide according to the present invention comprises 1 amino acid modification relative to SEQ ID NO: 18, wherein in one or more of the positions 1, 2, 3, 4, 5, 6 or 7, wherein the amino acid numbering corresponds to SEQ ID NO: 18.

An embodiment of the invention comprises a peptide of the amino acid sequence TRIRFYR (SEQ ID NO: 19). In some embodiments a peptide according to the present invention comprises up to 2 amino acid modifications relative to SEQ ID NO: 19. In some embodiments a peptide according to the present invention comprises 1 amino acid modification relative to SEQ ID NO: 19, wherein in one or more of the positions 1, 2, 3, 4, 5, 6 or 7, wherein the amino acid numbering corresponds to SEQ ID NO: 19.

An embodiment of the invention comprises a peptide of the amino acid sequence WTIKLWH (SEQ ID NO: 28). In some embodiments a peptide according to the present invention comprises up to 2 amino acid modifications relative to SEQ ID NO: 28. In some embodiments a peptide according to the present invention comprises 1 amino acid modification relative to SEQ ID NO: 28, wherein in one or more of the positions 1, 2, 3, 4, 5, 6 or 7, wherein the amino acid numbering corresponds to SEQ ID NO: 28.

An embodiment of the invention comprises a peptide of the amino acid sequence LRIRFFR (SEQ ID NO: 29). In some embodiments a peptide according to the present invention comprises up to 2 amino acid modifications relative to SEQ ID NO: 29. In some embodiments a peptide according to the present invention comprises 1 amino acid modification relative to SEQ ID NO: 29, wherein in one or more of the positions 1, 2, 3, 4, 5, 6 or 7, wherein the amino acid numbering corresponds to SEQ ID NO: 29.

An embodiment of the invention comprises a peptide of the amino acid sequence LRLRHYR (SEQ ID NO: 38). In some embodiments a peptide according to the present invention comprises up to 2 amino acid modifications relative to SEQ ID NO: 38. In some embodiments a peptide according to the present invention comprises 1 amino acid modification relative to SEQ ID NO: 38, wherein in one or more of the positions 1, 2, 3, 4, 5, 6 or 7, wherein the amino acid numbering corresponds to SEQ ID NO: 38.

An embodiment of the invention comprises a peptide comprising an amino acid sequence of Formula III (III)
(SEQ ID NO: 201)
Xaa9-Xaa10-Xaa11-Xaa12-Xaa13-Xaa14-Xaa15 wherein
Xaa9 is dArg, dHis, dLeu, dIle, dLys, dTyr, dSer, dTrp, dAla, dGln or dPhe;
Xaa10 is dPhe, dArg, dHis, dLeu, dIle, dVal, dMet, dTyr, dAla, dGln or dTrp;
Xaa11 is dArg, dLys, dHis, dMet, dAla, dGln, dGlu, dTrp or dTyr;
Xaa12 is dArg, dLys, dHis, dAla, dIle, dMet, dGln, dTrp, dPhe or dTyr;
Xaa13 is dHis, dArg, dLys, dAla, dLeu, dGln, dTrp, dPhe or dTyr;
Xaa14 is dArg, dGln, dAla, dLys, dTyr, dTrp or dHis; and
Xaa15 is dArg, dLys, dAla, dAsn, dGln, dSer, dHis or absent;

C-terminal acids and amides and N-acetyl derivatives thereof; and pharmaceutically acceptable salts thereof.

An embodiment of the invention comprises a peptide of Formula III wherein
Xaa9 is dArg, dHis, dLeu, dLys, dTyr, dSer, dTrp, dGln or dPhe;
Xaa10 is dPhe, dLeu, dIle, dTyr, dGln or dTrp;
Xaa11 is dArg, dLys, dHis, dGlu, dTrp or dTyr;
Xaa12 is dArg, dLys, dIle, dTrp, dPhe or dTyr;
Xaa13 is dHis, dArg, dLys, dLeu, dTrp, dPhe or dTyr;
Xaa14 is dArg, dGln, dTrp or dHis; and
Xaa15 is dArg, dLys, dAsn, dHis or absent;
C-terminal acids and amides and N-acetyl derivatives thereof; and pharmaceutically acceptable salts thereof.

An embodiment of the invention comprises a peptide selected from

|  | (SEQ ID NO: 122) |
|---|---|
| hqrryqr, | |
| kfrfyhr, | (SEQ ID NO: 123) |
| rihyfrr, | (SEQ ID NO: 124) |
| hwrwlrr, | (SEQ ID NO: 125) |
| rwrylrr, | (SEQ ID NO: 126) |
| rfhyfrk, | (SEQ ID NO: 127) |
| klkklh, | (SEQ ID NO: 128) |
| kwrwyrr, | (SEQ ID NO: 129) | rfyyhrr, (SEQ ID NO: 130)

wwrwyrr, (SEQ ID NO: 131)

rfyrrhr, (SEQ ID NO: 132)

kyrwyrh, (SEQ ID NO: 133)

fwrwhr, (SEQ ID NO: 134)

qqryywr, (SEQ ID NO: 135)

hlriwrn, (SEQ ID NO: 136)

ffrfhrr, (SEQ ID NO: 137)

lwrryhr, (SEQ ID NO: 138)

rirwywk, (SEQ ID NO: 139)

yqwrhwr, (SEQ ID NO: 140)

rwywhhr, (SEQ ID NO: 141)

sfwykrr, (SEQ ID NO: 142)

rfefrhr, (SEQ ID NO: 143)

yqyyyqr, (SEQ ID NO: 144)

rqwyhwr, (SEQ ID NO: 145)

hqryywr, (SEQ ID NO: 146)

hwryhrr, (SEQ ID NO: 147)

rwhwhr, (SEQ ID NO: 148)

fwrwhrr, (SEQ ID NO: 149)

ffrfhhr, (SEQ ID NO: 150)

rwrwhhr, (SEQ ID NO: 151)

hwrwywk, (SEQ ID NO: 152)

fwrhkhr, (SEQ ID NO: 153)

qiryfrr, (SEQ ID NO: 154)

fwrwarr, (SEQ ID NO: 155)

qfrmhhr, (SEQ ID NO: 156)

yqyyfwr, (SEQ ID NO: 157)

swwfrhr, (SEQ ID NO: 158)

yqwryrr, (SEQ ID NO: 159)

hlryhrk, (SEQ ID NO: 160)

yqwyrwq, (SEQ ID NO: 161)

lwrwyrr, (SEQ ID NO: 162)

rwrilqk, (SEQ ID NO: 163)

rqhyrwr, (SEQ ID NO: 164)

rlhwkhh, (SEQ ID NO: 165)

rwmywqr, (SEQ ID NO: 166)

fwrwhra, (SEQ ID NO: 167)

rqmqyrr, (SEQ ID NO: 168)

fwawhrr, (SEQ ID NO: 169)

rfyrhhr, (SEQ ID NO: 170)

fwrwhar, (SEQ ID NO: 171)

hwrwrwr, (SEQ ID NO: 172)

krwrhqr, (SEQ ID NO: 173)

wwrrhhr, (SEQ ID NO: 174)

kqwyhwr, (SEQ ID NO: 175)

awrwhrr, (SEQ ID NO: 176)

farwhrr, (SEQ ID NO: 177)

fwrahrr, (SEQ ID NO: 178)

rqhyhwr, (SEQ ID NO: 179)

swrwhhr, (SEQ ID NO: 180)

shwrrhr, (SEQ ID NO: 181)

ywqwrqs, (SEQ ID NO: 182)

yqwqyqr, (SEQ ID NO: 183)

fwrwhaa, (SEQ ID NO: 184)

wwrfhwr, (SEQ ID NO: 185)

rlkwrw, (SEQ ID NO: 186)

qlkwlh, (SEQ ID NO: 187)

farahrr, (SEQ ID NO: 188)

klkwlw, (SEQ ID NO: 189)

ilkwlw, (SEQ ID NO: 190)

shwrhhr, (SEQ ID NO: 191)

rqwyrwq, (SEQ ID NO: 192)

qwrwrhr, (SEQ ID NO: 193)

qvryhkn, (SEQ ID NO: 194)

klkwqw, (SEQ ID NO: 195)

klkway, (SEQ ID NO: 196)

rmwrhhr, (SEQ ID NO: 197)

qfhykrr, (SEQ ID NO: 198)

rfhrhhr, and (SEQ ID NO: 199)

hqrqyqr; (SEQ ID NO: 200)

C-terminal acids and amides and N-acetyl derivatives thereof; and a pharmaceutically acceptable salt thereof.

An embodiment of the invention comprises a peptide of Formula III selected from rfyyhrr, (SEQ ID NO: 130)

lwrryhr, (SEQ ID NO: 138)

qqryywr (SEQ ID NO: 135)

yqwyrwq (SEQ ID NO: 161)

rihyfrr, (SEQ ID NO: 124)

kwrwyrr, (SEQ ID NO: 129)

hlriwrn, (SEQ ID NO: 136)

hqrqyqr (SEQ ID NO: 200)

kfrfyhr, (SEQ ID NO: 123)
or ffrfhhr; (SEQ ID NO: 150)

C-terminal acids and amides and N-acetyl derivatives thereof; or a pharmaceutically acceptable salt thereof.

An embodiment of the invention comprises a peptide of the amino acid sequence rfyyhrr (SEQ ID NO: 130). In some embodiments a peptide according to the present invention comprises up to 2 amino acid modifications relative to SEQ ID NO: 130. In some embodiments a peptide according to the present invention comprises 1 amino acid modification relative to SEQ ID NO: 130, wherein in one or more of the positions 1, 2, 3, 4, 5, 6 or 7, wherein the amino acid numbering corresponds to SEQ ID NO: 130.

An embodiment of the invention comprises a peptide of the amino acid sequence lwrryhr (SEQ ID NO: 138). In some embodiments a peptide according to the present invention comprises up to 2 amino acid modifications relative to SEQ ID NO: 138. In some embodiments a peptide according to the present invention comprises 1 amino acid modification relative to SEQ ID NO: 138, wherein in one or more of the positions 1, 2, 3, 4, 5, 6 or 7, wherein the amino acid numbering corresponds to SEQ ID NO: 138.

An embodiment of the invention comprises a peptide of the amino acid sequence kfrfyhr (SEQ ID NO: 123). In some embodiments a peptide according to the present invention comprises up to 2 amino acid modifications relative to SEQ ID NO: 123. In some embodiments a peptide according to the present invention comprises 1 amino acid modification relative to SEQ ID NO: 123, wherein in one or more of the positions 1, 2, 3, 4, 5, 6 or 7, wherein the amino acid numbering corresponds to SEQ ID NO: 123.

An embodiment of the invention comprises a peptide of the amino acid sequence ffrfhhr (SEQ ID NO: 150). In some embodiments a peptide according to the present invention comprises up to 2 amino acid modifications relative to SEQ ID NO: 150. In some embodiments a peptide according to the present invention comprises 1 amino acid modification relative to SEQ ID NO: 150, wherein in one or more of the positions 1, 2, 3, 4, 5, 6 or 7, wherein the amino acid numbering corresponds to SEQ ID NO: 150.

An embodiment of the invention comprises a peptide of the amino acid sequence qqryywr (SEQ ID NO: 135). In some embodiments a peptide according to the present invention comprises up to 2 amino acid modifications relative to SEQ ID NO: 135. In some embodiments a peptide according to the present invention comprises 1 amino acid modification relative to SEQ ID NO: 135, wherein in one or more of the positions 1, 2, 3, 4, 5, 6 or 7, wherein the amino acid numbering corresponds to SEQ ID NO: 135.

An embodiment of the invention comprises a peptide of the amino acid sequence yqwyrwq (SEQ ID NO: 161). In some embodiments a peptide according to the present invention comprises up to 2 amino acid modifications relative to SEQ ID NO: 161. In some embodiments a peptide according to the present invention comprises 1 amino acid modification relative to SEQ ID NO: 161, wherein in one or more of the positions 1, 2, 3, 4, 5, 6 or 7, wherein the amino acid numbering corresponds to SEQ ID NO: 161.

An embodiment of the invention comprises a peptide of the amino acid sequence rihyfrr (SEQ ID NO: 124). In some embodiments a peptide according to the present invention comprises up to 2 amino acid modifications relative to SEQ ID NO: 124. In some embodiments a peptide according to the present invention comprises 1 amino acid modification relative to SEQ ID NO: 124, wherein in one or more of the positions 1, 2, 3, 4, 5, 6 or 7, wherein the amino acid numbering corresponds to SEQ ID NO: 124.

An embodiment of the invention comprises a peptide of the amino acid sequence kwrwyrr (SEQ ID NO: 129). In some embodiments a peptide according to the present invention comprises up to 2 amino acid modifications relative to SEQ ID NO: 129. In some embodiments a peptide according to the present invention comprises 1 amino acid modification relative to SEQ ID NO: 129, wherein in one or more of the positions 1, 2, 3, 4, 5, 6 or 7, wherein the amino acid numbering corresponds to SEQ ID NO: 129.

An embodiment of the invention comprises a peptide of the amino acid sequence hlriwrn (SEQ ID NO: 136). In some embodiments a peptide according to the present invention comprises up to 2 amino acid modifications relative to SEQ ID NO: 136. In some embodiments a peptide according to the present invention comprises 1 amino acid modification relative to SEQ ID NO: 136, wherein in one or more of the positions 1, 2, 3, 4, 5, 6 or 7, wherein the amino acid numbering corresponds to SEQ ID NO: 136.

An embodiment of the invention comprises a peptide of the amino acid sequence hqrqyqr (SEQ ID NO: 200). In some embodiments a peptide according to the present invention comprises up to 2 amino acid modifications relative to SEQ ID NO: 200. In some embodiments a peptide according to the present invention comprises 1 amino acid modification relative to SEQ ID NO: 200, wherein in one or more of the positions 1, 2, 3, 4, 5, 6 or 7, wherein the amino acid numbering corresponds to SEQ ID NO: 200.

In some embodiments a peptide according to the invention is represented by the compounds listed in Table 1.

TABLE 1

| Sequence | SEQ ID NO: |
| --- | --- |
| Ile-Arg-Phg-Arg-Arg-Tyr-Arg | (SEQ ID NO: 2), |
| Ile-homoArg-Ile-homoArg-Arg-Tyr-Arg | (SEQ ID NO: 3), |
| Phg-Arg-Phg-Arg-Arg-Tyr-Arg | (SEQ ID NO: 4), |
| Ile-Arg-Ile-homoArg-Arg-Tyr-Arg | (SEQ ID NO: 5), |
| Ile-homoArg-Ile-homoArg-Arg-Trp-Arg | (SEQ ID NO: 6), |
| Chg-Arg-Chg-Arg-Arg-Tyr-Arg | (SEQ ID NO: 7), |
| Ile-Arg-Chg-Arg-Arg-Tyr-Arg | (SEQ ID NO: 8), |
| LTRITYH | (SEQ ID NO: 10), |
| IRIRHYR | (SEQ ID NO: 11), |
| IRIRRYR | (SEQ ID NO: 12), |
| IRIRAYR | (SEQ ID NO: 13), |
| LRIRYWK | (SEQ ID NO: 14), |
| IRIRRAR | (SEQ ID NO: 15), |
| IRIARYR | (SEQ ID NO: 16), |
| IRIRRYA | (SEQ ID NO: 17), |

TABLE 1-continued

| Sequence | SEQ ID NO: |
| --- | --- |
| IRIYRYK | (SEQ ID NO: 18), |
| TRIRFYR | (SEQ ID NO: 19), |
| Ac-IRIRRYR-NH2 | (SEQ ID NO: 20), |
| LYIRYLR | (SEQ ID NO: 21), |
| LRIKYHR | (SEQ ID NO: 22), |
| IAIRRYR | (SEQ ID NO: 23), |
| LRIRRYR | (SEQ ID NO: 24), |
| LWIKYHR | (SEQ ID NO: 25), |
| IRIRRWR | (SEQ ID NO: 26), |
| LRIYRVR | (SEQ ID NO: 27), |
| WTIKLWH | (SEQ ID NO: 28), |
| LRIRFFR | (SEQ ID NO: 29), |
| LTIRYYK | (SEQ ID NO: 30), |
| YRLRYLR | (SEQ ID NO: 31), |
| LFRYYQK | (SEQ ID NO: 32), |
| LVIRYHR | (SEQ ID NO: 33), |
| RFYRYLR | (SEQ ID NO: 34), |
| LRI(N-Me)KYHR | (SEQ ID NO: 35), |
| IRIRHYRP | (SEQ ID NO: 36), |
| ARIRRYR | (SEQ ID NO: 37), |
| LRLRHYR | (SEQ ID NO: 38), |
| LYIKYHR | (SEQ ID NO: 39), |
| YTRITYH | (SEQ ID NO: 40), |
| LRIYHHK | (SEQ ID NO: 41), |
| IRLRRYR | (SEQ ID NO: 42), |
| YRLRYVR | (SEQ ID NO: 43), |
| LYIRYTH | (SEQ ID NO: 44), |
| LRIRHYT | (SEQ ID NO: 45), |
| FRIRRYR | (SEQ ID NO: 46), |
| LYIRLTH | (SEQ ID NO: 47), |
| LTIRLWH | (SEQ ID NO: 48), |
| LYIRTLH | (SEQ ID NO: 49), |
| WTIRYYK | (SEQ ID NO: 50), |
| IRIRRY | (SEQ ID NO: 51), |
| LFIKYHR | (SEQ ID NO: 52), |
| TRIYRYK | (SEQ ID NO: 53), |
| WTIRYYH | (SEQ ID NO: 54), |
| LAIKYHR | (SEQ ID NO: 55), |
| WTRITLK | (SEQ ID NO: 56), |

TABLE 1-continued

| Sequence | SEQ ID NO: |
|---|---|
| LTIKLWH | (SEQ ID NO: 57), |
| LLIKYHA | (SEQ ID NO: 58), |
| WTRIYLH | (SEQ ID NO: 59), |
| LRIRHVK | (SEQ ID NO: 60), |
| LLIKYHR | (SEQ ID NO: 61), |
| IRIRRAA | (SEQ ID NO: 62), |
| LYIRTYH | (SEQ ID NO: 63), |
| LLIKAHR | (SEQ ID NO: 64), |
| WYIRLWK | (SEQ ID NO: 65), |
| IYIYHQR | (SEQ ID NO: 66), |
| RLYIRLS | (SEQ ID NO: 67), |
| WYIRTYH | (SEQ ID NO: 68), |
| WYIRLWH | (SEQ ID NO: 69), |
| LTIRTWH | (SEQ ID NO: 70), |
| LLIKYAR | (SEQ ID NO: 71), |
| LYIRTWH | (SEQ ID NO: 72), |
| LYIRHK | (SEQ ID NO: 73), |
| LTIRLTH | (SEQ ID NO: 74), |
| LR(N-Me)IKYHR | (SEQ ID NO: 75), |
| TLIIYHR | (SEQ ID NO: 76), |
| LYIFRHT | (SEQ ID NO: 77), |
| WYIRLTH | (SEQ ID NO: 78), |
| WTRILWH | (SEQ ID NO: 79), |
| TYIRYLR | (SEQ ID NO: 80), |
| WTRIYYH | (SEQ ID NO: 81), |
| LTIMLWH | (SEQ ID NO: 82), |
| WTKITLH | (SEQ ID NO: 83), |
| LFIYYQR | (SEQ ID NO: 84), |
| IQIYRYK | (SEQ ID NO: 85), |
| IRIRAAR | (SEQ ID NO: 86), |
| LLIAYHR | (SEQ ID NO: 87), |
| LFIFYHR | (SEQ ID NO: 88), |
| IRVYKYS | (SEQ ID NO: 89), |
| LTIQLWH | (SEQ ID NO: 90), |
| YYIRYYK | (SEQ ID NO: 91), |
| IRFRRYR | (SEQ ID NO: 92), |
| WRIRRYR | (SEQ ID NO: 93), |
| WTIMLWH | (SEQ ID NO: 94), |
| LTIRTLH | (SEQ ID NO: 95), |
| ALIKYHR | (SEQ ID NO: 96), |
| LHIEHR | (SEQ ID NO: 97), |
| IFVYHH | (SEQ ID NO: 98), |
| WTIKLTH | (SEQ ID NO: 99), |
| IHIEIK | (SEQ ID NO: 100), |
| WTIRTWH | (SEQ ID NO: 101), |
| YTYMLWK | (SEQ ID NO: 102), |
| LSIRQH | (SEQ ID NO: 103), |
| IRARRYR | (SEQ ID NO: 104), |
| YYIRTYH | (SEQ ID NO: 105), |
| LLAKYHR | (SEQ ID NO: 106), |
| IWIRRWR | (SEQ ID NO: 107), |
| AYYYRHR | (SEQ ID NO: 108), |
| TYVYRRR | (SEQ ID NO: 109), |
| TRIYRVK | (SEQ ID NO: 110), |
| TYIYRQR | (SEQ ID NO: 111), |
| LTRILTH | (SEQ ID NO: 112), |
| ILRLYFR | (SEQ ID NO: 113), |
| FFRLYLR | (SEQ ID NO: 114), |
| LTRILWH | (SEQ ID NO: 115), |
| FRLYIH | (SEQ ID NO: 116), |
| TFVFRHR | (SEQ ID NO: 117), |
| IRIRRYE | (SEQ ID NO: 118), |
| YTIQLWH | (SEQ ID NO: 119), |
| TFILRLT | (SEQ ID NO: 120), |
| YTYEYWH | (SEQ ID NO: 121), |
| hqrryqr | (SEQ ID NO: 122) |
| kfrfyhr | (SEQ ID NO: 123), |
| rihyfrr | (SEQ ID NO: 124), |
| hwrwlrr | (SEQ ID NO: 125), |
| rwrylrr | (SEQ ID NO: 126), |
| rfhyfrk | (SEQ ID NO: 127), |
| klkklh | (SEQ ID NO: 128), |
| kwrwyrr | (SEQ ID NO: 129), |
| rfyyhrr | (SEQ ID NO: 130), |
| wwrwyrr | (SEQ ID NO: 131), |
| rfyrrhr | (SEQ ID NO: 132), |
| kyrwyrh | (SEQ ID NO: 133), |
| fwrwhr | (SEQ ID NO: 134), |

TABLE 1-continued

| Sequence | SEQ ID NO: |
|---|---|
| qqryywr | (SEQ ID NO: 135), |
| hlriwrn | (SEQ ID NO: 136), |
| ffrfhrr | (SEQ ID NO: 137), |
| lwrryhr | (SEQ ID NO: 138), |
| rirwywk | (SEQ ID NO: 139), |
| yqwrhwr | (SEQ ID NO: 140), |
| rwywhhr | (SEQ ID NO: 141), |
| sfwykrr | (SEQ ID NO: 142), |
| rfefrhr | (SEQ ID NO: 143), |
| yqyyyqr | (SEQ ID NO: 144), |
| rqwyhwr | (SEQ ID NO: 145), |
| hqryywr | (SEQ ID NO: 146), |
| hwryhrr | (SEQ ID NO: 147), |
| rwhwhwr | (SEQ ID NO: 148), |
| fwrwhrr | (SEQ ID NO: 149), |
| ffrfhhr | (SEQ ID NO: 150), |
| rwrwhhr | (SEQ ID NO: 151), |
| hwrwywk | (SEQ ID NO: 152), |
| fwrhkhr | (SEQ ID NO: 153), |
| qiryfrr | (SEQ ID NO: 154), |
| fwrwarr | (SEQ ID NO: 155), |
| qfrmhhr | (SEQ ID NO: 156), |
| yqyyfwr | (SEQ ID NO: 157), |
| swwfrhr | (SEQ ID NO: 158), |
| yqwryrr | (SEQ ID NO: 159), |
| hlryhrk | (SEQ ID NO: 160), |
| yqwyrwq | (SEQ ID NO: 161), |
| lwrwyrr | (SEQ ID NO: 162), |
| rwrilqk | (SEQ ID NO: 163), |
| rqhyrwr | (SEQ ID NO: 164), |
| rlhwkhh | (SEQ ID NO: 165), |
| rwmywqr | (SEQ ID NO: 166), |
| fwrwhra | (SEQ ID NO: 167), |
| rqmqyrr | (SEQ ID NO: 168), |
| fwawhrr | (SEQ ID NO: 169), |
| rfyrhhr | (SEQ ID NO: 170), |
| fwrwhar | (SEQ ID NO: 171), |
| hwrwrwr | (SEQ ID NO: 172), |
| krwrhqr | (SEQ ID NO: 173), |

TABLE 1-continued

| Sequence | SEQ ID NO: |
|---|---|
| wwrrhhr | (SEQ ID NO: 174), |
| kqwyhwr | (SEQ ID NO: 175), |
| awrwhrr | (SEQ ID NO: 176), |
| farwhrr | (SEQ ID NO: 177), |
| fwrahrr | (SEQ ID NO: 178), |
| rqhyhwr | (SEQ ID NO: 179), |
| swrwhhr | (SEQ ID NO: 180), |
| shwrrhr | (SEQ ID NO: 181), |
| ywqwrqs | (SEQ ID NO: 182), |
| yqwqyqr | (SEQ ID NO: 183), |
| fwrwhaa | (SEQ ID NO: 184), |
| wwrfhwr | (SEQ ID NO: 185), |
| rlkwrw | (SEQ ID NO: 186), |
| qlkwlh | (SEQ ID NO: 187), |
| farahrr | (SEQ ID NO: 188), |
| klkwlw | (SEQ ID NO: 189), |
| ilkwlw | (SEQ ID NO: 190), |
| shwrhhr | (SEQ ID NO: 191), |
| rqwyrwq | (SEQ ID NO: 192), |
| qwrwhr | (SEQ ID NO: 193), |
| qvryhkn | (SEQ ID NO: 194), |
| klkwqw | (SEQ ID NO: 195), |
| klkway | (SEQ ID NO: 196), |
| rmwrhhr | (SEQ ID NO: 197), |
| qfhykrr | (SEQ ID NO: 198), |
| rfhrhhr | (SEQ ID NO: 199), and |
| hqrqyqr | (SEQ ID NO: 200). |

An embodiment of the invention comprises a peptide comprising an amino acid sequence of Formula I' or II":

(I')
(SEQ ID NO: 202)
(Arg)$_n$-Pro-Ile-Xaa1-Xaa2-Xaa3-Xaa4-Xaa5-Xaa6-Xaa7-Xaa8

(I")
(SEQ ID NO: 239)
(dArg)$_n$-Pro-Ile-Xaa1-Xaa2-Xaa3-Xaa4-Xaa5-Xaa6-Xaa7-Xaa8 wherein
  n is a number between 1 and 16, inclusive;
  Xaa1 is Ile, Leu, Arg, Ala, Trp, Phe, Thr, Chg, Tyr, dArg, dHis, dLeu, dIle, dLys, dTyr, dSer, dTrp, dAla, dGln or dPhe;

Xaa2 is Arg, homoArg, Phe, Trp, Gln, His, Ser, Thr, Val, Leu, Ala, Tyr, dPhe, dArg, dHis, dLeu, dIle, dVal, dMet, dTyr, dAla, dGln or dTrp;

Xaa3 is Chg, Ile, N-Me-Ile, Arg, Tyr, Lys, Val, Phe, Phg, Ala, Leu, dArg, dLys, dHis, dMet, dAla, dGln, dGlu, dTrp or dTyr;

Xaa4 is N-Me-Lys, homoArg, Arg, Lys, Glu, Met, Gln, Ile, Leu, Ala, Phe, Tyr, dArg, dLys, dHis, dAla, dIle, dMet, dGln, dTrp, dPhe or dTyr;

Xaa5 is His, Arg, Lys, Gln, Tyr, Thr, Ile, Leu, Ala, Phe, dHis, dArg, dLys, dAla, dLeu, dGln, dTrp, dPhe or dTyr;

Xaa6 is Tyr, Thr, Ala, Gln, Leu, Val, His, Lys, Arg, Trp, Phe, dArg, dGln, dAla, dLys, dTyr, dTrp or dHis;

Xaa7 is absent, Arg, Ala, His, Thr, Ser, Glu, Lys, dArg, dLys, dAla, dAsn, dGln, dSer, or dHis; and Xaa8 is absent or Pro;

provided the peptide is not IRYRRYR (SEQ ID NO: 218), YRIRRYR (SEQ ID NO: 219), ARARRYR (SEQ ID NO: 220), IRIAAYR (SEQ ID NO: 221), IRIARAR (SEQ ID NO: 222), IRIARYA (SEQ ID NO: 223) or IRIRAYA (SEQ ID NO: 224; further provided Xaa4 is not Ile when Xaa7 is Glu;

C-terminal acids and amides, and N-acetyl derivatives thereof; and pharmaceutically acceptable salts thereof.

An embodiment of the invention comprises a peptide comprising an amino acid sequence of Formula Ia' or Ia":

(Ia')
(SEQ ID NO: 202)
(Arg)$_n$-Pro-Ile-Xaa1-Xaa2-Xaa3-Xaa4-Xaa5-Xaa6-Xaa7-Xaa8

(Ia")
(SEQ ID NO: 239)
(dArg)$_n$-Pro-Ile-Xaa1-Xaa2-Xaa3-Xaa4-Xaa5-Xaa6-Xaa7-Xaa8 wherein
n is a number between 1 and 16, inclusive;

Xaa1 is Ile, Leu, Arg, Ala, Trp, Phe, Thr, Chg, Phg, Tyr, dArg, dHis, dLeu, dIle, dLys, dTyr, dSer, dTrp, dAla, dGln or dPhe;

Xaa2 is Arg, homoArg, Phe, Trp, Gln, His, Ser, Thr, Val, Leu, Ala, Tyr, dPhe, dArg, dHis, dLeu, dIle, dVal, dMet, dTyr, dAla, dGln or dTrp;

Xaa3 is Chg, Ile, N-Me-Ile, Arg, Tyr, Lys, Val, Phe, Phg, Ala, Leu, dArg, dLys, dHis, dMet, dAla, dGln, dGlu, dTrp or dTyr;

Xaa4 is N-Me-Lys, homoArg, Arg, Lys, Glu, Met, Gln, Ile, Leu, Ala, Phe, Tyr, dArg, dLys, dHis, dAla, dIle, dMet, dGln, dTrp, dPhe or dTyr;

Xaa5 is His, Arg, Lys, Gln, Tyr, Thr, Ile, Leu, Ala, Phe, dHis, dArg, dLys, dAla, dLeu, dGln, dTrp, dPhe or dTyr;

Xaa6 is Tyr, Thr, Ala, Gln, Leu, Val, His, Lys, Arg, Trp, Phe, dArg, dGln, dAla, dLys, dTyr, dTrp or dHis;

Xaa7 is absent, Arg, Ala, His, Thr, Ser, Glu, Lys, dArg, dLys, dAla, dAsn, dGln, dSer, or dHis; and Xaa8 is absent or Pro;

provided the peptide is not IRYRRYR (SEQ ID NO: 218), YRIRRYR (SEQ ID NO: 219), ARARRYR (SEQ ID NO: 220), IRIAAYR (SEQ ID NO: 221), IRIARAR (SEQ ID NO: 222), IRIARYA (SEQ ID NO: 223) or IRIRAYA (SEQ ID NO: 224; further provided Xaa4 is not Ile when Xaa7 is Glu;

C-terminal acids and amides, and N-acetyl derivatives thereof; and pharmaceutically acceptable salts thereof.

An embodiment of the invention comprises a CPP of a peptide of Formula I selected from RRRRRRRRRR-PIIRIRHYR (SEQ ID NO: 203); RRRRRRRRRRPIIRIR-HYP (SEQ ID NO: 204); PRRRRRRRRRRPIIRIRHYRP (SEQ ID NO: 205); RRRRRRRRRRPIIRIRHYRP (SEQ ID NO: 206); PRRRRRRRRRRPILRIRYWKP (SEQ ID NO: 207); PRRRRRRRRRRPITRIRFYRP (SEQ ID NO: 208); PRRRRRRRRRRPIWTIKLWHP (SEQ ID NO: 209); RRRRRRRRRRPIqqryywr (SEQ ID NO: 210); RRRRRRRRRRPIyqwyrwq (SEQ ID NO: 211); RRRRRRRRRRPIkfrfyhr (SEQ ID NO: 212); and RRRRRRRRRRPIrfyyhrr (SEQ ID NO: 213); or a pharmaceutically acceptable salt thereof.

In some embodiments, the present invention also relates to a peptide comprising a sequence having at least 66% sequence identity to any one of amino acid sequences SEQ ID NO: 1-213, 230-236 and 239. In certain embodiments, the % identity is selected from, e.g., at least 70%, at least 75%, at least 80%, at least 85%, at least 90%, or at least 95%, or more sequence identity to a given sequence. In certain embodiments, the % identity is in the range of, e.g., about 65% to about 70%, about 70% to about 80%, about 80% to about 85%, about 85% to about 90%, or about 90% to about 95%.

Peptides of the disclosure include peptides that have been modified in any way and for any reason, for example, to: (1) reduce susceptibility to proteolysis, (2) alter binding affinities, and (3) confer or modify other physicochemical or functional properties. For example, single or multiple amino acid substitutions (e.g., equivalent, conservative or non-conservative substitutions, deletions or additions) may be made in a sequence.

A conservative amino acid substitution refers to the substitution in a peptide of an amino acid with a functionally similar amino acid having similar properties, e.g., size, charge, hydrophobicity, hydrophilicity, and/or aromaticity. The following six groups each contain amino acids that are conservative substitutions for one another are found in Table 2.

TABLE 2 i. Alanine (A), Serine (S), and Threonine (T)
ii. Aspartic acid (D) and Glutamic acid (E)
iii. Asparagine (N) and Glutamine (Q)
iv. Arginine (R) and Lysine (K)
v. Isoleucine (I), Leucine (L), Methionine (M), and Valine (V)
vi. Phenylalanine (F), Tyrosine (Y), and Tryptophan (W)

Additionally, within the meaning of the term "equivalent amino acid substitution" as applied herein, one amino acid may be substituted for another, in one embodiment, within the groups of amino acids indicated herein below:

1. Amino acids with polar side chains (Asp, Glu, Lys, Arg, His, Asn, Gln, Ser, Thr, Tyr, and Cys,)
2. Amino acids with small nonpolar or slightly polar residues (Ala, Ser, Thr, Pro, Gly);
3. Amino acids with non-polar side chains (Gly, Ala, Val, Leu, Ile, Phe, Trp, Pro, and Met)
4. Amino acids with large, aliphatic, nonpolar residues (Met, Leu, Ile, Val, Cys, Norleucine (Nle), homocysteine)
5. Amino acids with aliphatic side chains (Gly, Ala Val, Leu, Ile)
6. Amino acids with cyclic side chains (Phe, Tyr, Trp, His, Pro)
7. Amino acids with aromatic side chains (Phe, Tyr, Trp)
8. Amino acids with acidic side chains (Asp, Glu)

9. Amino acids with basic side chains (Lys, Arg, His)
10. Amino acids with amide side chains (Asn, Gln)
11. Amino acids with hydroxy side chains (Ser, Thr)
12. Amino acids with sulphur-containing side chains (Cys, Met),
13. Neutral, weakly hydrophobic amino acids (Pro, Ala, Gly, Ser, Thr)
14. Hydrophilic, acidic amino acids (Gln, Asn, Glu, Asp), and
15. Hydrophobic amino acids (Leu, Ile, Val).

In some embodiments, the amino acid substitution is not a conservative amino acid substitution, e.g., is a non-conservative amino acid substitution. This class generally includes corresponding D-amino acids, homo-amino acids, N-alkyl amino acids, beta amino acids and other unnatural amino acids. The non-conservative amino acid substitutions still fall within the descriptions identified for the equivalent amino acid substitutions above [e.g. polar, nonpolar, etc.]. Examples of non-conservative amino acids are provided below.

Non limiting examples for alanine non-conservative amino acids are: D-alanine [Dala, (dA), a], N-Acetyl-3-(3, 4-dimethoxyphenyl)-D-alanine, N-Me-D-Ala-OH, N-Me-Ala-OH, H-β-Ala-β-naphthalene, L-(−)-2-Amino-3-ureidopropionic acid, (R)-(+)-α-Allylalanine, (S)-(−)-α-Allylalanine, D-2-Aminobutyric acid, L-2-Aminobutyric acid, DL-2-Aminobutyric acid, 2-Aminoisobutyric acid, α-Aminoisobutyric acid, (S)-(+)-2-Amino-4-phenylbutyric acid ethyl ester, Benzyl α-aminoisobutyrate, Abu-OH, Aib-OH, β-(9-anthryl)-Ala-OH, β-(3-benzothienyl)-Ala-OH, β-(3-benzothienyl)-D-Ala-OH, Cha-OH, Cha-OMe, β-(2-furyl)-Ala-OH, β-(2-furyl)-D-Ala-OH, β-iodo-Ala-OBzl, β-iodo-D-Ala-OBzl, 3-iodo-D-Ala-OMe, β-iodo-Ala-OMe, 1-Nal-OH, D-1-Nal-OH, 2-Nal-OH, D-2-Nal-OH, (R)-3-(2-naphthyl)-β-Ala-OH, (S)-3-(2-naphthyl)-β-Ala-OH, β-phenyl-Phe-OH, 3-(2-pyridyl)-Ala-OH, 3-(3-pyridyl)-Ala-OH, 3-(3-pyridyl)-D-Ala-OH, (S)-3-(3-pyridyl)-β-Ala-OH, 3-(4-pyridyl)-Ala-OH, 3-(4-pyridyl)-D-Ala-OH, β-(2-quinolyl)-Ala-OH, 3-(2-quinolyl)-DL-Ala-OH, 3-(3-quinolyl)-DL-Ala-OH, 3-(2-quinoxalyl)-DL-Ala-OH, β-(4-thiazolyl)-Ala-OH, β-(2-thienyl)-Ala-OH, β-(2-thienyl)-D-Ala-OH, β-(3-thienyl)-Ala-OH, β-(3-thienyl)-D-Ala-OH, 3-Chloro-D-alanine methyl ester, N-[(4-Chlorophenyl)sulfonyl]-β-alanine, 3-Cyclohexyl-D-alanine, 3-Cyclopentyl-DL-alanine, (−)-3-(3,4-Dihydroxyphenyl)-2-methyl-L-alanine, 3,3-Diphenyl-D-alanine, 3,3-Diphenyl-L-alanine, N—[(S)-(+)-1-(Ethoxycarbonyl)-3-phenylpropyl]-L-alanine, N-[1-(S)-(+)-Ethoxycarbonyl-3-phenylpropyl]-L-alanyl carboxyanhydride, N-(3-fluorobenzyl)alanine, N-(3-Indolylacetyl)-L-alanine, Methyl (RS)-2-(aminomethyl)-3-phenylpropionate, 3-(2-Oxo-1,2-dihydro-4-quinolinyl) alanine, 3-(1-Pyrazolyl)-L-alanine, 3-(2-Pyridyl)-D-alanine, 3-(2-Pyridyl)-L-alanine, 3-(3-Pyridyl)-L-alanine, 3-(4-Pyridyl)-D-alanine, 3-(4-Pyridyl)-L-alanine, 3-(2-Quinolyl)-DL-alanine, 3-(4-Quinolyl)-DL-alanine, D-styrylalanine, L-styrylalanine, 3-(2-Thienyl)-L-alanine, 3-(2-Thienyl)-DL-alanine, 3-(2-Thienyl)-DL-alanine, 3,3,3-Trifluoro-DL-alanine, N-Methyl-L-alanine, 3-Ureidopropionic acid, Aib-OH, Cha-OH, Dehydro-Ala-OMe, dehydro-Ala-OH, D-2-Nal-OH, β-Ala-ONp, β-Homoala-OH, β-D-Homoala-OH, β-Alanine, β-Alanine ethyl ester, β-Alanine methyl ester, (S)-diphenyl-β-Homoala-OH, (R)-4-(4-pyridyl)-β-Homoala-OH, (S)-4-(4-pyridyl)-β-Homoala-OH, β-Ala-OH, (S)-diphenyl-β-Homoala-OH, L-β-Homoalanine, (R)-4-(3-pyridyl)-β-Homoala-OH, α-methyl-α-naphthylalanine [Manap], N-methyl-cyclohexylalanine [Nmchexa], cyclohexylalanine [Chexa], N-methyl-cyclopentylalanine [Nmcpen], cyclopentylalanine [Cpen], N-methyl-α-naphthylalanine [Nmanap], α-naphthylalanine [Anap], L-N-methylalanine [Nmala], D-N-methylalanine [Dnmala], α-methyl-cyclohexylalanine [Mchexa], α-methyl-cyclopentylalanine [Mcpen]. Each possibility represents a separate embodiment.

Non limiting examples for arginine non-conservative amino acids are: homoarginine (hArg), N-methyl arginine (NMeArg), citruline, 2-amino-3-guanidinopropionic acid, N-iminoethyl-L-ornithine, Nω-monomethyl-L-arginine, Nω-nitro-L-arginine, D-arginine, 2-amino-3-ureidopropionic acid, Nω,ω-dimethyl-L-arginine, Nω-Nitro-D-arginine, L-α-methylarginine [Marg], D-α-methylarginine [Dmarg], L-N-methylarginine [Nmarg], D-N-methylarginine [Dnmarg], β-Homoarg-OH, L-Homoarginine, N-(3-guanidinopropyl)glycine [Narg], and D-arginine [Darg, (dR), r]. Each possibility represents a separate embodiment.

Non limiting examples for asparagine non-conservative amino acids are: L-α-methylasparagine [Masn], D-α-methylasparagine [Dmasn], L-N-methylasparagine [Nmasn], D-N-methylasparagine [Dnmasn], N-(carbamylmethyl)glycine [Nasn] and D-asparagine [Dasn, (dN), n]. Each possibility represents a separate embodiment.

Non limiting examples for aspartic acid non-conservative amino acids are: L-α-methylaspartate [Masp], D-α-methylaspartate [Dmasp], L-N-methylaspartic acid [Nmasp], D-N-methylasparatate [Dnmasp], N-(carboxymethyl)glycine [Nasp] and D-aspartic acid [Dasp, (dD), d]. Each possibility represents a separate embodiment.

Non limiting examples for cysteine non-conservative amino acids are: L-Cysteic acid, L-Cysteinesulfinic acid, D-Ethionine, S-(2-Thiazolyl)-L-cysteine, DL-Homocysteine, L-Homocysteine, L-Homocystine, L-α-methylcysteine [Mcys], D-α-methylcysteine [Dmcys], L-N-methylcysteine [Nmcys], D-N-methylcysteine [Dnmcys], N-(thiomethyl)glycine [Ncys] and D-cysteine [Dcys, (dC), c]. Each possibility represents a separate embodiment.

Non limiting examples for glutamic acid non-conservative amino acids are: γ-Carboxy-DL-glutamic acid, 4-Fluoro-DL-glutamic acid, β-Glutamic acid, L-β-Homoglutamic acid, L-α-methylglutamate [Mglu], D-α-methyl glutamic acid [Dmglu], L-N-methylglutamic acid [Nmglu], D-N-methylglutamate [Dnmglu], N-(2-carboxyethyl)glycine [Nglu], and D-glutamic acid [Dglu, (dE), e]. Each possibility represents a separate embodiment.

Non limiting examples for glutamine non-conservative amino acids are: Cit-OH, D-Citrulline, Thio-L-citrulline, β-Gln-OH, L-β-Homoglutamine, L-α-methylglutamine [Mgln], D-α-methylglutamine [Dmgln], L-N-methylglutamine [Nmgln], D-N-methylglutamine [Dnmgln], N-(2-carbamylethyl)glycine [Ngln], and D-glutamine [Dgln, (dQ), q]. Each possibility represents a separate embodiment.

Non limiting examples for glycine non-conservative amino acids are: tBu-Gly-OH, D-Allylglycine, N-[Bis (methylthio)methylene]glycine methyl ester, Chg-OH, D-Chg-OH, D-cyclopropylglycine, L-cyclopropylglycine, (R)-4-fluorophenylglycine, (S)-4-fluorophenylglycine, iminodiacetic acid, (2-indanyl)-Gly-OH, (±)-α-phosphonoglycine trimethyl ester, D-propargylglycine, propargyl-Gly-OH, (R)-2-thienylglycine, (S)-2-thienylglycine, (R)-3-thienylglycine, (S)-3-thienylglycine, 2-(4-trifluoromethylphenyl)-DL-glycine, (2S,3R,4S)-α-(Carboxycyclopropyl) glycine, N-(Chloroacetyl)glycine ethyl ester, (S)-(+)-2-chlorophenylglycine methyl ester, N-(2-chlorophenyl)-N-(methylsulfonyl)glycine, D-α-Cyclohexylglycine, L-α-Cyclopropylglycine, Di-tert-butyl-iminodicarboxylate, Ethyl acetamidocyanoacetate, N-(2-fluorophenyl)-N-(methylsulfonyl) glycine, N-(4-fluorophenyl)-N-(methylsulfonyl) glycine, N-(2-Furfurylideneacetyl)glycine methyl ester, N-(2-Furoyl)glycine, N-(2-Hydroxyethyl)iminodiacetic acid, N-(4-Hydroxyphenyl)glycine, Iminodiacetic acid, N-Lauroylsarcosine sodium salt, L-α-Neopentylglycine, N-(Phosphonomethyl)glycine, D-Propargylglycine, L-C-Propargylglycine, Sarcosine, N,N-Dimethylglycine, N,N-Dimethylglycine ethyl ester, D-Chg-OH, α-Phosphonoglycine trimethyl ester, N-cyclobutylglycine [Ncbut], L-α-methylethylglycine [Metg], N-cycloheptylglycine [Nchep], L-α-methyl-i-butylglycine [Mtbug], N-methylglycine [Nmgly], L-N-methyl-ethylglycine [Nmetg], L-ethylglycine [Etg], L-N-methyl-t-butylglycine [Nmtbug], L-t-butylglycine [Tbug], N-cyclohexylglycine [Nchex], N-cyclodecylglycine [Ncdec], N-cyclododecylglycine [Ncdod], N-cyclooctylglycine [Ncoct], N-cyclopropylglycine [Ncpro], N-cycloundecylglycine [Ncund], N-(2-aminoethyl) glycine [Naeg], N—(N-(2,2-diphenylethyl) diphenylethyl) glycine [Nnbhm], N-(2,2-carbamylmethyl-glycine [Nbhm], N—(N-(3,3-diphenylpropyl) diphenylpropyl)glycine [Nnbhe] and N-(3,3-carbamylmethyl-glycine [Nbhe]. Each possibility represents a separate embodiment.

Non limiting examples for histidine non-conservative amino acids are: L-α-methylhistidine [Mhis], D-α-methylhistidine [Dmhis], L-N-methylhistidine [Nmhis], D-N-methylhistidine [Dnmhis], N-(imidazolylethyl)glycine [Nhis], and D-histidine [Dhis, (dH), h]. Each possibility represents a separate embodiment.

Non limiting examples for isoleucine non-conservative amino acids are: N-Methyl-L-isoleucine [Nmile], N-(3-Indolylacetyl)-L-isoleucine, allo-Ile-OH, D-allo-Isoleucine, L-β-Homoisoleucine, L-α-methylisoleucine [Mile], D-α-methylisoleucine [Dmile], D-N-methylisoleucine [Dnmile], N-(1-methylpropyl)glycine [Nile], and D-isoleucine [Dile, (dD), i]. Each possibility represents a separate embodiment.

Non limiting examples for leucine non-conservative amino acids are: D-leuine [Dleu, (dL), l]. Cycloleucine, DL-leucine, N-Formyl-Leu-OH, D-tert-Leucine, L-tert-Leucine, DL-tert-Leucine, L-tert-Leucine methyl ester, 5,5,5-Trifluoro-DL-leucine, D-β-Leu-OH, L-β-Leucine, DL-β-Leucine, L-β-Homoleucine, DL-β-Homoleucine, L-N-methyl-leucine [Nmleu], D-N-methyl-leucine [Dnmleu], L-α-methyl-leucine [Mleu], D-α-methyl-leucine [Dmleu], N-(2-methylpropyl)glycine [Nleu], D-leucine [Dleu, l], D-Norleucine, L-Norleucine, DL-Norleucine, L-N-methyl-norleucine [Nmnle] and L-norleucine [Nle]. Each possibility represents a separate embodiment.

Non limiting examples for lysine non-conservative amino acids are: DL-5-Hydroxylysine, (5R)-5-Hydroxy-L-lysine, β-Lys-OH, L-β-Homolysine, L-α-methyl-lysine [Mlys], D-α-methyl-lysine [Dmlys], L-N-methyl-lysine [Nmlys], D-N-methyl-lysine [Dnmlys], N-(4-aminobutyl)glycine [Nlys], and D-lysine [Dlys, (dK), k]. Each possibility represents a separate embodiment.

Non limiting examples for methionine non-conservative amino acids are: L-β-Homomethionine, DL-β-Homomethionine, L-α-methylmethionine [Mmet], D-α-methylmethionine [Dmmet], L-N-methylmethionine [Nmmet], D-N-methylmethionine [Dnmmet], N-(2-methylthioethyl)glycine [Nmet], and D-methionine [Dmet, (dM), m]. Each possibility represents a separate embodiment.

Non limiting examples for phenylalanine non-conservative amino acids are: N-Acetyl-2-fluoro-DL-phenylalanine, N-Acetyl-4-fluoro-DL-phenylalanine, 4-Amino-L-phenylalanine, 3-[3,4-bis(trifluoromethyl)phenyl]-L-alanine, Bpa-OH, D-Bpa-OH, 4-tert-butyl-Phe-OH, 4-tert-butyl-D-Phe-OH, 4-(amino)-L-phenylalanine, rac-$β^2$-homophenylalanine, 2-methoxy-L-phenylalanine, (S)-4-methoxy-β-Phe-OH, 2-nitro-L-phenylalanine, pentafluoro-D-phenylalanine, pentafluoro-L-phenylalanine, Phe(4-Br)—OH, D-Phe(4-Br)—OH, Phe(2-$CF_3$)—OH, D-Phe(2-$CF_3$)—OH, Phe(3-$CF_3$)—OH, D-Phe(3-$CF_3$)—OH, Phe(4-$CF_3$)—OH, D-Phe(4-$CF_3$)—OH, Phe(2-Cl)—OH, D-Phe(2-Cl)—OH, Phe(2,4-$Cl_2$)—OH, D-Phe(2,4-$Cl_2$)—OH, D-Phe(3-Cl)—OH, Phe(3,4-$Cl_2$)—OH, Phe(4-Cl)—OH, D-Phe(4-Cl)—OH, Phe(2-CN)—OH, D-Phe(2-CN)—OH, D-Phe(3-CN)—OH, Phe(4-CN)—OH, D-Phe(4-CN)—OH, Phe(2-Me)-OH, D-Phe(2-Me)-OH, Phe(3-Me)-OH, D-Phe(3-Me)-OH, Phe(4-Me)-OH, Phe(4-$NH_2$)—OH, Phe(4-$NO_2$)—OH, Phe(2-F)—OH, D-Phe(2-F)—OH, Phe(3-F)—OH, D-Phe(3-F)—OH, Phe(3,4-$F_2$)—OH, D-Phe(3,4-$F_2$)—OH, Phe(3,5-$F_2$)—OH, Phe(4-F)—OH, D-Phe(4-F)—OH, Phe(4-I)—OH, D-3,4,5-trifluorophenylalanine, p-Bromo-DL-phenylalanine, 4-Bromo-L-phenylalanine, β-phenyl-D-phenylalanine, 4-Chloro-L-phenylalanine, DL-2,3-Difluorophenylalanine, DL-3,5-Difluorophenylalanine, 3,4-Dihydroxy-L-phenylalanine, 3-(3,4-Dimethoxyphenyl)-L-alanine, N-[(9H-Fluoren-9-ylmethoxy)carbonyl]-2-methoxy-L-phenylalanine, o-Fluoro-DL-phenylalanine, m-Fluoro-L-phenylalanine, m-Fluoro-DL-phenylalanine, p-Fluoro-L-phenylalanine, p-Fluoro-DL-phenylalanine, 4-Fluoro-D-phenylalanine, 2-Fluoro-L-phenylalanine methyl ester, p-fluoro-DL-Phe-OMe, D-3-bromophenylalanine, D-4-bromophenylalanine, L-β-(6-chloro-4-pyridinyl)alanine, D-3,5-difluorophenylalanine, L-3-fluorophenylalanine, L-4-fluorophenylalanine, L-β-(1H-5-indolyl)alanine, 2-nitro-L-phenylalanine, pentafluoro-L-phenylalanine, phe(3-br)-oh, Phe(4-Br)—OH, Phe(2-$CF_3$)—OH, D-Phe(2-$CF_3$)—OH, Phe(3-$CF_3$)—OH, D-Phe(3-$CF_3$)—OH, Phe(4-$CF_3$)—OH, D-Phe(4-$CF_3$)—OH, Phe(2-Cl)—OH, D-Phe(2-Cl)—OH, Phe(2,4-$Cl_2$)—OH, D-Phe(2,4-$Cl_2$)—OH, Phe(3,4-$Cl_2$)—OH, D-Phe(3,4-$Cl_2$)—OH, Phe(4-Cl)—OH, D-Phe(4-Cl)—OH, Phe(2-CN)—OH, D-Phe(2-CN)—OH, D-Phe(3-CN)—OH, Phe(4-CN)—OH, Phe(2-Me)-OH, Phe(3-Me)-OH, D-Phe(3-Me)-OH, Phe(4-$NO_2$)—OH, D-Phe(4-$NO_2$)—OH, D-Phe(2-F)—OH, Phe(3-F)—OH, D-Phe(3-F)—OH, Phe(3,4-$F_2$)—OH, Phe(3,5-$F_2$)—OH, D-Phe(4-F)—OH, Phe(4-I)—OH, D-Phe(4-I)—OH, 4-(phosphonomethyl)-Phe-OH, L-trifluoromethylphenylalanine, 3,4,5-trifluoro-D-phenylalanine, L-3,4,5-trifluorophenylalanine, 6-Hydroxy-DL-DOPA, 4-(Hydroxymethyl)-D-phenylalanine, N-(3-Indolylacetyl)-L-phenylalanine, p-Iodo-D-phenylalanine, 4-Iodo-L-phenylalanine, α-Methyl-D-phenylalanine, α-Methyl-L-phenylalanine, α-Methyl-DL-phenylalanine, α-Methyl-DL-phenylalanine methyl ester, 4-Nitro-D-phenylalanine, 4-Nitro-L-phenylalanine, 4-Nitro-DL-phenylalanine, (S)-(+)-4-Nitrophenylalanine methyl ester, 2-(Trifluoromethyl)-D-phenylalanine, 2-(Trifluoromethyl)-L-phenylalanine, 3-(Trifluoromethyl)-D-phenylalanine, 3-(Trifluoromethyl)-L-phenylalanine, 4-(Trifluoromethyl)-D-phenylalanine, 3,3',5-Triiodo-L-thyronine, (R)-4-bromo-β-Phe-OH, N-Acetyl-DL-β-phenylalanine, (S)-4-bromo-3-Phe-OH, (R)-4-chloro-β-Homophe-OH, (S)-4-chloro-3-Homophe-OH, (R)-4-chloro-J-Phe-OH, (S)-4-chloro-β-Phe-OH, (5)-2-cyano-β-Homophe-OH, (R)-4-cyano-β-Homophe-OH, (S)-4-cyano-β-Homophe-OH, (R)-3-cyano-β-Phe-OH, (R)-4-cyano-3-Phe-OH, (S)-4-cyano-β-Phe-OH, (R)-3,4-dimethoxy-β-Phe-OH, (S)-3,4-dimethoxy-β-Phe-OH, (R)-4-fluoro-β-Phe-OH, (S)-4-fluoro-β-Phe-OH, (S)-4-iodo-β-Homophe-OH, (S)-3-cyano-β-Homophe-OH, (S)-3,4-difluoro-β-Homophe-OH, (R)-4-fluoro-β-Homophe-OH, (S)-β2-homophenylalanine, (R)-3-methoxy-β-Phe-OH, (S)-3-methoxy-β-Phe-OH, (R)-4-methoxy-β-Phe-OH, (S)-4-methyl-β-Homophe-OH, (R)-2- methyl-β-Phe-OH, (S)-2-methyl-β-Phe-OH, (R)-3-methyl-β-Phe-OH, (S)-3-methyl-β-Phe-OH, (R)-4-methyl-β-Phe-OH, (S)-4-methyl-β-Phe-OH, β-Phe-OH, D-β-Phe-OH, (S)-2-(trifluoromethyl)-β-Homophe-OH, (S)-2-(trifluoromethyl)-β-Homophe-OH, (S)-3-(trifluoromethyl)-β-Homophe-OH, (R)-4-(trifluoromethyl)-β-Homophe-OH, (S)-2-(trifluoromethyl)-β-Phe-OH, (R)-3-(trifluoromethyl)-β-Phe-OH, (S)-3-(trifluoromethyl)-β-Phe-OH, (R)-4-(trifluoromethyl)-β-Phe-OH, (S)-4-(trifluoromethyl)-β-Phe-OH, β-Homophe-OH, D-β-Homophe-OH, (S)-2-methyl-β-Homophe-OH, (S)-3-methyl-β-Homophe-OH, β-Phe-OH, β-D-Phe-OH, (S)-3-(trifluoromethyl)-β-Homophe-OH, L-β-Homophenylalanine, DL-β-Homophenylalanine, DL-β3-Phenylalanine, DL-homophenylalanine methyl ester, D-Homophenylalanine, L-Homophenylalanine, DL-Homophenylalanine, D-Homophenylalanine ethyl ester, (R)-β$^2$-homophenylalanine, L-α-methyl-homophenylalanine [Mhphe], L-α-methylphenylalanine [Mphe], D-α-methylphenylalanine [Dmphe], L-N-methyl-homophenylalanine [Nm phe], L-homophenylalanine [Hphe], L-N-methylphenylalanine [Nmphe], D-N-methylphenylalanine [Dnmphe], N-benzylglycine [Nphe] and D-phenylalanine [Dphe, (dF), f]. Each possibility represents a separate embodiment.

Non limiting examples for proline non-conservative amino acids are: homoproline (hPro), (4-hydroxy)Pro (4HyP), (3-hydroxy)Pro (3HyP), gamma-benzyl-proline, gamma-(2-fluoro-benzyl)-proline, gamma-(3-fluoro-benzyl)-proline, gamma-(4-fluoro-benzyl)-proline, gamma-(2-chloro-benzyl)-proline, gamma-(3-chloro-benzyl)-proline, gamma-(4-chloro-benzyl)-proline, gamma-(2-bromo-benzyl)-proline, gamma-(3-bromo-benzyl)-proline, gamma-(4-bromo-benzyl)-proline, gamma-(2-methyl-benzyl)-proline, gamma-(3-methyl-benzyl)-proline, gamma-(4-methyl-benzyl)-proline, gamma-(2-nitro-benzyl)-proline, gamma-(3-nitro-benzyl)-proline, gamma-(4-nitro-benzyl)-proline, gamma-(l-naphthalenylmethyl)-proline, gamma-(2-naphthalenylmethyl)-proline, gamma-(2,4-dichloro-benzyl)-proline, gamma-(3,4-dichloro-benzyl)-proline, gamma-(3,4-difluoro-benzyl)-proline, gamma-(2-trifluoro-methyl-benzyl)-proline, gamma-(3-trifluoro-methyl-benzyl)-proline, gamma-(4-trifluoro-methyl-benzyl)-proline, gamma-(2-cyano-benzyl)-proline, gamma-(3-cyano-benzyl)-proline, gamma-(4-cyano-benzyl)-proline, gamma-(2-iodo-benzyl)-proline, gamma-(3-iodo-benzyl)-proline, gamma-(4-iodo-benzyl)-proline, gamma-(3-phenyl-allyl-benzyl)-proline, gamma-(3-phenyl-propyl-benzyl)-proline, gamma-(4-tert-butyl-benzyl)-proline, gamma-benzhydryl-proline, gamma-(4-biphenyl-methyl)-proline, gamma-(4-thiazolyl-methyl)-proline, gamma-(3-benzothienyl-methyl)-proline, gamma-(2-thienyl-methyl)-proline, gamma-(3-thienyl-methyl)-proline, gamma-(2-furanyl-methyl)-proline, gamma-(2-pyridinyl-methyl)-proline, gamma-(3-pyridinyl-methyl)-proline, gamma-(4-pyridinyl-methyl)-proline, gamma-allyl-proline, gamma-propynyl-proline, alpha-modified-proline residues, pipecolic acid, azetidine-3-carboxylicacid, L-β-Homoproline, L-β$^3$-homoproline, L-β-Homohydroxyproline, hydroxyproline [Hyp], L-α-methylproline [Mpro], D-α-methylproline [Dmpro], L-N-methylproline [Nmpro], D-N-methylproline [Dnmpro], and D-proline [Dpro, (dP), p]. Each possibility represents a separate embodiment.

Non limiting examples for serine non-conservative amino acids are: (2R,3S)-3-phenylisoserine, D-cycloserine, L-Isoserine, DL-Isoserine, DL-3-Phenylserine, L-β-Homoserine, D-Homoserine, D-Homoserine, L-3-Homoserine, L-homoserine, L-α-methylserine [Mser], D-α-methylserine [Dmser], L-N-methylserine [Nmser], D-N-methylserine [Dnmser], D-serine [Dser, (dS), s], N-(hydroxymethyl)glycine [Nser] and phosphoserine [pSer]. Each possibility represents a separate embodiment.

Non limiting examples for threonine non-conservative amino acids are: L-allo-Threonine, D-Thyroxine, L-p-Homothreonine, L-α-methylthreonine [Mthr], D-α-methylthreonine [Dmthr], L-N-methylthreonine [Nmthr], D-N-methylthreonine [Dnmthr], D-threonine [Dthr, (dT), t], N-(1-hydroxyethyl)glycine [Nthr] and phosphothreonine [pThr]. Each possibility represents a separate embodiment.

Non limiting examples for tryptophan non-conservative amino acids are: 5-Fluoro-L-tryptophan, 5-Fluoro-DL-tryptophan, 5-Hydroxy-L-tryptophan, 5-Methoxy-DL-tryptophan, L-abrine, 5-Methyl-DL-tryptophan, H-Tpi-OMe. β-Homotrp-OMe, L-β-Homotryptophan, L-α-methyltryptophan [Mtrp], D-α-methyltryptophan [Dmtrp], L-N-methyltryptophan [Nmtrp], D-N-methyltryptophan [Dnmtrp], N-(3-indolylethyl)glycine [Nhtrp], D-tryptophan [Dtrp, (dW), w]. Each possibility represents a separate embodiment.

Non limiting examples for tyrosine non-conservative amino acids are: 3,5 diiodotyrosine (3,5-dITyr), 3,5 diBromotyrosine (3,5-dBTyr), homotyrosine, D-tyrosine, 3-amino-L-tyrosine, 3-amino-D-tyrosine, 3-iodo-L-tyrosine, 3-iodo-D-tyrosine, 3-methoxy-L-tyrosine, 3-methoxy-D-tyrosine, L-thyroxine, D-thyroxine, L-thyronine, D-thyronine, O-methyl-L-tyrosine, O-methyl-D-tyrosine, D-thyronine, O-ethyl-L-tyrosine, O-ethyl-D-tyrosine, 3,5,3'-triiodo-L-thyronine, 3,5,3'-triiodo-D-thyronine, 3,5-diiodo-L-thyronine, 3,5-diiodo-D-thyronine, D-meta-tyrosine, L-meta-tyrosine, D-ortho-tyrosine, L-ortho-tyrosine, phenylalanine, substituted phaenylalanine, N-nitro phenylalanine, p-nitro phenylalanine, 3-chloro-Dtyr-oh, Tyr(3,5-diI), 3-Chloro-L-tyrosine, Tyr(3-NO$_2$)—OH, Tyr(3,5-diI)—OH, N-Me-Tyr-OH, α-Methyl-DL-tyrosine, 3-Nitro-L-tyrosine, DL-o-Tyrosine, β-Homotyr-OH, (R)-β-Tyr-OH, (S)-β-Tyr-OH, L-α-methyltyrosine [Mtyr], D-α-methyltyrosine [Dmtyr], L-N-methyltyrosine [Nmtyr], D-N-methyltyrosine [Dnmtyr], D-tyrosine [Dtyr, (dY), y], O-methyl-tyrosine, and phosphotyrosine [pTyr]. Each possibility represents a separate embodiment.

Non limiting examples for valine non-conservative amino acids are: 3-Fluoro-DL-valine, 4,4,4,4',4',4'-Hexafluoro-DL-valine, D-valine [Dval, (dV), v], N-Me-Val-OH [Nmval], N-Me-Val-OH, L-α-methylvaline [Mval], D-α-methylvaline [Dmval], (R)-(+)-α-Methylvaline, (S)-(−)-α-Methylvaline and D-N-methylvaline [Dnmval]. Each possibility represents a separate embodiment.

Other non-natural amino acids that may be substituted as non-conservative replacements include: Ornithine and its modifications: D-Ornithine [Dorn], L-Ornithine [Orn], DL-Ornithine, L-α-methylornithine [Morn], D-α-methylornithine [Dmorn], L-N-methylornithine [Nmorn], D-N-methylornithine [Dnmorn] and N-(3-aminopropyl)glycine [Norn]. Each possibility represents a separate embodiment.

Alicyclic amino acids: L-2,4-Diaminobutyric acid, L-2,3-Diaminopropionic Acid, N-Me-Aib-OH, (R)-2-(amino)-5-hexynoic acid, piperidine-2-carboxylic acid, aminonorbornyl-carboxylate [Norb], alpha-aminobutyric acid [Abu], aminocyclopropane-carboxylate [Cpro], (cis)-3-Aminobicyclo[2.2.1]heptane-2-carboxylic acid, exo-cis-3-Aminobicyclo[2.2.1]hept-5-ene-2-carboxylic acid, 1-Amino-1-cyclobutanecarboxylic acid, cis-2-Aminocycloheptanecarboxylic acid, 1-Aminocyclohexanecarboxylic acid, cis-2-Aminocyclohexanecarboxylic acid, trans-2-Aminocyclohexanecarboxylic acid, cis-6-Amino-3-cyclohexene-1-carboxylic acid, 2-(1-Aminocyclohexyl)acetic acid, cis-2-Amino-1-cyclooctanecarboxylic acid, cis-2-Amino-3-cyclooctene-1-carboxylic acid, (1R,2S)-(−)-2-Amino-1-cyclopentanecarboxylic acid, (1S,2R)-(+)-2-Amino-1-cyclopentanecarboxylic acid, cis-2-Amino-1-cyclopentanecarboxylic acid, 2-(1-Aminocyclopentyl)acetic acid, cis-2-Amino-2-methylcyclohexanecarboxylic acid, cis-2-Amino-2-methylcyclopentanecarboxylic acid, 3-Amino-3-(4-nitrophenyl)propionic acid, 3-Azetidinecarboxylic acid, amchc-oh, 1-aminocyclobutane carboxylic acid, 1-(amino)cyclohexanecarboxylic acid, cis-2-(amino)-cyclohexanecarboxylic acid, trans-2-(amino)-cyclohexanecarboxylic acid, cis-4-(amino)cyclohexanecarboxylic acid, trans-4-(amino)cyclohexanecarboxylic acid, (±)-cis-2-(amino)-3-cyclohexene-1-carboxylic acid, (±)-cis-6-(amino)-3-cyclohexene-1-carboxylic acid, 2-(1-aminocyclohexyl)acetic acid, cis-[4-(amino)cyclohexyl]acetic acid, 1-(amino)cyclopentanecarboxylic acid, (±)-cis-2-(amino) cyclopentanecarboxylic acid, (1R,4S)-(+)-4-(amino)-2-cyclopentene-1-carboxylic acid, (±)-cis-2-(amino)-3-cyclopentene-1-carboxylic acid, 2-(1-aminocyclopentyl)acetic acid, 1-(amino)cyclopropanecarboxylic acid, Ethyl 1-aminocyclopropanecarboxylate, 1,2-trans-achec-oh, 1-(amino) cyclobutanecarboxylic acid, 1-(amino)cyclohexanecarboxylic acid, cis-2-(amino)-cyclohexanecarboxylic acid, trans-2-(amino)cyclohexanecarboxylic acid, cis-4-(amino) cyclohexanecarboxylic acid, trans-4-(amino) cyclohexanecarboxylic acid, cis-[4-(amino)cyclohexyl] acetic acid, 1-(amino)cyclopentanecarboxylic acid, (1R,4S)-(+)-4-(amino)-2-cyclopentene-1-carboxylic acid, (1S,4R)-(−)-4-(amino)-2-cyclopentene-1-carboxylic acid, 1-(amino) cyclopropanecarboxylic acid, trans-4-(aminomethyl) cyclohexanecarboxylic acid, D-Dab-OH, 3-Amino-3-(3-bromophenyl)propionic acid, 3-Aminobutanoic acid, cis-2-Amino-3-cyclopentene-1-carboxylic acid, DL-3-Aminoisobutyric acid, (R)-3-Amino-2-phenylpropionic acid, (±)-3-(amino)-4-(4-biphenylyl)butyric acid, cis-3-(amino)cyclohexanecarboxylic acid, (1S,3R)-(+)-3-(amino) cyclopentanecarboxylic acid, (2R,3R)-3-(amino)-2-hydroxy-4-phenylbutyric acid, (2S,3R)-3-(amino)-2-hydroxy-4-phenylbutyric acid, 2-(aminomethyl)phenylacetic acid, (R)-3-(amino)-2-methylpropionic acid, (S)-3-(amino)-2-methylpropionic acid, (R)-3-(amino)-4-(2-naphthyl)butyric acid, (S)-3-(amino)-4-(2-naphthyl)butyric acid, (R)-3-(amino)-5-phenylpentanoic acid, (R)-3-(amino)-2-phenylpropionic acid, Ethyl 3-(benzylamino)propionate, cis-3-(amino)cyclohexanecarboxylic acid, (S)-3-(amino)-5-hexenoic acid, (R)-3-(amino)-2-methylpropionic acid, (S)-3-(amino)-2-methylpropionic acid, (R)-3-(amino)-4-(2-naphthyl)butyric acid, (S)-3-(amino)-4-(2-naphthyl)butyric acid, (R)-(−)-Pyrrolidine-3-carboxylic acid, (S)-(+)-Pyrrolidine-3-carboxylic acid, N-methyl-γ-aminobutyrate [Nmgabu], γ-aminobutyric acid [Gabu], N-methyl-α-amino-α-methylbutyrate [Nmaabu], α-amino-α-methylbutyrate [Aabu], N-methyl-α-aminoisobutyrate [Nmaib], α-aminoisobutyric acid [Aib], α-methyl-γ-aminobutyrate [Mgabu]. Each possibility represents a separate embodiment.

Phenyl glycine and its modifications: Phg-OH, D-Phg-OH, 2-(piperazino)-2-(3,4-dimethoxyphenyl)acetic acid, 2-(piperazino)-2-(2-fluorophenyl)acetic acid, 2-(4-piperazino)-2-(3-fluorophenyl)acetic acid, 2-(4-piperazino)-2-(4-methoxyphenyl)acetic acid, 2-(4-piperazino)-2-(3-pyridyl) acetic acid, 2-(4-piperazino)-2-[4-(trifluoromethyl)phenyl] acetic acid, L-(+)-2-Chlorophenylglycine, (±)-2-Chlorophenylglycine, (±)-4-Chlorophenylglycine, (R)-(−)-2-(2,5-Dihydrophenyl)glycine, (R)-(−)-N-(3,5-Dinitrobenzoyl)-α-phenylglycine, (S)-(+)-N-(3,5-Dinitrobenzoyl)-α-phenylglycine, 2,2-Diphenylglycine, 2-Fluoro-DL-α-phenylglycine, 4-Fluoro-D-α-phenylglycine, 4-Hydroxy-D-phenylglycine, 4-Hydroxy-L-phenylglycine, 2-Phenylglycine, D-(−)-α-Phenylglycine, D-(−)-α-Phenylglycine, DL-α-Phenylglycine, L-(+)-α-Phenylglycine, N-Phenylglycine, (R)-(−)-2-Phenylglycine methyl ester, (S)-(+)-2-Phenylglycine methyl ester, 2-Phenylglycinonitrile hydrochloride, α-Phenylglycinonitrile, 3-(Trifluoromethyl)-DL-phenylglycine, and 4-(Trifluoromethyl)-L-phenylglycine. Each possibility represents a separate embodiment.

Penicillamine and its modifications: N-Acetyl-D-penicillamine, D-Penicillamine, L-Penicillamine [Pen], DL-Penicillamine. α-methylpenicillamine [Mpen], N-methylpenicillamine [Nmpen]. Each possibility represents a separate embodiment.

β-Homopyrrolidine. Each possibility represents a separate embodiment.

Aromatic amino acids: 3-Acetamidobenzoic acid, 4-Acetamidobenzoic acid, 4-Acetamido-2-methylbenzoic acid, N-Acetylanthranilic acid, 3-Aminobenzoic acid, 3-Aminobenzoic acid hydrochloride, 4-Aminobenzoic acid, 4-Aminobenzoic acid, 4-Aminobenzoic acid, 4-Aminobenzoic acid, 4-Aminobenzoic acid, 4-Aminobenzoic acid, 4-Aminobenzoic acid, 2-Aminobenzophenone-2'-carboxylic acid, 2-Amino-4-bromobenzoic acid, 2-Amino-5-bromobenzoic acid, 3-Amino-2-bromobenzoic acid, 3-Amino-4-bromobenzoic acid, 3-Amino-5-bromobenzoic acid, 4-Amino-3-bromobenzoic acid, 5-Amino-2-bromobenzoic acid, 2-Amino-3-bromo-5-methylbenzoic acid, 2-Amino-3-chlorobenzoic acid, 2-Amino-4-chlorobenzoic acid, 2-Amino-5-chlorobenzoic acid, 2-Amino-5-chlorobenzoic acid, 2-Amino-6-chlorobenzoic acid, 3-Amino-2-chlorobenzoic acid, 3-Amino-4-chlorobenzoic acid, 4-Amino-2-chlorobenzoic acid, 4-Amino-3-chlorobenzoic acid, 5-Amino-2-chlorobenzoic acid, 5-Amino-2-chlorobenzoic acid, 4-Amino-5-chloro-2-methoxybenzoic acid, 2-Amino-5-chloro-3-methylbenzoic acid, 3-Amino-2,5-dichlorobenzoic acid, 4-Amino-3,5-dichlorobenzoic acid, 2-Amino-4,5-dimethoxybenzoic acid, 4-(2-Aminoethyl) benzoic acid hydrochloride, 2-Amino-4-fluorobenzoic acid, 2-Amino-5-fluorobenzoic acid, 2-Amino-6-fluorobenzoic acid, 4-Amino-2-fluorobenzoic acid, 2-Amino-5-hydroxybenzoic acid, 3-Amino-4-hydroxybenzoic acid, 4-Amino-3-hydroxybenzoic acid, 2-Amino-5-iodobenzoic acid, 5-Aminoisophthalic acid, 2-Amino-3-methoxybenzoic acid, 2-Amino-4-methoxybenzoic acid, 2-Amino-5-methoxybenzoic acid, 3-Amino-2-methoxybenzoic acid, 3-Amino-4-methoxybenzoic acid, 3-Amino-5-methoxybenzoic acid, 4-Amino-2-methoxybenzoic acid, 4-Amino-3-methoxybenzoic acid, 5-Amino-2-methoxybenzoic acid, 2-Amino-3-methylbenzoic acid, 2-Amino-5-methylbenzoic acid, 2-Amino-6-methylbenzoic acid, 3-(Aminomethyl)benzoic acid, 3-Amino-2-methylbenzoic acid, 3-Amino-4-methylbenzoic acid, 4-(Aminomethyl)benzoic acid, 4-Amino-2-methylbenzoic acid, 4-Amino-3-methylbenzoic acid, 5-Amino-2-methylbenzoic acid, 3-Amino-2-naphthoic acid, 6-Amino-2-naphthoic acid, 2-Amino-3-nitrobenzoic acid, 2-Amino-5-nitrobenzoic acid, 2-Amino-5-nitrobenzoic acid, 4-Amino-3-nitrobenzoic acid, 5-Amino-2-nitrobenzoic acid, 3-(4-Aminophenyl)propionic acid, 3-Aminophthalic acid, 4-Aminophthalic acid, 3-Aminosalicylic acid, 4-Aminosalicylic acid, 5-Aminosalicylic acid, 5-Aminosalicylic acid, 2-Aminoterephthalic acid, 2-Amino-3,4,5,6-tetrafluorobenzoic acid, 4-Amino-2,3,5,6-tetrafluorobenzoic acid, (R)-2-Amino-1,2,3,4-tetrahydronaphthalene-2-carboxylic acid, (S)-2-Amino-1,2,3,4-tetrahydro-2-naphthalenecarboxylic acid, 2-Amino-3-(trifluoromethyl)benzoic acid, 2-Amino-3-

(trifluoromethyl)benzoic acid, 3-Amino-5-(trifluoromethyl) benzoic acid, 5-Amino-2,4,6-triiodoisophthalic acid, 2-Amino-3,4,5-trimethoxybenzoic acid, 2-Anilinophenylacetic acid, 2-Abz-OH, 3-Abz-OH, 4-Abz-OH, 2-(aminomethyl)benzoic acid, 3-(aminomethyl)benzoic acid, 4-(aminomethyl)benzoic acid, tert-Butyl 2-aminobenzoate, tert-Butyl 3-aminobenzoate, tert-Butyl 4-aminobenzoate, 4-(Butylamino)benzoic acid, 2,3-Diaminobenzoic acid, 3,4-Diaminobenzoic acid, 3,5-Diaminobenzoic acid, 3,5-Diaminobenzoic acid, 3,5-Dichloroanthranilic acid, 4-(Diethylamino)benzoic acid, 4,5-Difluoroanthranilic acid, 4-(Dimethylamino)benzoic acid, 4-(Dimethylamino)benzoic acid, 3,5-Dimethylanthranilic acid, 5-Fluoro-2-methoxybenzoic acid, 2-Abz-OH, 3-Abz-OH, 4-Abz-OH, 3-(aminomethyl)benzoic acid, 4-(aminomethyl)benzoic acid, 4-(2-hydrazino)benzoic acid, 3-Hydroxyanthranilic acid, 3-Hydroxyanthranilic acid, Methyl 3-aminobenzoate, 3-(Methylamino)benzoic acid, 4-(Methylamino)benzoic acid, Methyl 2-amino-4-chlorobenzoate, Methyl 2-amino-4,5-dimethoxybenzoate, 4-Nitroanthranilic acid, N-Phenylanthranilic acid, N-Phenylanthranilic acid, and Sodium 4-aminosalicylate. Each possibility represents a separate embodiment.

Other amino acids: (S)-α-Amino-γ-butyrolactone, DL-2-Aminocaprylic acid, 7-Aminocephalosporanic acid, 4-Aminocinnamic acid, (S)-(+)-α-Aminocyclohexanepropionic acid, (R)-Amino-(4-hydroxyphenyl)acetic acid methyl ester, 5-Aminolevulinic acid, 4-Amino-nicotinic acid, 3-Aminophenylacetic acid, 4-Aminophenylacetic acid, 2-Amino-2-phenylbutyric acid, 4-(4-Aminophenyl)butyric acid, 2-(4-Aminophenylthio)acetic acid, DL-α-Amino-2-thiopheneacetic acid, 5-Aminovaleric acid, 8-Benzyl (S)-2-aminooctanedioate, 4-(amino)-1-methylpyrrole-2-carboxylic acid, 4-(amino)tetrahydrothiopyran-4-carboxylic acid, (1R,3S,4S)-2-azabicyclo[2.2.1]heptane-3-carboxylic acid, L-azetidine-2-carboxylic acid, azetidine-3-carboxylic acid, 4-(amino)piperidine-4-carboxylic acid, diaminoacetic acid, Inp-OH, (R)-Nip-OH, (S)-4-oxopiperidine-2-carboxylic acid, 2-(4-piperazino)-2-(4-fluorophenyl)acetic acid, 2-(4-piperazino)-2-phenylacetic acid, 4-piperidineacetaldehyde, 4-piperidylacetic acid, (-)-L-thioproline, Tle-OH, 3-piperidinecarboxylic acid, L-(+)-Canavanine, (±)-Carnitine, Chlorambucil, 2,6-Diaminopimelic acid, meso-2,3-Diaminosuccinic acid, 4-(Dimethylamino)cinnamic acid, 4-(Dimethylamino)phenylacetic acid, Ethyl (S)—N-Boc-piperidine-3-carboxylate, Ethyl piperazinoacetate, 4-[2-(amino)ethyl]piperazin-1-ylacetic acid, (R)-4-(amino)-5-phenylpentanoic acid, (S)-azetidine-2-carboxylic acid, azetidine-3-carboxylic acid, guvacine, Inp-OH, (R)-Nip-OH, DL-Nip-OH, 4-phenyl-piperidine-4-carboxylic acid, 1-piperazineacetic acid, 4-piperidineacetic acid, (R)-piperidine-2-carboxylic acid, (S)-piperidine-2-carboxylic acid, (S)-1,2,3,4-tetrahydronorharmane-3-carboxylic acid, Tic-OH, D-Tic-OH, Iminodiacetic acid, Indoline-2-carboxylic acid, DL-Kynurenine, L-aziridine-2-carboxylate, Methyl 4-aminobutyrate, (S)-2-Piperazinecarboxylic acid, 2-(1-Piperazinyl)acetic acid, (R)-(-)-3-Piperidinecarboxylic acid, 2-Pyrrolidone-5-carboxylic acid, (R)-(+)-2-Pyrrolidone-5-carboxylic acid, (R)-1,2,3,4-Tetrahydro-3-isoquinolinecarboxylic acid, (S)-1,2,3,4-Tetrahydro-3-isoquinolinecarboxylic acid, L-4-Thiazolidinecarboxylic acid, (4R)-(-)-2-Thioxo-4-thiazolidinecarboxylic acid, hydrazinoacetic acid, and 3,3',5-Triiodo-L-thyronine. Each possibility represents a separate embodiment.

The present disclosure provides peptides comprising peptidomimetic compounds having further improved stability and cell permeability properties. Some embodiments comprise a peptide according to any of SEQ ID NO: 1-213, 230-236 and 239, wherein one of more peptide bonds (—CO—NH—) within the peptide may be substituted, for example, by N-methylated amide bonds (—N(CH$_3$)—CO—), ester bonds (—C(=O)—O—), ketomethylene bonds (—CO—CH$_2$—), sulfinylmethylene bonds (—S(=O)—CH$_2$—), α-aza bonds (—NH—N(R)—CO—), wherein R is any alkyl (e.g., methyl), amine bonds (—CH$_2$—NH—), sulfide bonds (—CH$_2$—S—), ethylene bonds (—CH$_2$—CH$_2$—), hydroxyethylene bonds (—CH(OH)—CH2-), thioamide bonds (—CS—NH—), olefinic double bonds (—CH=CH—), fluorinated olefinic double bonds (—CF=CH—), or retro amide bonds (—NH—CO—), peptide derivatives (—N(R$^x$)—CH$_2$—CO—), wherein R$^x$ is the "normal" side chain, naturally present on the carbon atom. These modifications can occur at any of the bonds along the peptide chain and even at several (2-3) bonds at the same time.

The peptides of some embodiments are preferably utilized in a linear form, although it will be appreciated that in cases where cyclization does not severely interfere with peptide characteristics, cyclic forms of the peptide can also be utilized and are contemplated as embodiments.

In exemplary embodiments, the peptide comprises any integer number of amino acids from 4 to 50, inclusive, connected via peptide bonds. For purposes of describing exemplary genera of peptides by size, all integer size ranges within the range of 4 to 50 amino acids are specifically contemplated. In some exemplary embodiments, the peptide comprises at least seven or eight amino acids connected via peptide bonds. In exemplary aspects, the peptide is at least about 4 amino acids in length, about 5 amino acids in length, about 6 amino acids in length, about 7 amino acids in length, or about 8 amino acids in length. In exemplary aspects, the peptide is at least about 9 amino acids in length, about 10 amino acids in length, about 11 amino acids in length, or about 12 amino acids in length. In exemplary aspects, the peptide is less than about 50 amino acids in length, less than about 40 amino acids, or less than about 30 amino acids, less than about 25 amino acids in length, or less than about 20 amino acids in length. In exemplary aspects, the peptide is about 4 to about 30 amino acids in length or about 5 to about 20 amino acids in length. In exemplary aspects, the peptide is about 6 to about 10 amino acids in length, about 5 to about 20 amino acids in length, about 4 to about 30 amino acids in length, or about 6 to about 16 amino acids in length. In exemplary aspects, the peptide is 4-5, 6-7, 7-8, 9-10, 11-12, 13-15, 14-15, 14-16, 15-16, 16-18, 16-19, 17-19, 18-19, 20-22, 22-24, 23-24, or 24-25 amino acids in length. In some embodiments, the peptide is a 4-mer, 5-mer, 6-mer, 7-mer, 8-mer, 9-mer, 10-mer, 11-mer, 12-mer, 13-mer, 14-mer, 15-mer, 16-mer, 17-mer, or 18-mer.

It is yet another object of the present invention to provide peptides comprising peptidomimetic compounds having further improved stability and cell permeability properties. Some embodiments of the invention comprises a peptide according to any of SEQ ID NO: 1-213, 230-236 and 239, wherein said peptide bonds (—CO—NH—) within the peptide may be substituted, for example, by N-methylated amide bonds (N-Me; —N(CH$_3$)—CO—), ester bonds (—C(=O)—O—), ketomethylene bonds (—CO—CH$_2$—), sulfinylmethylene bonds (—S(=O)—CH$_2$—), α-aza bonds (—NH—N(R)—CO—), wherein R is any alkyl (e.g., methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH=CH—), fluorinated olefinic double bonds (—CF═CH—), or retro amide bonds (—NH—CO—), peptide derivatives (—N(R$^x$)—CH$_2$—CO—), wherein R$^x$ is the "normal" side chain, naturally present on the carbon atom. These modifications can occur at any of the bonds along the peptide chain and even at several (2-3) bonds at the same time.

The present invention further provides conjugates comprising any of the peptides and analogs described herein conjugated to a moiety for extending half life or increasing cell penetration. For example, the half life extending moiety is a peptide or protein and the conjugate is a fusion peptide or chimeric peptide. Alternatively, the half life extending moiety is a polymer, e.g., a polyethylene glycol. The present disclosure furthermore provides dimers and multimers comprising any of the peptides and analogs described herein. Any moiety known in the art to facilitate actively or passively or enhance permeability of the compound into cells may be used for conjugation with the peptide core according to the present invention. Non-limitative examples include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides. According to a preferred embodiment, the hydrophobic moiety is a lipid moiety or an amino acid moiety. The permeability-enhancing moiety may be connected to any position in the peptide moiety, directly or through a spacer or linker, preferably to the amino terminus of the peptide moiety. The hydrophobic moiety according to the invention may preferably comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl (C$_3$); butanoyl (C$_4$); pentanoyl (C$_5$); caproyl (C$_6$); heptanoyl (C$_7$); capryloyl (C$_8$); nonanoyl (C$_9$); capryl (C$_{10}$); undecanoyl (C$_{11}$); lauroyl (C$_{12}$); tridecanoyl (C$_{13}$); myristoyl (C$_{14}$); pentadecanoyl (C$_{15}$); palmitoyl (C$_{16}$); phtanoyl ((CH$_3$)$_4$); heptadecanoyl (C$_{16}$); stearoyl (C$_{18}$); nonadecanoyl (C$_{19}$); arachidoyl (C$_{20}$); heniecosanoyl (C$_{21}$); behenoyl (C$_{22}$); trucisanoyl (C$_{23}$); and lignoceroyl (C$_{24}$); wherein said hydrophobic moiety is attached to said chimeric peptide or polypeptide with amide bonds, sulfhydryls, amines, alcohols, phenolic groups, or carbon-carbon bonds. Other examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((-N,N,N-trimethylammoniumethyl-aminocarbonylmethylene)ethylenediamine tetraiodide; N,N"-Bis(hexadecylaminocarbonylmethylene)-N,N',N"-tris((-N,N,N-trimethylammonium-ethylaminocarbonylmethylenediethylenetriamine hexaiodide; N,N'-Bis (dodecylaminocarbonylmethylene)-N,N"-bis((-N,N,N-trimethylammonium ethylaminocarbonylmethylene)cyclohexylene-1,4-diamine tetraiodide; 1,7,7-tetra-((-N,N,N-tetramethylammoniumethylamino-carbonylmethylene)-3-hexadecylarninocarbonyl-methylene-1,3,7-triaazaheptane heptaiodide; N,N,N',N'-tetra((-N,N,N-trimethylammonium-ethylaminocarbonylmethylene)-N'-(1,2-dioleoylglycero-3-phosphoethanolamino carbonylmethylene) diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl)methylamino)-octadecanoic acid; N-[12-(((7'-diethylaminocoumarin-3-yl)carbonyl)methyl-amino)octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-sn-3-succinyl-glycerol; 1,3-dipalmitoyl-2-succinylglycerol, 1-hexadecyl-2-palmitoylglycero-phosphoethanolamine, and palmitoylhomocysteine.

The peptides of the present invention may be attached (either covalently or non-covalently) to a penetrating agent. As used herein the phrase "penetrating agent" refers to an agent which enhances translocation of any of the attached peptide across a cell membrane. Typically, peptide based penetrating agents have an amino acid composition containing either a high relative abundance of positively charged amino acids such as lysine or arginine, or have sequences that contain an alternating pattern of polar/charged amino acids and non-polar, hydrophobic amino acids. By way of a non-limiting example, cell penetrating peptide (CPP) sequences may be used in order to enhance intracellular penetration. CPPs may include short and long versions of the protein transduction domain (PTD) of HIV TAT protein, such as for example, YARAAARQARA (SEQ ID NO: 214), YGRKKRR (SEQ ID NO: 215), YGRKKRRQRRR (SEQ ID NO: 216), or RRQRR (SEQ ID NO: 217)]. However, the disclosure is not so limited, and any suitable penetrating agent may be used, as known by those of skill in the art. Another method of enhancing cell penetration is via N-terminal myristoilation. In this protein modification, a myristoyl group (derived from myristic acid) is covalently attached via an amide bond to the alpha-amino group of an N-terminal amino acid of the peptide. Some technologies are described in. Soriaga, et al. "A Designed Inhibitor of p53 Aggregation Rescues p53 Tumor Suppression in Ovarian Carcinomas." Cancer Cell. 29. no. 1 (Jan. 11, 2016): 90-103. Other cell penetrating technology includes that found in patent publications WO2016102339; WO2014131892; WO2016087842; WO2014041505; WO2013098337, WO2010012850; WO2014147193; WO2014001229;

WO2015075747, WO2012090150, WO2014056813, WO2014009259 and WO2011157713.

According to some embodiments the peptide is modified, e.g it may include a duration enhancing moiety. The duration enhancing moiety can be a water soluble polymer, or a long chain aliphatic group. In some embodiments, a plurality of duration enhancing moieties are attached to the peptide, in which case each linker to each duration enhancing moiety is independently selected from the linkers described herein.

According to some embodiments the amino terminus of the peptide is modified, e.g., it may be acylated. According to additional embodiments the carboxy terminus is modified, e.g., it may be acylated, amidated, reduced or esterified. In accordance with some embodiments, the peptide comprises an acylated amino acid (e.g., a non-coded acylated amino acid (e.g., an amino acid comprising an acyl group which is non-native to a naturally-occurring amino acid)). In accordance with one embodiment, the peptide comprises an acyl group which is attached to the peptide via an ester, thioester, or amide linkage for purposes of prolonging half-life in circulation and/or delaying the onset of and/or extending the duration of action and/or improving resistance to proteases. Acylation can be carried out at any position within the peptide, (e.g., the amino acid at the C-terminus), provided that activity is retained, if not enhanced. The peptide in some embodiments can be acylated at the same amino acid position where a hydrophilic moiety is linked, or at a different amino acid position. The acyl group can be covalently linked directly to an amino acid of the peptide, or indirectly to an amino acid of the peptide via a spacer, wherein the spacer is positioned between the amino acid of the peptide and the acyl group.

In specific aspects, the peptide is modified to comprise an acyl group by direct acylation of an amine, hydroxyl, or thiol of a side chain of an amino acid of the peptide. In this regard, the acylated peptide can comprise the amino acid sequence of any of SEQ ID NO: 1-213, 230-236 and 239, or a modified amino acid sequence thereof comprising one or more of the amino acid modifications described herein.

In some embodiments, the peptide comprises a spacer between the analog and the acyl group. In some embodiments, the peptide is covalently bound to the spacer, which is covalently bound to the acyl group. In some embodiments, the spacer is an amino acid comprising a side chain amine, hydroxyl, or thiol, or a dipeptide or tripeptide comprising an amino acid comprising a side chain amine, hydroxyl, or thiol. The amino acid to which the spacer is attached can be any amino acid (e.g., a singly or doubly α-substituted amino acid) comprising a moiety which permits linkage to the spacer. For example, an amino acid comprising a side chain NH$_2$, —OH, or —COOH (e.g., Lys, Orn, Ser, Asp, or Glu) is suitable. In some embodiments, the spacer is an amino acid comprising a side chain amine, hydroxyl, or thiol, or a dipeptide or tripeptide comprising an amino acid comprising a side chain amine, hydroxyl, or thiol. When acylation occurs through an amine group of a spacer, the acylation can occur through the alpha amine of the amino acid or a side chain amine. In the instance in which the alpha amine is acylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp, Glu, homoglutamic acid, homocysteic acid, cysteic acid, gamma-glutamic acid. In the instance in which the side chain amine of the amino acid of the spacer is acylated, the amino acid of the spacer is an amino acid comprising a side chain amine. In this instance, it is possible for both the alpha amine and the side chain amine of the amino acid of the spacer to be acylated, such that the peptide is diacylated. Embodiments of the invention include such diacylated molecules. When acylation occurs through a hydroxyl group of a spacer, the amino acid or one of the amino acids of the dipeptide or tripeptide can be Ser. When acylation occurs through a thiol group of a spacer, the amino acid or one of the amino acids of the dipeptide or tripeptide can be Cys.

In a specific embodiment, the spacer comprises an amino poly(alkyloxy)carboxylate. In this regard, the spacer can comprise, for example, NH$_2$(CH$_2$CH$_2$O)$_n$(CH$_2$)$_m$COOH, wherein m is any integer from 1 to 6 and n is any integer from 2 to 12, such as, e.g., 8-amino-3,6-dioxaoctanoic acid, which is commercially available from Peptides International, Inc. (Louisville, Ky.). In some embodiments, the spacer is a hydrophobic bifunctional spacer. Hydrophobic bifunctional spacers are known in the art. See, e.g., *Bioconjugate Techniques*, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid. In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups. The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the acyl group is a C$_{12}$ to C$_{18}$ fatty acyl group, e.g., C$_{14}$ fatty acyl group, C$_{16}$ fatty acyl group, such that the total length of the spacer and acyl group is 14 to 28 atoms, e.g., about 14, 15, 16, 17, 18, 19, 20, 21, 22, 23, 24, 25, 26, 27, or 28 atoms. In some embodiments, the length of the spacer and acyl group is 17 to 28 (e.g., 19 to 26, 19 to 21) atoms. In accordance with certain foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring or coded and/or non-coded or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring or non-coded amino acids selected from the group consisting of: γ-alanine (β-Ala), N-α-methyl-alanine (Me-Ala), aminobutyric acid (Abu), γ-aminobutyric acid (7-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met($O_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe (4-Cl)), 4-fluorophenylalanine (Phe(4-F)), 4-nitrophenylalanine (Phe(4-$NO_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid. In some embodiments, the spacer comprises an overall negative charge, e.g., comprises one or two negative-charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the dipeptide spacer is selected from the group consisting of: Ala-Ala, β-Ala-β-Ala, Leu-Leu, Pro-Pro, γ-aminobutyric acid-γ-aminobutyric acid, Glu-Glu, and γ-Glu-γ-Glu.

Suitable methods of peptide acylation via amines, hydroxyls, and thiols are known in the art. See, for example, Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); Bioconjugate Chem. "Chemical Modifications of Proteins: History and Applications" pages 1, 2-12 (1990); Hashimoto et al., Pharmaceutical Res. "Synthesis of Palmitoyl Derivatives of Insulin and their Biological Activity" Vol. 6, No: 2 pp. 171-176 (1989). The acyl group of the acylated amino acid can be of any size, e.g., any length carbon chain, and can be linear or branched. In some specific embodiments, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a $C_{14}$ fatty acid or a $C_{16}$ fatty acid. In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid. In some embodiments, the peptide comprises an acylated amino acid by acylation of a long chain alkane on the peptide. In specific aspects, the long chain alkane comprises an amine, hydroxyl, or thiol group (e.g., octadecylamine, tetradecanol, and hexadecanethiol) which reacts with a carboxyl group, or activated form thereof, of the peptide. The carboxyl group, or activated form thereof, of the peptide can be part of a side chain of an amino acid (e.g., glutamic acid, aspartic acid) of the peptide or can be part of the analog backbone. In certain embodiments, the peptide is modified to comprise an acyl group by acylation of the long chain alkane by a spacer which is attached to the peptide. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers.

As used herein, the term "activated form" of a carboxyl group refers to a carboxyl group with the general formula R(C=))X, wherein X is a leaving group and R is the peptide or the spacer. For example, activated forms of a carboxyl groups may include, but are not limited to, acyl chlorides, anhydrides, and esters. In some embodiments, the activated carboxyl group is an ester with a N-hydroxysuccinimide ester (NHS) leaving group.

With regard to these aspects, in which a long chain alkane is acylated by the peptide or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

Also, in some embodiments, an amine, hydroxyl, or thiol group of the peptide is acylated with a cholesterol acid. In a specific embodiment, the peptide is linked to the cholesterol acid through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety. For clarification, des-amino-Cys is 3-mercaptopropionic acid.

The peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the peptide can of any of SEQ ID NOs: 1-213, 230-236 and 239, including any of the modifications described herein, in which at least one of the amino acids comprises an acyl group and at least one of the amino acids is covalently bonded to a hydrophilic moiety (e.g., PEG). In some embodiments, the acyl group is attached via a spacer comprising Cys, Lys, Orn, homo-Cys, or Ac-Phe, and the hydrophilic moiety is incorporated at a Cys residue.

Alternatively, the peptides can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In accordance with some embodiments, the peptide comprises an alkylated amino acid (e.g., a non-coded alkylated amino acid (e.g., an amino acid comprising an alkyl group which is non-native to a naturally-occurring amino acid)). Alkylation can be carried out at any positions within the peptides, including any of the positions described herein as a site for acylation, including but not limited to, any of amino acid positions, at a position within a C-terminal extension, or at the C-terminus, provided that the biological activity is retained. The alkyl group can be covalently linked directly to an amino acid of the peptides, or indirectly to an amino acid of the peptides via a spacer, wherein the spacer is positioned between the amino acid of the peptides and the alkyl group. The peptides may be alkylated at the same amino acid position where a hydrophilic moiety is linked, or at a different amino acid position. In specific aspects, the peptides are modified to comprise an alkyl group by direct alkylation of an amine, hydroxyl, or thiol of a side chain of an amino acid of the peptides. In this regard, the alkylated peptides can comprise an amino acid sequence with at least one of the amino acids modified to any amino acid comprising a side chain amine, hydroxyl, or thiol. In yet other embodiments, the amino acid comprising a side chain amine, hydroxyl, or thiol is a disubstituted amino acid. In some embodiments, the alkylated peptide comprises a spacer between the peptide and the alkyl group. In some embodiments, the peptide is covalently bound to the spacer, which is covalently bound to the alkyl group. In some exemplary embodiments, the peptide is modified to comprise an alkyl group by alkylation of an amine, hydroxyl, or thiol of a spacer, which spacer is attached to a side chain of an amino acid. The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In some embodiments, the spacer is an amino acid comprising a side chain amine, hydroxyl, or thiol or a dipeptide or tripeptide comprising an amino acid comprising a side chain amine, hydroxyl, or thiol. When alkylation occurs through an amine group of a spacer, the alkylation can occur through the alpha amine of an amino acid or a side chain amine. In the instance in which the alpha amine is alkylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp and Glu, provided that the alkylation occurs on the alpha amine of the acidic residue. In the instance in which the side chain amine of the amino acid of the spacer is alkylated, the amino acid of the spacer is an amino acid comprising a side chain amine, e.g., an amino acid of Formula I-III (e.g., Lys or Orn). In this instance, it is possible for both the alpha amine and the side chain amine of the amino acid of the spacer to be alkylated, such that the peptide is dialkylated. Embodiments of the invention include such dialkylated molecules. When alkylation occurs through a hydroxyl group of a spacer, the amino acid can be Ser. When alkylation occurs through a thiol group of spacer, the amino acid can be Cys. In some embodiments, the spacer is a hydrophilic bifunctional spacer. Suitable methods of peptide alkylation via amines, hydroxyls, and thiols are known in the art. For example, a Williamson ether synthesis can be used to form an ether linkage between a hydroxyl group of the peptides and the alkyl group. Also, a nucleophilic substitution reaction of the peptide with an alkyl halide can result in any of an ether, thioether, or amino linkage. The alkyl group of the alkylated peptides can be of any size, e.g., any length carbon chain, and can be linear or branched. In some embodiments, the alkyl group is a $C_4$ to $C_{30}$ alkyl. For example, the alkyl group can be any of a $C_4$ alkyl, $C_6$ alkyl, $C_8$ alkyl, $C_{10}$ alkyl, $C_{12}$ alkyl, $C_{14}$ alkyl, $C_{16}$ alkyl, $C_{18}$ alkyl, $C_{20}$ alkyl, $C_{22}$ alkyl, $C_{24}$ alkyl, $C_{26}$ alkyl, $C_{28}$ alkyl, or a $C_{30}$ alkyl. In some embodiments, the alkyl group is a $C_8$ to $C_{20}$ alkyl, e.g., a $C_{14}$ alkyl or a $C_{16}$ alkyl. In some embodiments of the disclosure, the peptide comprises an alkylated amino acid by reacting a nucleophilic, long chain alkane with the peptide, wherein the peptide comprises a leaving group suitable for nucleophilic substitution. In specific aspects, the nucleophilic group of the long chain alkane comprises an amine, hydroxyl, or thiol group (e.g., octadecylamine, tetradecanol, and hexadecanethiol). The leaving group of the peptide can be part of a side chain of an amino acid or can be part of the peptide backbone. Suitable leaving groups include, for example, N-hydroxysuccinimide, halogens, and sulfonate esters. In certain embodiments, the peptide is modified to comprise an alkyl group by reacting the nucleophilic, long chain alkane with a spacer which is attached to the peptide, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group. With regard to these aspects of the disclosure, in which a long chain alkane is alkylated by the peptides or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane. Also, in some embodiments, alkylation can occur between the peptides and a cholesterol moiety. For example, the hydroxyl group of cholesterol can displace a leaving group on the long chain alkane to form a cholesterol-peptides product. The alkylated peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. Alternatively, the alkylated peptides can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In some embodiments, the peptide comprises at position 1 or 2, or at both positions 1 and 2, an amino acid which achieves resistance of the peptides to peptidase cleavage. In some embodiments, the peptide comprises at position 1 an amino acid selected from the group consisting of: D-histidine, desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA). In some embodiments, the peptide comprises at position 2 an amino acid selected from the group consisting of: D-serine, D-alanine, valine, glycine, N-methyl serine, N-methyl alanine, or alpha, aminoisobutyric acid. In some embodiments, the peptide comprises at position 2 an amino acid which achieves resistance of the peptide to peptidases and the amino acid which achieves resistance of the peptide to peptidases is not D-serine. In some embodiments, this covalent bond is an intramolecular bridge other than a lactam bridge. For example, suitable covalent bonding methods include any one or more of olefin metathesis, lanthionine-based cyclization, disulfide bridge or modified sulfur-containing bridge formation, the use of α,ω-diaminoalkane tethers, the formation of metal-atom bridges, and other means of peptide cyclization.

In some embodiments, the peptide is modified by amino acid substitutions and/or additions that introduce a charged amino acid into the C-terminal portion of the analog. In some embodiments, such modifications enhance stability and solubility. As used herein the term "charged amino acid" or "charged residue" refers to an amino acid that comprises a side chain that is negative-charged (i.e., de-protonated) or positive-charged (i.e., protonated) in aqueous solution at physiological pH. In some aspects, these amino acid substitutions and/or additions that introduce a charged amino acid modifications are at a C-terminal position. In some embodiments, one, two or three (and in some instances, more than three) charged amino acids are introduced at the C-terminal position. In exemplary embodiments, one, two or all of the charged amino acids are negative-charged. The negative-charged amino acid in some embodiments is aspartic acid, glutamic acid, cysteic acid, homocysteic acid, or homoglutamic acid. In some aspects, these modifications increase solubility.

In accordance with some embodiments, the peptides disclosed herein are modified by truncation of the C-terminus by one or two amino acid residues. In this regard, the peptides can comprise the sequences (SEQ ID NO: 1-213, 230-236 and 239), optionally with any of the additional modifications described herein.

In some embodiments, the peptide comprises a modified SEQ ID NO: 1-213, 230-236 and 239 in which the carboxylic acid of the C-terminal amino acid is replaced with a charge-neutral group, such as an amide or ester. Accordingly, in some embodiments, the peptide is an amidated peptide, such that the C-terminal residue comprises an amide in place of the alpha carboxylate of an amino acid. As used herein a general reference to a peptide or analog is intended to encompass peptides that have a modified amino terminus, carboxy terminus, or both amino and carboxy termini. For example, an amino acid chain composing an amide group in place of the terminal carboxylic acid is intended to be encompassed by an amino acid sequence designating the standard amino acids.

The invention further provides conjugates comprising one or more of the peptides described herein conjugated to a heterologous moiety. As used herein, the term "heterologous moiety" is synonymous with the term "conjugate moiety" and refers to any molecule (chemical or biochemical, naturally-occurring or non-coded) which is different from the peptides described herein. Exemplary conjugate moieties that can be linked to any of the analogs described herein include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments a conjugate is provided comprising a peptide of the present invention and a plasma protein, wherein the plasma protein is selected from the group consisting of albumin, transferin, fibrinogen and globulins. In some embodiments the plasma protein moiety of the conjugate is albumin or transferin. The conjugate in some embodiments comprises one or more of the peptides described herein and one or more of: a different peptide (which is distinct from the peptides described herein), a polypeptide, a nucleic acid molecule, an antibody or fragment thereof, a polymer, a quantum dot, a small molecule, a toxin, a diagnostic agent, a carbohydrate, an amino acid. In some embodiments, the heterologous moiety is a polymer. In some embodiments, the polymer is selected from the group consisting of: polyamides, polycarbonates, polyalkylenes and derivatives thereof including, polyalkylene glycols, polyalkylene oxides, polyalkylene terephthalates, polymers of acrylic and methacrylic esters, including poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene. In some aspects, the polymer is a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion. In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly (methyl acrylate), poly(isopropyl acrylate), poly(isobutyl acrylate), and poly(octadecyl acrylate). In some embodiments, the polymer is a water-soluble polymer or a hydrophilic polymer. Hydrophilic polymers are further described herein under "Hydrophilic Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In specific embodiments, the polymer is a polyalkylene glycol, including, for example, polyethylene glycol (PEG). In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan. In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid. In some embodiments, the heterologous moiety is attached via non-covalent or covalent bonding to the peptide of the present disclosure. In certain aspects, the heterologous moiety is attached to the peptide of the present disclosure via a linker. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other. The peptide in some embodiments is linked to conjugate moieties via direct covalent linkage by reacting targeted amino acid residues of the analog with an organic derivatizing agent that is capable of reacting with selected side chains or the N- or C-terminal residues of these targeted amino acids. Reactive groups on the analog or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the analog indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier. Cysteinyl residues are most commonly reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Carboxyl side groups (aspartyl or glutamyl) are selectively modified by reaction with carbodiimides (R—N=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions. Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group. Another type of covalent modification involves chemically or enzymatically coupling glycosides to the peptide. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981). In some embodiments, the peptide is conjugated to a heterologous moiety via covalent linkage between a side chain of an amino acid of the peptides and the heterologous moiety. In some aspects, the amino acid covalently linked to a heterologous moiety (e.g., the amino acid comprising a heterologous moiety) is a Cys, Lys, Orn, homo-Cys, or Ac-Phe, and the side chain of the amino acid is covalently bonded to a heterologous moiety. In some embodiments, the conjugate comprises a linker that joins the peptide to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art. As noted above, in some embodiments, the peptides are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC). For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In related embodiments, the Fc region may comprise one or more native or modified constant regions from an immunoglobulin heavy chain, other than CH1, for example, the CH2 and CH3 regions of IgG and IgA, or the CH3 and CH4 regions of IgE. Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372: 379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain. Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279(34):35320-5, 2004). Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety. The peptides described herein can be further modified to improve its solubility and stability in aqueous solutions at physiological pH, while retaining the biological activity. Hydrophilic moieties such as PEG groups can be attached to the analogs under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the analog by reductive alkylation, the polymer selected should have a single reactive aldehyde so that the degree of polymerization is controlled. See, for example, Kinstler et al., Adv. Drug. Delivery Rev. 54: 477-485 (2002); Roberts et al., Adv. Drug Delivery Rev. 54: 459-476 (2002); and Zalipsky et al., Adv. Drug Delivery Rev. 16: 157-182 (1995). In specific aspects, an amino acid residue of the peptides having a thiol is modified with a hydrophilic moiety such as PEG. In some embodiments, the thiol is modified with maleimide-activated PEG in a Michael addition reaction to result in a PEGylated analog comprising a thioether linkage. In some embodiments, the thiol is modified with a haloacetyl-activated PEG in a nucleophilic substitution reaction to result in a PEGylated analog comprising a thioether linkage. Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propopylene glycol homopolymers (PPG) and other polyakylene oxides, polypropylene oxide/ethylene oxide copolymers, colonic acids or other polysaccharide polymers, Ficoll or dextran and mixtures thereof. Dextrans are polysaccharide polymers of glucose subunits, predominantly linked by α1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD. Linear or branched polymers are contemplated. Resulting preparations of conjugates may be essentially monodisperse or polydisperse, and may have about 0.5, 0.7, 1, 1.2, 1.5 or 2 polymer moieties per analog. In some embodiments, the peptide is conjugated to a hydrophilic moiety via covalent linkage between a side chain of an amino acid of the peptide and the hydrophilic moiety. In some embodiments, the peptide is conjugated to a hydrophilic moiety via the side chain of an amino acid, a position within a C-terminal extension, or the C-terminal amino acid, or a combination of these positions. In some aspects, the amino acid covalently linked to a hydrophilic moiety (e.g., the amino acid comprising a hydrophilic moiety) is a Cys, Lys, Orn, homo-Cys, or Ac-Phe, and the side chain of the amino acid is covalently bonded to a hydrophilic moiety (e.g., PEG). In some embodiments, the conjugate of the present disclosure comprises the peptide fused to an accessory analog which is capable of forming an extended conformation similar to chemical PEG (e.g., a recombinant PEG (rPEG) molecule), such as those described in International Patent Application Publication No. WO2009/023270 and U.S. Patent Application Publication No. US20080286808. The rPEG molecule in some aspects is a polypeptide comprising one or more of glycine, serine, glutamic acid, aspartic acid, alanine, or proline. In some aspects, the rPEG is a homopolymer, e.g., poly-glycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly(Gly-Pro), poly(Ser-Glu), etc. In some aspects, the rPEG comprises three different types of amino acids, e.g., poly(Gly-Ser-Glu). In specific aspects, the rPEG increases the half-life of the peptide. In some aspects, the rPEG comprises a net positive or net negative charge. The rPEG in some aspects lacks secondary structure. In some embodiments, the rPEG is greater than or equal to 10 amino acids in length and in some embodiments is about 40 to about 50 amino acids in length. The accessory peptide in some aspects is fused to the N- or C-terminus of the peptide of the present disclosure through a peptide bond or a proteinase cleavage site, or is inserted into the loops of the peptide of the present disclosure. The rPEG in some aspects comprises an affinity tag or is linked to a PEG that is greater than 5 kDa. In some embodiments, the rPEG confers the peptide of the present disclosure with an increased hydrodynamic radius, serum half-life, protease resistance, or solubility and in some aspects confers the analog with decreased immunogenicity.

The invention further provides multimers or dimers of the peptides disclosed herein, including homo- or hetero-multimers or homo- or hetero-dimers. Two or more of the analogs can be linked together using standard linking agents and procedures known to those skilled in the art. For example, dimers can be formed between two peptides through the use of bifunctional thiol crosslinkers and bi-functional amine crosslinkers, particularly for the analogs that have been substituted with cysteine, lysine ornithine, homocysteine or acetyl phenylalanine residues. The dimer can be a homodimer or alternatively can be a heterodimer. In certain embodiments, the linker connecting the two (or more) analogs is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together.

Peptides of the invention are made in a variety of ways known in the art. Suitable methods of de novo synthesizing peptides are described in, for example, Merrifield, J. Am. Chem. Soc, 85, 2149 (1963); Davis et al., Biochem. Intl., 10, 394-414 (1985); Larsen et al., J. Am. Chem. Soc, 115, 6247 (1993); Smith et al., J. Peptide Protein Res., 44, 183 (1994); O'Donnell et al., J. Am. Chem. Soc, 118, 6070 (1996); Stewart and Young, Solid Phase Peptide Synthesis, Freeman (1969); Finn et al., The Proteins, 3 ed., vol. 2, pp. 105-253 (1976); Erickson et al., The Proteins, 3$^{rd}$ ed., vol. 2, pp. 257-527 (1976); and Chan et al., Fmoc Solid Phase Peptide Synthesis, Oxford University Press, Oxford, United Kingdom, 2005. The invention contemplates synthetic peptides.

Alternatively, the peptide is expressed recombinantly by introducing a nucleic acid encoding a peptide of the invention into host cells, which are cultured to express the peptide using standard recombinant methods. Exemplary nucleic acids include deoxyribonucleic acid (DNA) and ribonucleic acids (RNA). In some variations, the nucleic acid is introduced in an expression vector. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, N.Y., 1994. Such peptides are purified from the culture media or cell pellets.

In some embodiments, the peptides of the disclosure are isolated. In some embodiments, the peptides of the disclosure are purified. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

In some embodiments, the peptides described herein are commercially synthesized by companies, such as Innopep Inc. (San Diego, Calif.). In this respect, the peptides can be synthetic, recombinant, isolated, and/or purified.

The peptides of the present disclosure can be provided in accordance with one embodiment as part of a kit. Accordingly, in some embodiments, a kit for administering a peptide, to a patient in need thereof is provided wherein the kit comprises a peptide as described herein.

In one embodiment the kit is provided with a device for administering the composition to a patient, e.g., syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the peptide in a lyophilized form or in an aqueous solution. The kits in some embodiments comprise instructions for use. In accordance with one embodiment the device of the kit is an aerosol dispensing device, wherein the composition is prepackaged within the aerosol device. In another embodiment the kit comprises a syringe and a needle, and in one embodiment the sterile composition is prepackaged within the syringe.

A further embodiment of the invention includes a process of treating cancer comprising
i. A] prescribing
ii. B] selling or advertising to sell,
iii. C] purchasing,
iv. D] instructing to self-administer, or
v. E] administering
of a compound described herein, wherein the compound has been approved by a regulatory agency for the treatment of a condition, to a subject in need of treatment.

A further embodiment of the invention includes a method of supplying a peptide for treating a disease, said method comprises reimbursing a physician, a formulary, a patient or an insurance company for the sale of said peptide.

Definitions

The terms "peptide" refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified peptides. A peptide may be monomeric or polymeric. In certain embodiments, "peptides" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "therapeutic peptide" refers to peptides or fragments or variants thereof, having one or more therapeutic and/or biological activities.

The term "analog" as used herein describes a peptide comprising one or more amino acid modifications, such as but not limited to substitution and/or one or more deletion and/or one or more addition of any one of the amino acid residues for any natural or unnatural amino acid, synthetic amino acids or peptidomimetics and/or the attachment of a side chain to any one of the natural or unnatural amino acids, synthetic amino acids or peptidomimetics at any available position. The addition or deletion of amino acid residues can take place at the N-terminal of the peptide and/or at the C-terminal of the peptide.

Peptide sequences are indicated using standard one- or three-letter abbreviations. Unless otherwise indicated, peptide sequences have their amino termini at the left and their carboxy termini at the right. A particular section of a peptide can be designated by amino acid residue number such as amino acids 3 to 6, or by the actual residue at that site such as Met3 to Gly6. A particular peptide sequence also can be described by explaining how it differs from a reference sequence.

When used herein the term "natural amino acid" is an amino acid (with the usual three letter codes & one letter codes in parenthesis) selected from the group consisting of: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If anywhere in this invention reference is made to a peptide, analog or derivative or peptides according to this invention comprising or not comprising G, P, A, V, L, I, M, C, F, Y, H, K, R, Q, N, E, D, S or T, without specifying further, amino acids are meant. If not otherwise indicated amino acids indicated with a single letter code in CAPITAL letters indicate the L-isoform, if however the amino acid is indicated with a lower case letter, this amino acid is used/applied as it's D-form.

If, due to typing errors, there are deviations from the commonly used codes, the commonly used codes apply. The amino acids present in the peptides of the present invention are, preferably, amino acids which can be coded for by a nucleic acid. As is apparent from the above examples, amino acid residues may be identified by their full name, their one-letter code, and/or their three-letter code. These three ways are fully equivalent.

A "non-conservative amino acid substitution" refers to the substitution of a member of one of these classes for a member from another class. In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included. It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0.+−. 1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included.

Other exemplary amino acid substitutions are set forth in Table 3.

TABLE 3

| Original Residues | Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Nle | Leu |
| Leu | Norleucine, Ile, Val, Met, Ala, Phe | Ile |
| Lys | Arg, Gln, Asn, 1,4-Diamino-butyric Acid | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Nle | Leu |

As used herein the term "charged amino acid" or "charged residue" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

A skilled artisan will be able to determine suitable variants of peptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar peptides. In further embodiments, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, the skilled artisan can predict the importance of amino acid residues in a peptide that correspond to amino acid residues important for activity or structure in similar peptides. One skilled in the art may opt for chemically similar amino acid substitutions for such predicted important amino acid residues.

One skilled in the art can also analyze the three-dimensional structure and amino acid sequence in relation to that structure in similar peptides. In view of such information, one skilled in the art may predict the alignment of amino acid residues of a peptide with respect to its three-dimensional structure. In certain embodiments, one skilled in the art may choose to not make radical changes to amino acid residues predicted to be on the surface of the peptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "derivative" as used herein means a chemically modified peptide, in which one or more side chains have been covalently attached to the peptide. The term "side chain" may also be referred to as a "substituent". A derivative comprising such side chains will thus be "derivatized" peptide or "derivatized" analog. The term may also refer to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated. The term may also refer to peptides of the invention as used herein which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

A modified amino acid residue is an amino acid residue in which any group or bond was modified by deletion, addition, or replacement with a different group or bond, as long as the functionality of the amino acid residue is preserved or if functionality changed (for example replacement of tyrosine with substituted phenylalanine) as long as the modification did not impair the activity of the peptide containing the modified residue.

The term "substituent" or "side chain" as used herein means any suitable moiety bonded, in particular covalently bonded, to an amino acid residue, in particular to any available position on an amino acid residue. Typically, the suitable moiety is a chemical moiety.

The term "fatty acid" refers to aliphatic monocarboxylic acids having from 4 to 28 carbon atoms, it is preferably un-branched, and it may be saturated or unsaturated. In the present invention fatty acids comprising 10 to 16 amino acids are preferred.

The term "fatty diacid" refers to fatty acids as defined above but with an additional carboxylic acid group in the omega position. Thus, fatty diacids are dicarboxylic acids. In the present invention fatty acids comprising 14 to 20 amino acids are preferred.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homolog of a given sequence has greater than 80% sequence homology over a length of the given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. (Id). In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance.

The term "cells expressing the mutant p53 protein" as used herein refers to cells which express from at least one allele a mutant p53 protein. In certain embodiments, the term "cells expressing the mutant p53 protein" is interchangeable with "cancer cells".

The term "pro-apoptotic genes" refers to a gene, or a multitude of genes, involved in apoptosis, either directly (such as certain caspases) or indirectly (for example, as part of a signal transduction cascade).

The term "associated with a mutant p53 protein" as used herein refers to any disease, disorder or condition which is caused by a mutant p53 protein or related to the presence of a mutant p53 protein in a cell or an organ.

It should be understood that since p53 is expressed from both alleles, the overall content of intra-cellular p53 can be either wild-type (wt/wt), mixture of wt and mutant p53 (wt/mut) or mutant p53 only (when both alleles are mutated (mut/mut), or one allele is deleted (mut/−)). In cancer, the situation is often wt/mut, mut/mut or mut/−. Since p53 acts as a tetramer, mutant p53 proteins may abrogate the activity of wild type p53 proteins, which do exist in the cancer's cells. Therefore, the peptides provided by the present invention are particularly useful in treating cancers in which increasing the level of wild type p53 proteins is not fruitful.

As used herein, the term p53 is directed to a p53 protein that can have a conformation of a WT p53, a mutated p53, or an intermediate conformation between WT and mutated p53.

As used herein, the terms "wild type p53", "wt p53" and "WT p53" may interchangeably be used and are directed to a wild type p53 protein, having the conformation of a wild type p53 protein and hence, activity of a wild type p53 protein. In some embodiments, wild type p53 can be identified by a specific monoclonal antibody.

As used herein, the terms "mutant p53", "Mut-p53", "mutated p53", and "p53 mutant" may interchangeably be used and are directed to a mutated p53 protein, incapable of efficiently functioning in a target cell. In some embodiments, a Mut-p53 cannot bind its target site. In some embodiments, a Mut-p53 is mutated at the DNA binding domain (DBD) region. In some embodiments, a Mut-p53 is misfolded in an inactive conformation. In some exemplary embodiments, the Mut-p53 is a temperature sensitive (ts) mut p53 R249S (R249S p53), a hot spot full length mutant p53 Mut-p53 R175H (R175H p53), or any other Mut-p53 protein. In some embodiments, a Mut-p53 is identified by a specific monoclonal antibody, capable of recognizing a misfolded conformation of p53 (induced by the mutation of the p53). In some embodiments, a Mut-p53 is identified by a specific monoclonal antibody.

The phrase "peptide reactivates a mutant p53 protein" as used herein refers to a peptide which upon its interaction with a mutant p53 protein, the mutant p53 protein increases at least one of his activities, wherein the activities are the activities of a wild type p53 protein. For example, upon its interaction with a peptide provided by the present invention, a mutant p53 protein may increase, directly or indirectly, the expression of pro-apoptotic proteins such as caspases in a cancer cell, in a similar way to what would a wild type p53 protein do in a similar situation.

As referred to herein, the terms "reactivating peptide", "Mut-p53 reactivating peptide" may interchangeably be used and are directed to a peptidic agent capable of at least partially restoring activity to Mut-p53. In some embodiments, the reactivating agent can reactivate a Mut-p53 by affecting the conformation of the Mut-p53, to assume a conformation which is more similar to or identical to a native, WT p53. In some embodiments, the reactivating agent can reactivate a Mut-p53 to restore binding of the Mut-p53 to a WT p53 binding site in a target DNA. In some embodiments, the reactivating agent can restore biochemical properties of the Mut-p53. In some embodiments, the reactivating agent can induce the Mut-p53 protein to exhibit p53-selective inhibition of cancer cells. In some embodiments, the reactivating agent can reactivate a Mut-p53 to have structural properties, biochemical properties, physiological properties and/or functional properties similar to or identical to a WT p53 protein. In some embodiments, the reactivating agent is a peptide. In some embodiments, the reactivating agent is a peptide having 5-20 amino acids in length. In some embodiments, the reactivating agent is a peptide having 6-10 amino acids in length.

The term "conformation" with respect to a protein is directed to the structural arrangement (folding) of a protein in space.

A "pharmaceutical composition" refers to a composition suitable for pharmaceutical use in an animal or human. A pharmaceutical composition comprises a pharmacologically and/or therapeutically effective amount of an active agent and a pharmaceutically acceptable carrier. Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). The pharmaceutical compositions are generally formulated as sterile, substantially isotonic and in full compliance with all GMP regulations of the U.S. Food and Drug Administration. The term also encompasses any of the agents listed in the US Pharmacopeia for use in animals, including humans. Suitable pharmaceutical carriers and formulations are described in Remington's Pharmaceutical Sciences, 21st Ed. 2005, Mack Publishing Co, Easton.

"Pharmaceutically acceptable carrier" refers to compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, the composition will include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the peptide of the invention.

As used herein the term "pharmaceutically acceptable salt" refers to salts of peptides that retain the biological activity of the parent peptide, and which are not biologically or otherwise undesirable. Many of the compounds disclosed herein are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, a "therapeutically effective amount" of a peptide that when provided to a subject in accordance with the disclosed and claimed methods effects biological activities such as modulating cell signaling associated with aberrant cellular proliferation and malignancy, impacting cell viability.

The terms "treat", "treating" and "treatment" refer refers to an approach for obtaining beneficial or desired clinical results. Further, references herein to "treatment" include references to curative, palliative and prophylactic treatment. The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

For clarity, the term "instructing" is meant to include information on a label approved by a regulatory agency, in addition to its commonly understood definition.

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variation.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

The pharmaceutical compositions of the present invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or infusions; or kidney dialytic infusion techniques.

In various embodiments, the peptide is admixed with a pharmaceutically acceptable carrier to form a pharmaceutical composition that can be systemically administered to the subject orally or via intravenous injection, intramuscular injection, subcutaneous injection, intraperitoneal injection, transdermal injection, intra-arterial injection, intrasternal injection, intrathecal injection, intraventricular injection, intraurethral injection, intracranial injection, intrasynovial injection or via infusions. The pharmaceutical composition preferably contains at least one component that is not found in nature.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Such unit dosage forms and multi-dose containers, optionally containing a preservative, are additional aspects of the invention. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain carriers such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

Transdermal administration is a still further option, e.g. by needle-free injection, from a patch such as an iontophoretic patch, or via a transmucosal route, e.g. buccally. The present invention includes compositions and methods for transdermal or topical delivery, to act locally at the point of application, or to act systemically once entering the body's blood circulation. In these systems, delivery may be achieved by techniques such as direct topical application of a substance or drug in the form of an ointment or the like, or by adhesion of a patch with a reservoir or the like that holds the drug (or other substance) and releases it to the skin in a time-controlled fashion. For topical administration, the compositions of the present invention can be in the form of emulsions, lotions, gels, creams, jellies, solutions, suspensions, ointments, and transdermal patches. Some topical delivery compositions may contain polyenylphosphatidylcholine (herein abbreviated "PPC"). In some cases, PPC can be used to enhance epidermal penetration. The term "polyenylphosphatidylcholine," as used herein, means any phosphatidylcholine bearing two fatty acid moieties, wherein at least one of the two fatty acids is an unsaturated fatty acid with at least two double bonds in its structure, such as linoleic acid. Such topical formulations may comprise one or more emulsifiers, one or more surfactants, one or more polyglycols, one or more lecithins, one or more fatty acid esters, or one or more transdermal penetration enhancers. Preparations can include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, organic esters such as ethyl oleate, or fixed oils including synthetic mono or di-glycerides. Aqueous solvents include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like.

For example, in one aspect, sterile injectable solutions can be prepared by incorporating a peptide in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation such as vacuum drying and freeze-drying yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. In various embodiments, the injectable compositions will be administered using commercially available disposable injectable devices.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind known in the art. Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the peptides of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the peptides of the disclosure can be formulated as inclusion complexes, such as cyclodextrin inclusion complexes, or liposomes.

The peptide of the present invention can be administered intranasally or by inhalation, typically in the form of a dry powder (either alone, as a mixture, or as a mixed component particle, for example, mixed with a suitable pharmaceutically acceptable carrier) from a dry powder inhaler, as an aerosol spray from a pressurized container, pump, spray, atomiser (preferably an atomiser using electrohydrodynamics to produce a fine mist), or nebulizer, with or without the use of a suitable propellant, or as nasal drops. The pressurized container, pump, spray, atomizer, or nebulizer generally contains a solution or suspension of a peptide of the invention comprising, for example, a suitable agent for dispersing, solubilizing, or extending release of the active, a propellant(s) as solvent. Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying. Capsules, blisters and cartridges for use in an inhaler or insufflator may be formulated to contain a powder mix of the peptide of the invention, a suitable powder base and a performance modifier. Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release. Modified release formulations include delayed-, sustained-, pulsed-, controlled-, targeted and programmed release. In the case of dry powder inhalers and aerosols, the dosage unit is determined by means of a valve which delivers a metered amount. Units in accordance with the invention are typically arranged to administer a metered dose or "puff" of a peptide of the invention. The overall daily dose will typically be administered in a single dose or, more usually, as divided doses throughout the day.

In some embodiments, the peptides (particularly peptide comprised wholly of naturally occurring acids for which codons exist) may be administered as their nucleotide equivalents via gene therapy methods. The polynucleotides that encode the peptides, vectors, and recombinant host cells also are embodiments of the invention.) In one embodiment, the peptide-related polynucleotide is encoded or inserted in a plasmid or vector, which may be derived from an adeno-associated virus (AAV). The AAV may be a recombinant AAV virus and may comprise a capsid serotype such as, but not limited to, of AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ, and AAV-DJ8. As a non-limiting example, the capsid of the recombinant AAV virus is AAV2. As a non-limiting example, the capsid of the recombinant AAV virus is AAVrh10. As a non-limiting example, the capsid of the recombinant AAV virus is AAV9(hu 14). As a non-limiting example, the capsid of the recombinant AAV virus is AAV-DJ. As a non-limiting example, the capsid of the recombinant AAV virus is AAV9.47. As a non-limiting example, the capsid of the recombinant AAV virus is AAV-DJ8. An embodiment comprises the nucleotide equivalents of the peptide sequences described herein whose complete sequence is encoded by codons of the genetic code.

A person skilled in the art may recognize that a target cell may require a specific promoter including but not limited to a promoter that is species specific, inducible, tissue-specific, or cell cycle-specific Parr et al, Nat. Med. 3:1145-9 (1997); the contents of which are herein incorporated by reference in its entirety).

As used herein, a "vector" is any molecule or moiety which transports, transduces or otherwise acts as a carrier of a heterologous molecule such as the polynucleotides of the invention. A "viral vector" is a vector which comprises one or more polynucleotide regions encoding or comprising payload molecule of interest, e.g., a transgene, a polynucleotide encoding a polypeptide or multi-polypeptide. Viral vectors of the present invention may be produced recombinantly and may be based on adeno-associated virus (AAV) parent or reference sequence. Serotypes which may be useful in the present invention include any of those arising from AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ, and AAV-DJ8.

In one embodiment, the serotype which may be useful in the present invention may be AAV-DJ8. The amino acid sequence of AAV-DJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in its entirety, may comprise two mutations: (1) R587Q where arginine (R; arg) at amino acid 587 is changed to glutamine (Q; gln) and (2) R590T where arginine (R; arg) at amino acid 590 is changed to threonine (T; thr). As another non-limiting example, may comprise three mutations: (1) K406R where lysine (K; lys) at amino acid 406 is changed to arginine (R; arg), (2) R587Q where arginine (R; arg) at amino acid 587 is changed to glutamine (Q; gln) and (3) R590T where arginine (R; arg) at amino acid 590 is changed to threonine (T; thr).

AAV vectors may also comprise self-complementary AAV vectors (scAAVs). scAAV vectors contain both DNA strands which anneal together to form double stranded DNA. By skipping second strand synthesis, scAAVs allow for rapid expression in the cell.

In one embodiment, the pharmaceutical composition comprises a recombinant adeno-associated virus (AAV) vector comprising an AAV capsid and an AAV vector genome. The AAV vector genome may comprise at least one peptide-related polynucleotide described herein. The recombinant AAV vectors in the pharmaceutical composition may have at least 70% which contain an AAV vector genome.

In one embodiment, the viral vector comprising a peptide-related polynucleotide may be administered or delivered using the methods for the delivery of AAV virions described in European Patent Application No. EP1857552, the contents of which are herein incorporated by reference in its entirety.

In one embodiment, the viral vector comprising a peptide-related polynucleotide may be administered or delivered using the methods for delivering proteins using AAV vectors described in European Patent Application No. EP2678433, the contents of which are herein incorporated by reference in its entirety.

In one embodiment, the viral vector comprising a peptide-related polynucleotide may be administered or delivered using the methods for delivering DNA molecules using AAV vectors described in U.S. Pat. No. 5,858,351, the contents of which are herein incorporated by reference in its entirety.

In one embodiment, the viral vector comprising a peptide-related polynucleotide may be administered or delivered using the methods for delivering DNA to the bloodstream described in U.S. Pat. No. 6,211,163, the contents of which are herein incorporated by reference in its entirety.

In one embodiment, the viral vector comprising a peptide-related polynucleotide may be administered or delivered using the methods for delivering AAV virions described in U.S. Pat. No. 6,325,998, the contents of which are herein incorporated by reference in its entirety.

In one embodiment, the viral vector comprising a peptide-related polynucleotide may be administered or delivered using the methods for delivering a payload to the central nervous system described in U.S. Pat. No. 7,588,757, the contents of which are herein incorporated by reference in its entirety.

In one embodiment, the viral vector comprising a peptide-related polynucleotide may be administered or delivered using the methods for delivering a payload described in U.S. Pat. No. 8,283,151, the contents of which are herein incorporated by reference in its entirety.

In one embodiment, the viral vector comprising a peptide-related polynucleotide may be administered or delivered using the methods for delivering a payload using a glutamic acid decarboxylase (GAD) delivery vector described in International Patent Publication No. WO 2001/089583, the contents of which are herein incorporated by reference in its entirety.

In one embodiment, the viral vector comprising a peptide-related polynucleotide may be administered or delivered using the methods for delivering a payload to neural cells described in International Patent Publication No. WO 2012/057363, the contents of which are herein incorporated by reference in its entirety.

In one embodiment, the viral vector comprising a peptide-related polynucleotide may be administered or delivered using the methods for delivering a payload to cells described in U.S. Pat. No. 9,585,971, the contents of which are herein incorporated by reference in its entirety.

In one embodiment, the viral vector comprising a peptide-related polynucleotide may be administered or delivered using the methods for delivering a payload to cells described in Deverman et al. Nature Biotechnology, 34, 204-09 (2016).

In one embodiment, the viral vector comprising a peptide-related polynucleotide may be administered or delivered using the methods for the delivery of AAV virions described in U.S. Pat. No. 7,198,951 [adeno-associated virus (AAV) serotype 9 sequences, vectors containing same, and uses therefor], U.S. Pat. No. 9,217,155 [isolation of novel AAV's and uses thereof], WO 2011/126808 [pharmacologically induced transgene ablation system], U.S. Pat. No. 6,015,709 [transcriptional activators, and compositions and uses related thereto], U.S. Pat. No. 7,094,604 [Production of pseudotyped recombinant AAV virions], WO 2016/126993 [anti-tau constructs], U.S. Pat. No. 7,094,604 [recombinant AAV capsid protein], U.S. Pat. No. 8,292,769 [Avian adeno associated viru (aaav) and uses thereof], U.S. Pat. No. 9,102,949 [CNS targeting AAV vectors and methods of use thereof], US 2016-0120960 [adeno-associated virus mediated gene transfer to the central nervous system], WO 2016/073693 [AADC polynucleotides for the treatment of parkinson's disease], WO 2015/168666 [AAV VECTORS FOR RETINAL AND CNS GENE Therapy], US 2009-0117156 [Gene Therapy for Niemann-Pick Disease type A] or WO 2005/120581 [gene therapy for neurometabolic disorders].

Pharmaceutical compositions intended for transderman use may be prepared according to any method known to the art for the manufacture of pharmaceutical compositions.

According to one aspect, the compounds of the invention are for use in medicine, particularly human medicine. The peptides are effective to treat p53 related diseases. In addition to p53, the peptides bind to p63 and p73. Therefore, these peptides have utility in treating diseases impacted by those two proteins.

The present invention also includes methods of treating cancer comprising administering an effective amount of a peptide or a variant thereof to a subject in need of treatment. The peptides provided herein exert a variety of anticancer effects and can be used to treat a wide range of cancers and other proliferative disorders. Peptides provided herein can have a variety of anticancer activities, such as but not limited to, inducing apoptosis in cancerous cells, inhibiting tumor angiogenesis, inhibiting tumor metastasis, modulating the cell cycle, inhibiting cancer cell proliferation, promoting cancer cell differentiation, inhibiting production of and/or protecting against reactive oxygen species, and enhancing stress resistance. The term "cancer" means a disease in mammals that is characterized by uncontrolled, abnormal cell growth and proliferation. General classes of cancers include carcinomas, lymphomas, sarcomas, and blastemas. A "tumor" or "neoplasm" is an abnormal mass of tissue that results from excessive, un controlled, and progressive cell division. Methods described herein are useful for treating cancers and proliferative disorders of any type, including but not limited to, carcinomas, sarcomas, soft tissue sarcomas, lymphomas, hematological cancers, leukemias, germ cell tumors, and cancers without solid tumors (e.g., hematopoietic cancers). In various aspects, the peptides can be used to treat cancers and/or tumors originating from and/or effecting any tissue, including but not limited to, lung, breast, epithelium, large bowel, rectum, testicle, bladder, thyroid, gallbladder, bile duct, biliary tract, prostate, colon, stomach, esophagus, pancreas, liver, kidney, uterus, cervix, ovary, and brain tissues. Non-limiting examples of specific cancers treatable with the peptides include, but are not limited to, acute lymphoblastic leukemia, acute myeloid leukemia, chronic lymphocytic leukemia, chronic myelogenous leukemia, adrenocortical carcinoma, AIDS-related lymphoma, anal cancer, astrocytoma, cerebral basal cell carcinoma, bile duct cancer, extrahepatic bladder cancer, bladder cancer, bone cancer, osteosarcoma/malignant fibrous histiocytoma, brain stem glioma, brain tumor, brain stem glioma, cerebral astrocytoma/malignant glioma, ependymoma, medulloblastoma, supratentorial primitive neuroectodermal tumor, visual pathway and hypothalamic glioma, breast cancer, male bronchial adenomas/carcinoids, Burkitt's lymphoma, carcinoid tumor, gastrointestinal carcinoma of unknown primary central nervous system lymphoma, cervical cancer, chronic lymphocytic leukemia, chronic myelogenous leukemia, chronic myeloproliferative disorders, colon cancer, colorectal cancer, cutaneous t-cell lymphoma, mycosis fungoides and sezary syndrome, endometrial cancer, ependymoma, esophageal cancer, Ewing's family tumors, germ cell tumors, extrahepatic bile duct cancer, eye cancer, intraocular melanoma, retinoblastoma, gallbladder cancer, gastric (stomach) cancer, gastrointestinal carcinoid tumors, ovarian gestational, trophoblastic tumors, glioma, hypothalamic skin cancer (melanoma), skin cancer (non-melanoma), skin carcinoma, small cell lung cancer, small intestine cancer, soft tissue sarcoma, squamous cell carcinoma, squamous neck cancer with occult primary, metastatic stomach (gastric) cancer, stomach (gastric) cancer, t-cell lymphoma, testicular cancer, thymoma, thymic carcinoma, thyroid cancer, transitional cell cancer of the renal pelvis, ureter trophoblastic tumors, transitional cell cancer, urethral cancer, uterine cancer, uterine sarcoma, vaginal cancer, hypothalamic glioma, vulvar cancer, Waldenstrom's macroglobulinemia, Wilms' tumor, hairy cell leukemia, head and neck cancer, hepatocellular (liver) cancer. Hodgkin's lymphoma, hypopharyngeal cancer, islet cell carcinoma (endocrine pancreas), Kaposi's sarcoma, kidney (renal cell) cancer, kidney cancer, laryngeal cancer, hairy cell lip and oral cavity cancer, liver cancer, lung cancer, non-small cell lung cancer, small cell lymphoma, Burkitt's lymphoma, cutaneous t-cell, Hodgkin's lymphoma, non-Hodgkin's lymphoma, Waldenstrom's malignant fibrous histiocytoma of bone/osteosarcoma medulloblastoma, intraocular (eye) merkel cell carcinoma, mesothelioma, malignant mesothelioma, metastatic squamous neck cancer with occult primary multiple endocrine neoplasia syndrome, multiple myeloma/plasma cell neoplasm, mycosis fungoides myelodysplastic syndromes, myelodysplastic/myeloproliferative diseases, myelogenous leukemia, multiple myeloproliferative disorders, chronic nasal cavity and paranasal sinus cancer, nasopharyngeal cancer, pleoropulmonary blastoma, osteosarcoma/malignant fibrous histiocytoma of bone, phceochromocytoma, pineoblastoma, and supratentorial primitive neuroectodermal tumors. In some preferred aspects, the cancer is breast cancer. In some preferred aspects, the cancer is prostate cancer.

In some embodiments of the invention, the peptides have anticancer activity. For example, in some aspects, the peptides have activity against cancer cells, such as but not limited to, ovarian cancer cells. In further aspects, the peptides have anti-proliferative activity against cancer cells, such as but not limited to, ovarian cancer cells.

In some embodiments of the invention, the peptides provided herein have anticancer activity in vivo. For example, in some aspects, the peptides have growth inhibitory activity against tumors in vivo. In further aspects, the peptides increase apoptosis, decreased angiogenesis, and/or reduce proliferation of tumors and/or tumor cells and growth of tumors.

According to another embodiment, the agents of the present invention are coadministered or co-formulated with other known chemotherapeutic agents and/or antiinflammatory agents. The invention also concerns the use of the compound of the present invention in the manufacture of a medicament for the treatment of a condition such as a cancer.

The compound of the present invention, or the pharmaceutically acceptable salts thereof, may also be administered in combination with one or more additional pharmaceutically active compounds/agents, in a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents, in yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can he macromolecules such as a proteins, antibodies, peptibodies, DNA, RNA or fragments of such macromolecules.

Examples of specific pharmaceutically active agents that can be used in combination with one or more peptides of the present invention include: atezolizumab, pembrolizumab, ipilimumab, methotrexate; tamoxifen; fluorouracil; 5-fluorouracil; hydroxyurea; mercaptopurine: cispiatin; carboplatin; daunorubicin; doxorubicin; etoposide; vinblastine; vincristine; pacitaxei; thioguanine; idarubicin; dactinomycin; imatinib; gemcitabine; altretamine; asparaginase; bleomycin; capecitabine; carmustine; cladisat, aq. NaCl solution; cyclophosphamine; cytarabine; decarazine; docetaxel; idarubicin; ifosfamide; irinotecan; fludarabine; mitosmycin; mitoxane; mitoxantrone; topotecan; vinoreibine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasati ib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

The compound of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: the compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure. Treatment of a subject with a therapeutically effective amount of a peptide, of the invention can include a single treatment or, preferably, can include a series of treatments. In a preferred example, a subject is treated with peptide daily, one time per week or biweekly.

It is to be noted that dosage values may vary with the type and severity of the condition to be ameliorated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

The dose of the peptide of the present disclosure also will be determined by the existence, nature and extent of any adverse side effects that might accompany the administration of a particular peptide of the present disclosure. Typically, the attending physician will decide the dosage of the peptide of the present disclosure with which to treat each individual patient, taking into consideration a variety of factors, such as age, body weight, general health, diet, sex, peptide of the present disclosure to be administered, route of administration, and the severity of the condition being treated. By way of example and not intending to limit the invention, the dose of the peptide of the present disclosure can be about 0.0001 to about 100 mg/kg body weight of the subject being treated/day. The peptide can be administered in one or more doses, such as from 1 to 3 doses.

In some embodiments, the pharmaceutical composition comprises any of the analogs disclosed herein at a purity level suitable for administration to a patient. In some embodiments, the analog has a purity level of at least about 90%, preferably above about 95%, more preferably above about 99%, and a pharmaceutically acceptable diluent, carrier or excipient.

The pharmaceutical compositions may be formulated to achieve a physiologically compatible pH. In some embodiments, the pH of the pharmaceutical composition may be at least 5, or at least 6, or at least 7, depending on the formulation and route of administration.

In various embodiments, single or multiple administrations of the pharmaceutical compositions are administered depending on the dosage and frequency as required and tolerated by the subject. In any event, the composition should provide a sufficient quantity of at least one of the peptide disclosed herein to effectively treat the subject. The dosage can be administered once but may be applied periodically until either a therapeutic result is achieved or until side effects warrant discontinuation of therapy.

The dosing frequency of the administration of the peptide pharmaceutical composition depends on the nature of the therapy and the particular disease being treated. Treatment of a subject with a therapeutically effective amount of a peptide, of the invention can include a single treatment or, preferably, can include a series of treatments. In a preferred example, a subject is treated with peptide daily, one time per week or biweekly.

The invention having been described, the following examples are offered by way of illustration, and not limitation.

EXAMPLES

The present disclosures provide peptides comprising a variety of sequences.

Example 1

The peptides of the invention are prepared via solid phase synthesis on a suitable resin using t-Boc or Fmoc chemistry or other well established techniques, (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989; Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000) by a method similar to that described below, unless specified otherwise.

Solid phase synthesis is initiated by attaching an N-terminally protected amino acid with its carboxy terminus to an inert solid support carrying a cleavable linker. This solid support can be any polymer that allows coupling of the initial amino acid, e.g. a Pam resin, trityl resin, a chlorotrityl resin, a Wang resin or a Rink resin in which the linkage of the carboxy group (or carboxamide for Rink resin) to the resin is sensitive to acid (when Fmoc strategy is used). The polymer support is stable under the conditions used to deprotect the α-amino group during the peptide synthesis. After the first amino acid has been coupled to the solid support, the α-amino protecting group of this amino acid is removed. The remaining protected amino acids are then coupled one after the other in the order represented by the peptide sequence using appropriate amide coupling reagents, for example BOP (benzotriazol-1-yl-oxy-tris-(dimethylamino)-phosphonium), HBTU (2-(1H-benzotriazol-1-yl)-1,1,3,3-tetramethyl-uronium), HATU (O-(7-azabenztriazol-1-yl-oxy-tris-(dimethylamino)-phosphonium) or DIC (N,N'-diisopropylcarbodiimide)/HOBt (1-hydroxybenzotriazol), wherein BOP, HBTU and HATU are used with tertiary amine bases. Alternatively, the liberated N-terminus can be functionalized with groups other than amino acids, for example carboxylic acids, etc. Usually, reactive side-chain groups of the amino acids are protected with suitable blocking groups. These protecting groups are removed after the desired peptides have been assembled. They are removed concomitantly with the cleavage of the desired product from the resin under the same conditions. Protecting groups and the procedures to introduce protecting groups can be found in Protective Groups in Organic Synthesis, 3d ed., Greene, T. W. and Wuts, P. G. M., Wiley & Sons (New York: 1999). In some cases it might be desirable to have side-chain protecting groups that can selectively be removed while other side-chain protecting groups remain intact. In this case the liberated functionality can be selectively functionalized. For example, a lysine may be protected with an ivDde protecting group (S. R. Chhabra et al., Tetrahedron Lett. 39, (1998), 1603) which is labile to a very nucleophilic base, for example 4% hydrazine in DMF (dimethyl formamide). Thus, if the N-terminal amino group and all side-chain functionalities are protected with acid labile protecting groups, the ivDde ([1-(4,4-dimethyl-2,6-dioxocyclohex-1-ylidene)-3-methylbutyl] group can be selectively removed using 4% hydrazine in DMF and the corresponding free amino group can then be further modified, e.g. by acylation. The lysine can alternatively be coupled to a protected amino acid and the amino group of this amino acid can then be deprotected resulting in another free amino group which can be acylated or attached to further amino acids. Finally the peptide is cleaved from the resin. This can be achieved by using HF or King's cocktail (D. S. King, C. G. Fields, G. B. Fields, Int. J. Peptide Protein Res. 36, 1990, 255-266). The raw material can then be purified by chromatography, e.g. preparative RP-HPLC, if necessary.

Those peptides, analogs or derivatives of the invention which include non-natural amino acids and/or a covalently attached N-terminal mono- or dipeptide mimetic may be produced as described in the experimental part. Or see e.g., Hodgson et al: "The synthesis of peptides and proteins containing non-natural amino acids", and Chemical Society Reviews, vol. 33, no. 7 (2004), p. 422-430.

The peptides are prepared according to the below-mentioned peptide synthesis and the peptides presented in the Table 1 can be prepared similar to the below-mentioned synthesis, unless specified otherwise.

One method of peptide synthesis is by Fmoc chemistry on a microwave-based Liberty peptide synthesizer (CEM Corp., North Carolina). The resin is Tentagel S RAM with a loading of about 0.25 mmol/g or PAL-ChemMatrix with a loading of about 0.43 mmol/g or PAL AM matrix with a loading of 0.5-0.75 mmol/g. The coupling chemistry is DIC/HOAt or DIC/Oxyma in NMP or DMF using amino acid solutions of 0.3 M and a molar excess of 6-8 fold. Coupling conditions are 5 minutes at up to 70° C. Deprotection is with 10% piperidine in NMP at up to 70° C. The protected amino acids used are standard Fmoc-amino acids (supplied from e.g. Anaspec or Novabiochem or Protein Technologies).

Another method of peptide synthesis is by Fmoc chemistry on a Prelude peptide synthesizer (Protein Technologies, Arizona). The resin is Tentagel S RAM with a loading of about 0.25 mmol/g or PAL-ChemMatrix with a loading of about 0.43 mmol/g or PAL AM with a loading of 0.5-0.75 mmol/g. The coupling chemistry is DIC/HOAt or DIC/Oxyma in NMP or DMF using amino acid solutions of 0.3 M and a molar excess of 6-8 fold. Coupling conditions are single or double couplings for 1 or 2 hours at room temperature. Deprotection is with 20% piperidine in NMP. The protected amino acids used are standard Fmoc-amino acids (supplied from e.g. Anaspec or Novabiochem or Protein Technologies). The crude peptides are purified such as by semipreparative HPLC on a 20 mm×250 mm column packed with either 5 um or 7 um C-18 silica. Peptide solutions are pumped onto the HPLC column and precipitated peptides are dissolved in 5 ml 50% acetic acid $H_2O$ and diluted to 20 ml with $H_2O$ and injected on the column which then is eluted with a gradient of 40-60% $CH_3CN$ in 0.1% TFA 10 ml/min during 50 min at 40° C. The peptide containing fractions are collected. The purified peptide is lyophilized after dilution of the eluate with water.

All peptides with C terminal amides described herein are prepared by a method similar to described below unless specified otherwise. MBHA resin (4-methylbenzhydrylamine polystyrene resin is used during peptide synthesis. MBHA resin, 100-180 mesh, 1% DVB cross-linked polystyrene; loading of 0.7-1.0 mmol/g), Boc-protected and Fmoc protected amino acids can be purchased from Midwest Biotech. The solid phase peptide syntheses using Boc-protected amino acids are performed on an Applied Biosystem 430A Peptide Synthesizer. Fmoc protected amino acid synthesis is performed using the Applied Biosystems Model 433 Peptide Synthesizer.

Synthesis of the peptides is performed on the Applied Biosystem Model 430A Peptide Synthesizer. Synthetic peptides are constructed by sequential addition of amino acids to a cartridge containing 2 mmol of Boc protected amino acid. Specifically, the synthesis is carried out using Boc DEPBT-activated single couplings. At the end of the coupling step, the peptidyl-resin is treated with TFA to remove the N-terminal Boc protecting group. It is washed repeatedly with DMF and this repetitive cycle is repeated for the desired number of coupling steps. After the assembly, the sidechain protection, Fmoc, is removed by 20% piperidine treatment and acylation was conducted using DIC. The peptidyl-resin at the end of the entire synthesis is dried by using DCM, and the peptide is cleaved from the resin with anhydrous HF. The peptidyl-resin is treated with anhydrous HF, and this typically yielded approximately 350 mg (~50% yield) of a crude deprotected-peptide. Specifically, the peptidyl-resin (30 mg to 200 mg) is placed in the hydrogen fluoride (HF) reaction vessel for cleavage. 500 μL of p-cresol was added to the vessel as a carbonium ion scavenger. The vessel is attached to the HF system and submerged in the methanol/dry ice mixture. The vessel is evacuated with a vacuum pump and 10 ml of HF is distilled to the reaction vessel. This reaction mixture of the peptidyl-resin and the HF is stirred for one hour at 0° C., after which a vacuum is established and the HF is quickly evacuated (10-15 min). The vessel is removed carefully and filled with approximately 35 ml of ether to precipitate the peptide and to extract the p-cresol and small molecule organic protecting groups resulting from HF treatment. This mixture is filtered utilizing a teflon filter and repeated twice to remove all excess cresol. This filtrate is discarded. The precipitated peptide dissolves in approximately 20 ml of 10% acetic acid (aq). This filtrate, which contained the desired peptide, is collected and lyophilized.

Example 2

Figure 3:
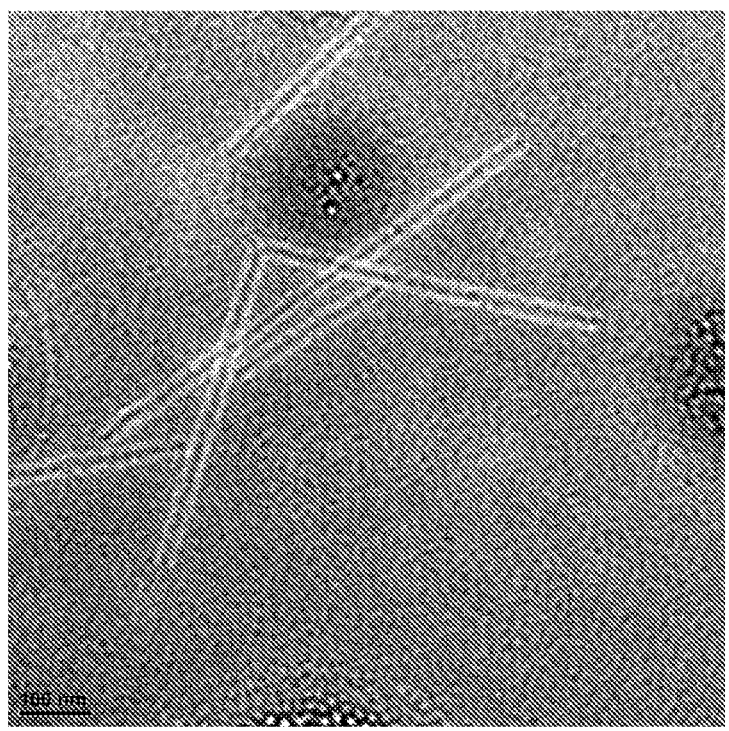
FIG. 3 shows electronic miscroscopy images of the formation of fibrils from the aggregation of Nat1.

Nat forms aggregation related fibrils. Electronic microscopy images of the formation of fibrils from the aggregation of Nat1 is shown in FIG. 3. Nat1 is dissolved in DMSO, then diluted and to a final concentration of 200 µM in 150 mM NaCl. 50 mM Hepes pH7.3. The solution is incubated at room temperature. Images are made on a FEI TF20 TEM.

Example 3

The peptides of the invention were tested in an in vitro Thioflavin T aggregation assay [see WO2014/182961]. An increase in Thioflavin T fluorescence is detected over time due to the formation of increasing amounts of amyloid to which the dye can specifically bind. The peptide is added in solution at different concentrations and is able to delay the aggregation onset and lower the total amount of aggregates present, in a concentration dependent fashion. For the Nat1 Stock Solution, Nat (LTIITLE (SEQ ID NO: 225), >95% Pure, TFA salt) is dissolved at 8 mM in 25 mM NaOH solution and kept at −80° C. Prior to the assay, it is diluted to 1 mM in $H_2O$. The 2× Reaction Buffer is prepared with 200 mM Sodium Phosphate, pH6.0, 500 mM Sodium Chloride and 200 µM Thioflavin T (ThT). 100 µL of 2× reaction buffer and 80 µL of $H_2O$ are added to each well in black, clear-bottomed 96-well plate. Inhibitor peptides are dissolved in $H_2O$ to appropriate concentrations to produce 6-points dose response curves. 10 µL of dissolved peptide or $H_2O$ (control) is added to each reaction well. 10 µL of 1 mM Nat1 peptide is added to each reaction well (a final concentration of 50 µM). ThT fluorescence is monitored at room temperature every minute for 2 hours with excitation and emission wavelengths of 440 and 485 nm, respectively. $IC_{50}$ values are calculated using Graphpad Prism. The results are reported in Table 4.

TABLE 4

Thioflavin T aggregation assay

| Peptide | SEQ ID NO: | IC50 (nM) |
| --- | --- | --- |
| IRIRHYR | 11 | 14 |
| IRIRAYR | 13 | 23 |
| IRIRRYR | 12 | 27 |
| Ile-homoArg-Ile-homoArg-Arg-Tyr-Arg | 3 | 30 |
| kfrfyhr | 123 | 32 |
| LRIRYWK | 14 | 36 |
| IRIRRAR | 15 | 37 |
| Ile-Arg-Ile-homoArg-Arg-Tyr-Arg | 5 | 40 |
| rihyfrr | 124 | 43 |
| hwrwlrr | 125 | 43 |
| IRIARYR | 16 | 44 |

TABLE 4-continued

Thioflavin T aggregation assay

| Peptide | SEQ ID NO: | IC50 (nM) |
| --- | --- | --- |
| IRIRRYA | 17 | 44 |
| Ile-homoArg-Ile-homoArg-Arg-Trp-Arg | 6 | 49 |
| rwrylrr | 126 | 49 |
| rfhyfrk | 127 | 51 |
| IRIYRYK | 18 | 60 |
| TRIRFYR | 19 | 64 |
| Chg-Arg-Chg-Arg-Arg-Tyr-Arg | 7 | 67 |
| Ac-IRIRRYR-NH2 | 20 | 69 |
| LYIRYLR | 21 | 70 |
| LRIKYHR | 22 | 71 |
| klkklh | 128 | 71 |
| IAIRRYR | 23 | 74 |
| kwrwyrr | 129 | 75 |
| LRIRRYR | 24 | 76 |
| LWIKYHR | 25 | 76 |
| IRIRRWR | 26 | 76 |
| rfyyhrr | 130 | 76 |
| wwrwyrr | 131 | 78 |
| LRIYRVR | 27 | 81 |
| Ile-Arg-Chg-Arg-Arg-Tyr-Arg | 8 | 81 |
| rfyrrhr | 132 | 81 |
| WTIKLWH | 28 | 84 |
| kyrwyrh | 133 | 87 |
| fwrwhr | 134 | 88 |
| LRIRFFR | 29 | 90 |
| LTIRYYK | 30 | 93 |
| qqryywr | 135 | 95 |
| hlriwrn | 136 | 97 |
| YRLRYLR | 31 | 99 |
| LFRYYQK | 32 | 100 |
| LVIRYHR | 33 | 101 |
| ffrfhrr | 137 | 104 |
| RFYRYLR | 34 | 107 |
| lwrryhr | 138 | 108 |
| rirwywk | 139 | 110 |
| yqwrhwr | 140 | 112 |
| rwywhhr | 141 | 115 |
| sfwykrr | 142 | 116 |

TABLE 4-continued

Thioflavin T aggregation assay

| Peptide | SEQ ID NO: | IC50 (nM) |
|---|---|---|
| rfefrhr | 143 | 117 |
| yqyyyqr | 144 | 118 |
| Ile-Arg-Phg-Arg-Arg-Tyr-Arg | 2 | 124 |
| LRI(N-Me)KYHR | 35 | 125 |
| rqwyhwr | 145 | 132 |
| hqryywr | 146 | 138 |
| hwryhrr | 147 | 139 |
| IRIRHYRP | 36 | 142 |
| ARIRRYR | 37 | 144 |
| rwhwhwr | 148 | 145 |
| LRLRHYR | 38 | 146 |
| fwrwhrr | 149 | 147 |
| LYIKYHR | 39 | 148 |
| YTRITYH | 40 | 150 |
| ffrfhhr | 150 | 151 |
| LRIYHHK | 41 | 152 |
| IRLRRYR | 42 | 153 |
| rwrwhhr | 151 | 156 |
| hwrwyk | 152 | 159 |
| fwrhkhr | 153 | 161 |
| fwrwhrr | 149 | 164 |
| qiryfrr | 154 | 167 |
| YRLRYVR | 43 | 175 |
| fwrwarr | 155 | 176 |
| LYIRYTH | 44 | 180 |
| qfrmhhr | 156 | 181 |
| yqyyfwr | 157 | 181 |
| LRIRHYT | 45 | 182 |
| FRIRRYR | 46 | 185 |
| swwfrhr | 158 | 187 |
| yqwryrr | 159 | 191 |
| hlryhrk | 160 | 192 |
| LYIRLTH | 47 | 192 |
| yqwyrwq | 161 | 194 |
| lwrwyrr | 162 | 194 |
| LTIRLWH | 48 | 198 |
| rwrilqk | 163 | 199 |
| LYIRTLH | 49 | 203 |
| WTIRYYK | 50 | 203 |
| IRIRRY | 51 | 205 |
| LFIKYHR | 52 | 210 |
| rqhyrwr | 164 | 210 |
| TRIYRYK | 53 | 213 |
| WTIRYYH | 54 | 214 |
| rlhwkhh | 165 | 215 |
| rwmywqr | 166 | 216 |
| LAIKYHR | 55 | 220 |
| WTRITLK | 56 | 222 |
| fwrwhra | 167 | 228 |
| LTIKLWH | 57 | 232 |
| LLIKYHA | 58 | 234 |
| rqmqyrr | 168 | 236 |
| fwawhrr | 169 | 239 |
| WTRIYLH | 59 | 240 |
| rfyrhhr | 170 | 244 |
| fwrwhar | 171 | 245 |
| hwrwrwr | 172 | 245 |
| krwrhqr | 173 | 245 |
| LRIRHVK | 60 | 246 |
| wwrrhhr | 174 | 247 |
| LLIKYHR | 61 | 248 |
| IRIRRAA | 62 | 248 |
| kqwyhwr | 175 | 252 |
| LYIRTYH | 63 | 257 |
| LLIKAHR | 64 | 258 |
| LTIKLWH | 57 | 260 |
| WYIRLWK | 65 | 262 |
| fwrhkhr | 153 | 264 |
| awrwhrr | 176 | 267 |
| IYIYHQR | 66 | 269 |
| RLYIRLS | 67 | 284 |
| WYIRTYH | 68 | 287 |
| farwhrr | 177 | 287 |
| WYIRLWH | 69 | 288 |
| fwrahrr | 178 | 293 |

TABLE 4-continued

Thioflavin T aggregation assay

| Peptide | SEQ ID NO: | IC50 (nM) |
|---|---|---|
| LTIRTWH | 70 | 295 |
| rqhyhwr | 179 | 296 |
| LLIKYAR | 71 | 301 |
| swrwhhr | 180 | 301 |
| LYIRTWH | 72 | 302 |
| LYIRHK | 73 | 316 |
| LTIRLTH | 74 | 329 |
| LR(N-Me)IKYHR | 75 | 334 |
| shwrrhr | 181 | 338 |
| ywqwrqs | 182 | 338 |
| yqwqyqr | 183 | 354 |
| TLIIYHR | 76 | 357 |
| LYIFRHT | 77 | 363 |
| WYIRLTH | 78 | 369 |
| WTRILWH | 79 | 398 |
| TYIRYLR | 80 | 412 |
| WTRIYYH | 81 | 420 |
| LTIMLWH | 82 | 425 |
| WTKITLH | 83 | 427 |
| LFIYYQR | 84 | 440 |
| IQIYRYK | 85 | 444 |
| IRIRAAR | 86 | 451 |
| fwrwhaa | 184 | 458 |
| LYIRTYH | 63 | 463 |
| LLIAYHR | 87 | 466 |
| wwrfhwr | 185 | 472 |
| WTIRYYH | 54 | 473 |
| LFIFYHR | 88 | 476 |
| IRVYKYS | 89 | 480 |
| LTIQLWH | 90 | 481 |
| LLIKYHR | 61 | 489 |
| YYIRYYK | 91 | 494 |
| IRFRRYR | 92 | 496 |
| WRIRRYR | 93 | 514 |
| WTIMLWH | 94 | 525 |
| LTIRTLH | 95 | 537 |
| ALIKYHR | 96 | 629 |

TABLE 4-continued

Thioflavin T aggregation assay

| Peptide | SEQ ID NO: | IC50 (nM) |
|---|---|---|
| LHIEHR | 97 | 657 |
| rlkwrw | 186 | 702 |
| IFVYHH | 98 | 703 |
| qlkwlh | 187 | 716 |
| WTIKLTH | 99 | 720 |
| IHIEIK | 100 | 723 |
| WTIRTWH | 101 | 784 |
| YTYMLWK | 102 | 824 |
| farahrr | 188 | 906 |
| LSIRQH | 103 | 945 |
| klkwlw | 189 | 1063 |
| IRARRYR | 104 | 1253 |
| WTRITLE [Comparator] | 237 | 1337 |
| ilkwlw | 190 | 1340 |
| YYIRTYH | 105 | 1598 |
| LTRITLE [Comparator] | 238 | 1680 |
| LLAKYHR | 106 | 1726 |
| IWIRRWR | 107 | 1902 |
| AYYYRHR | 108 | 2125 |
| shwrhhr | 191 | 2267 |
| rqwyrwq | 192 | 2720 |
| qwrwrhr | 193 | 3136 |
| TYVYRRR | 109 | 3660 |
| TRIYRVK | 110 | 3742 |
| TYIYRQR | 111 | 5166 |
| qvryhkn | 194 | 5695 |
| Phg-Arg-Phg-Arg-Arg-Tyr-Arg | 4 | 5951 |
| klkwqw | 195 | 7307 |
| LTRILTH | 112 | 7374 |
| ILRLYFR | 113 | 8968 |
| klkway | 196 | 12555 |
| rmwrhhr | 197 | 13209 |
| FFRLYLR | 114 | 13418 |
| LTRILWH | 115 | 16219 |
| FRLYIH | 116 | 16351 |
| TFVFRHR | 117 | 20308 |
| qfhylcrr | 198 | 23903 |
| rfhrhhr | 199 | 30923 |

TABLE 4-continued

Thiofiavin T aggregation assay

| Peptide | SEQ ID NO: | IC50 (nM) |
|---|---|---|
| IRIRRYE | 118 | 32799 |
| hqrryqr | 122 | 39070 |
| YTIQLWH | 119 | 45982 |

Example 4

Figure 1B:
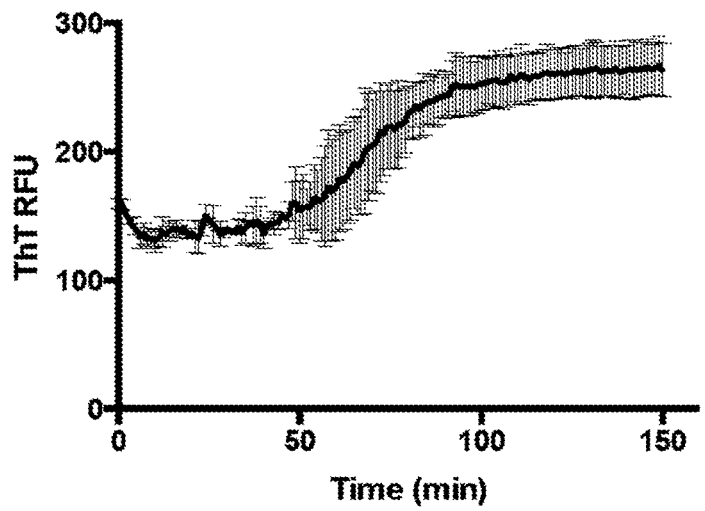
Figure 2A:
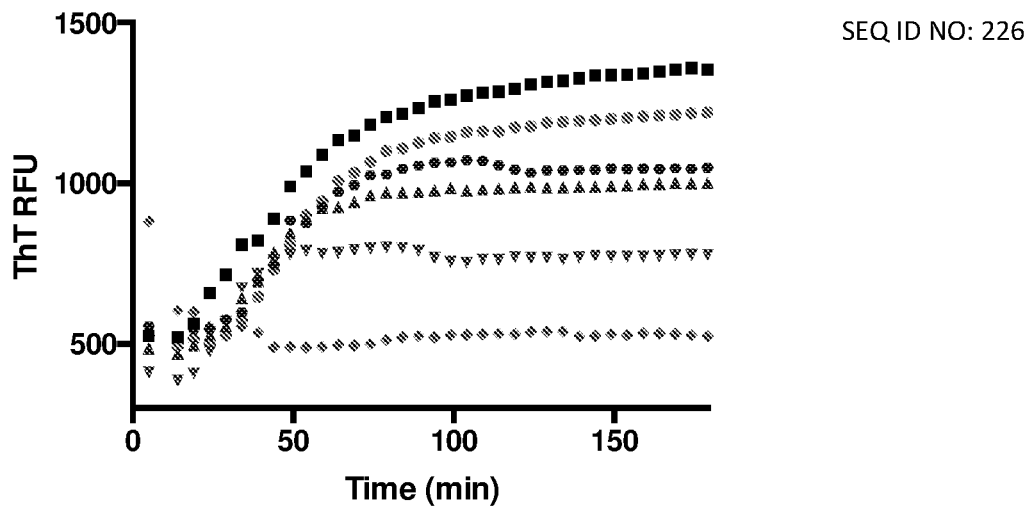
FIGS. 2(a) and 2(b) show the in vitro inhibition of p63 and p73 aggregation by several inhibitors. The aggregation is monitored via Thioflavin T assay. The inhibitors [IRIR-RYR (SEQ ID NO: 12 small circles), TFVFRHR (SEQ ID NO: 117 small triangles), LLIKYHR (SEQ ID NO: 61 large triangles), rfyyhrr (SEQ ID NO: 130 diamonds), and hqrryqr (SEQ ID NO: 122) large circles] are added in solution at 50 mM and delay the aggregation onset and lower the total amount of aggregates present, in a concentration dependent fashion. The baseline of no inhibitor is the line with squares.
Figure 2B:
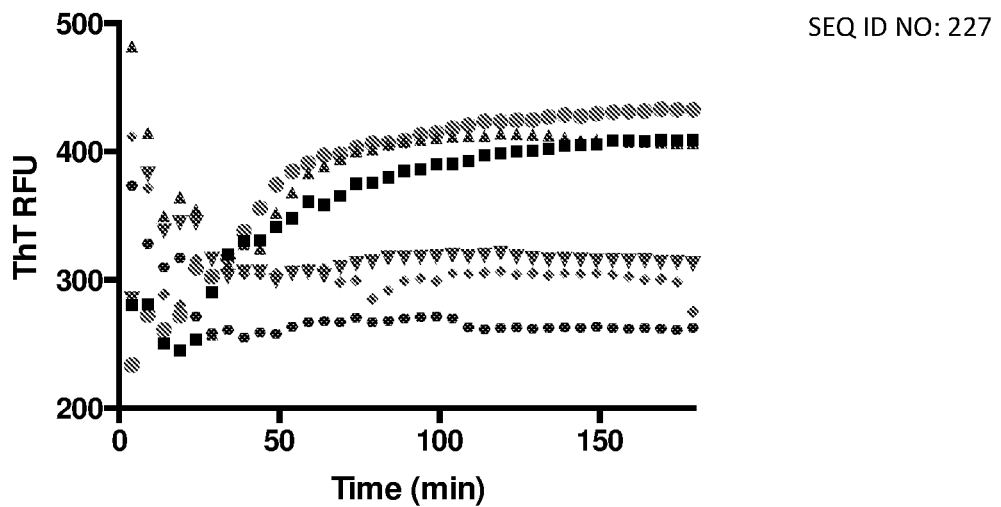

The peptides are tested for p63 binding and p73 binding in an in vitro Thiofiavin T aggregation assay. There are sequences in p63 [RPILIIVTLE—SEQ ID NO: 226] and p73 [RPILIIITLE—SEQ ID NO: 227] that exhibit high homology with the amyloid sequence found in p53 [RPILT-IITLE—SEQ ID NO: 228]. The addition of the 50 µM solutions of p63 and p73 peptides to the reaction Buffer described in Example 3, forms amyloid (FIG. 1(a) and FIG. 1(b)). An increase in Thiofiavin T fluorescence is detected over time due to the formation of increasing amounts of amyloid to which the dye can specifically bind. The inhibitor peptides of the current invention are added in solution at different concentrations and is able to delay the aggregation onset and lower the total amount of aggregates present, in a concentration dependent fashion. For the Nat1 Stock Solution, Nat1 (LTIITLE (SEQ ID NO: 225), >95% Pure, TFA salt) is dissolved at 8 mM in 25 mM NaOH solution and kept at −80° C. Prior to the assay, it is diluted to 1 mM in H$_2$O. The 2× Reaction Buffer is prepared with 200 mM Sodium Phosphate, pH6.0, 500 mM Sodium Chloride and 200 µM Thioflavin T (ThT). 100 µL of 2× reaction buffer and 80 µL of H$_2$O are added to each well in black, clear-bottomed 96-well plate. Inhibitor peptides are dissolved in H$_2$O to appropriate concentrations to produce 6-points dose response curves. 10 µL of dissolved peptide or H$_2$O (control) is added to each reaction well. 10 µL of 1 mM Nat1 peptide is added to each reaction well (a final concentration of 50 µM). ThT fluorescence is monitored at room temperature every minute for 2 hours with excitation and emission wavelengths of 440 and 485 nm, respectively. The results are found in FIG. 2(a) and FIG. 2(b).

Example 5

To render the inhibitors cell permeable, the peptides are fused to either a nine-residue poly L-Arg tag or a nine-residue poly D-Arg tag, through one of several three-residue linkers, either L-RPI, D-RPI, or D-GGG. Cancer cell lines, e.g. OVCAR-3, and Detroit 562 are treated with the peptide conjugates for 24 hours by the following method. OVCAR3 and Detroit-562 cells are grown in ATCC recommended growth media. The peptides were made in a 4 mM stock. Cells are plated in 96-well flat bottom clear plates at 7000 cells/well. After 24 hours, compounds are serially diluted in one-third [starting at 33 µM] or one-half [starting at 30 µM] dilutions in PrEGM media (Lonza). Growth media was removed from the wells and compound in PrEGM was added to 100 ul final volume. 24 hours post-compound addition cell metabolism was measured by addition of 20 µl MTS solution (Promega, cell-titer 96 aqueous). Absorbance was read at 490 nm following a 2 hour incubation and data was processed in Prism Graphpad to generate EC$_{50}$ values. The results are reported in Table 5.

TABLE 5

Cell Assay with CPP Linked peptides

| Sequence | % Protein Binding in Human Serum | Stability in Human Serum (t1/2) (min) | EC$_{50}$ (µM) OVCAR3 in PrEGM | EC$_{50}$ (µM) Detroit-562 in PrEGM | SEQ ID NO |
|---|---|---|---|---|---|
| RRRRRRRRRPILTRITLE | 66 | 339 | 8 | 9 | 229 |
| RRRRRRRRRPIIRIRHYR | 84 | 30 | 6 | 6 | 203 |
| RRRRRRRRRPIIRIRHYP | 83 | 295 | 6 | 7 | 204 |
| PRRRRRRRRRPIIRIRHYRP | 89 | 116 | 10 | 12 | 205 |
| RRRRRRRRRPIIRIRHYRP | 81 | 124 | 7 | 7 | 206 |
| PRRRRRRRRRPILRIRYWKP | 98 | 200 | 5 | 5 | 207 |
| PRRRRRRRRRPITRIRFYRP | 89 | 103 | 8 | 9 | 208 |
| PRRRRRRRRRPIWTIKLWHP | 100 | ND | 4 | 6 | 209 |
| RRRRRRRRRPIqqryywr | 82 | 600 | 22 | 12 | 210 |
| RRRRRRRRRPIyqwyrwq | 98 | 50 | 10 | 13 | 211 |
| RRRRRRRRRPIkfrfyhr | 81 | 265 | 11 | 15 | 212 |
| RRRRRRRRRPIrfyyhrr | 91 | 57 | 16 | 9 | 213 |
| rrrrrrrrrpiyqwyrwq | 99 | >24 hr | 6 | 5 | 230 |
| rrrrrrrrrgggyqwyrwq | 89 | >24 hr | 6 | 8 | 231 |
| rrrrrrrrrpikfrfyhr | 86 | >24 hr | 4 | 5 | 232 |

TABLE 5-continued

Cell Assay with CPP Linked peptides

| Sequence | % Protein Binding in Human Serum | Stability in Human Serum (t1/2) (min) | $EC_{50}$ (µM) OVCAR3 in PrEGM | $EC_{50}$ (µM) Detroit-562 in PrEGM | SEQ ID NO |
|---|---|---|---|---|---|
| rrrrrrrrrpirihyfrr | 93 | >24 hr | 4 | 5 | 233 |
| rrrrrrrrrpikwrwyrr | 94 | >24 hr | 4 | 5 | 234 |
| rrrrrrrrrpihlriwrn | 95 | >24 hr | 4 | 4 | 235 |
| rrrrrrrrrpihqrqyqr | 12 | >24 hr | 27 | 35 | 236 |

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein.

Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

SEQUENCE LISTINGS

This application includes a sequence listing filed electronically and incorporated herein by reference.

What is claimed:

1. A peptide comprising any of

LTRITYH, (SEQ ID NO: 10)

IRIRHYR, (SEQ ID NO: 11)

IRIRRYR, (SEQ ID NO: 12)

IRIRAYR, (SEQ ID NO: 13)

LRIRYWK, (SEQ ID NO: 14)

IRIRRAR, (SEQ ID NO: 15)

IRIARYR, (SEQ ID NO: 16)

IRIRRYA, (SEQ ID NO: 17)

IRIYRYK, (SEQ ID NO: 18)

TRIRFYR, (SEQ ID NO: 19)

Ac-IRIRRYR-NH2, (SEQ ID NO: 20)

-continued

LYIRYLR, (SEQ ID NO: 21)

LRIKYHR, (SEQ ID NO: 22)

IAIRRYR, (SEQ ID NO: 23)

LRIRRYR, (SEQ ID NO: 24)

LWIKYHR, (SEQ ID NO: 25)

IRIRRWR, (SEQ ID NO: 26)

LRIYRVR, (SEQ ID NO: 27)

WTIKLWH, (SEQ ID NO: 28)

LRIRFFR, (SEQ ID NO: 29)

LTIRYYK, (SEQ ID NO: 30)

YRLRYLR, (SEQ ID NO: 31)

LFRYYQK, (SEQ ID NO: 32)

LRLRHYR, (SEQ ID NO: 38)

LYIKYHR, (SEQ ID NO: 39)

YTRITYH, (SEQ ID NO: 40)

LRIYHHK, (SEQ ID NO: 41)

IRLRRYR, (SEQ ID NO: 42)

YRLRYVR, (SEQ ID NO: 43)

LTIRLWH, (SEQ ID NO: 48)

WTIRYYK, (SEQ ID NO: 50)

LFIKYHR, (SEQ ID NO: 52)

TRIYRYK, (SEQ ID NO: 53)

WTIRYYH, (SEQ ID NO: 54)

LAIKYHR, (SEQ ID NO: 55)

LTIKLWH, (SEQ ID NO: 57)

LRIRHVK, (SEQ ID NO: 60)

IRIRRAA, (SEQ ID NO: 62)

-continued

WYIRLWK, (SEQ ID NO: 65)

IYIYHQR, (SEQ ID NO: 66)

WYIRLWH, (SEQ ID NO: 69)

TYIRYLR, (SEQ ID NO: 80)

LFIYYQR, (SEQ ID NO: 84)

IRIRAAR, (SEQ ID NO: 86)

YYIRYYK, (SEQ ID NO: 91)

WRIRRYR, (SEQ ID NO: 93)

IWIRRWR, (SEQ ID NO: 107)

TRIYRVK, (SEQ ID NO: 110)

and

TYIYRQR, (SEQ ID NO: 111)

or C-terminal acids and amides thereof, or N-acetyl derivatives thereof; or pharmaceutically acceptable salts thereof.

2. A peptide of claim 1 that is capable of inhibiting aggregation of p53 and/or p63 and/or p73.

3. A peptide of claim 1 comprising any of

IRIRHYR, (SEQ ID NO: 11)

IRIRRYR, (SEQ ID NO: 12)

LRIRYWK, (SEQ ID NO: 14)

IRIYRYK, (SEQ ID NO: 18)

TRIRFYR, (SEQ ID NO: 19)

WTIKLWH, (SEQ ID NO: 28)

LRIRFFR, (SEQ ID NO: 29)

and

LRLRHYR, (SEQ ID NO: 38)

or C-terminal acids and amides thereof, or N-acetyl derivatives thereof; or pharmaceutically acceptable salts thereof.

4. A peptide comprising an amino acid sequence of Formula Ia':

(Ia')
$(Arg)_n$-Pro-Ile-Xaa1-Xaa2-Xaa3-Xaa4-Xaa5-Xaa6-Xaa7-Xaa8 (SEQ ID NO: 202)

wherein
n is a number between 1 and 16, inclusive;
  Xaa1 is Ile, Leu, Trp, Thr, or Tyr;
  Xaa2 is Arg, Phe, Trp, Thr, Ala, or Tyr;
  Xaa3 is Ile, Arg, or Leu;
  Xaa4 is Arg, Lys, Ala, Tyr;
  Xaa5 is His, Arg, Tyr, Leu, Ala, or Phe;
  Xaa6 is Tyr, Ala, Gln, Leu, Val, His, Trp, or Phe;
  Xaa7 is Arg, Ala, His, or Lys; and
  Xaa8 is absent;
  provided the sequence Xaa1-Xaa2-Xaa3-Xaa4-Xaa5-Xaa6-Xaa7-Xaa8 is not YRIRRYR (SEQ ID NO: 219), IRIAAYR (SEQ ID NO: 221), IRIARAR (SEQ ID NO: 222), IRIARYA (SEQ ID NO: 223) or IRIRAYA (SEQ ID NO: 224);
  or C-terminal acids and amides thereof, or N-acetyl derivatives thereof; or pharmaceutically acceptable salts thereof.

5. The peptide of claim 4 comprising RRRRRRRRRR-PIIRIRHYR (SEQ ID NO: 203); or C-terminal acids and amides thereof, or N-acetyl derivatives thereof;
  or pharmaceutically acceptable salts thereof.

6. The peptide of claim 1, wherein the peptide further comprises a duration enhancing moiety, and optionally further comprises a linker attaching the peptide to the duration enhancing moiety; or C-terminal acids and amides thereof, or N-acetyl derivatives thereof; or pharmaceutically acceptable salts thereof.

7. The peptide of claim 1, wherein the peptide is attached to a cell penetrating peptide (CPP); or C-terminal acids and amides thereof, or N-acetyl derivatives thereof; or pharmaceutically acceptable salts thereof.

8. A pharmaceutical composition comprising a peptide of claim 2 and a pharmaceutically acceptable carrier.

9. A method of treating cancer with a peptide of claim 2 that is capable of inhibiting aggregation of p53, the method comprising administering the peptide to a patient with the cancer, wherein the cancer is characterized by aberrantly folded or aggregated p53.

10. The method according to claim 9 that comprises administering a composition that comprises the peptide and a pharmaceutically acceptable carrier to the patient.

11. The method of claim 9, wherein the cancer is ovarian cancer.

12. A method of affecting p53 aggregation comprising contacting cells or treatment of a patient with a peptide of claim 6 that is capable of inhibiting aggregation of p53.

13. The method of claim 9, wherein the cancer is nasopharyngeal cancer.

14. The peptide according to claim 1 that is less than 25 amino acids in length.

15. The peptide according to claim 2 that is less than 25 amino acids in length.

16. A method of affecting p63 aggregation comprising contacting cells or treatment of a patient with a peptide of claim 2 that is capable of inhibiting aggregation of p63.

17. A method of affecting p73 aggregation comprising contacting cells or treatment of a patient with a peptide of claim 2 that is capable of inhibiting aggregation of p73.

18. A peptide of claim 13 that is capable of inhibiting aggregation of p53 and/or p63 and/or p73.

19. A pharmaceutical composition comprising a peptide of claim 18 and a pharmaceutically acceptable carrier.

20. A method of treating cancer with a peptide of claim 18 that is capable of inhibiting aggregation of p53, the method comprising administering the peptide to a patient with the cancer, wherein the cancer is characterized by aberrantly folded or aggregated p53.

21. The method according to claim 20 that comprises administering a composition that comprises the peptide and a pharmaceutically acceptable carrier to the patient.

22. A pharmaceutical composition comprising a peptide of claim 7 and a pharmaceutically acceptable carrier.

* * * * *

UNITED STATES PATENT AND TRADEMARK OFFICE
CERTIFICATE OF CORRECTION

PATENT NO. : 11,117,930 B2  
APPLICATION NO. : 16/487381  
DATED : September 14, 2021  
INVENTOR(S) : Shiho Tanaka et al.

Page 1 of 1

It is certified that error appears in the above-identified patent and that said Letters Patent is hereby corrected as shown below:

In the Claims

At Column 237, Line 55, delete "LTRITYH, (SEQ ID NO: 10)".

At Column 239, Line 35, delete "YTRITYH, (SEQ ID NO: 40)".

At Column 242, Line 11, "claim 6" should be -- claim 2 --.

At Column 242, Line 23, "claim 13" should be -- claim 4 --.

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*